(12) United States Patent
Yang

(10) Patent No.: US 12,058,986 B2
(45) Date of Patent: Aug. 13, 2024

(54) METHOD FOR GENERATING A GENETICALLY MODIFIED PIG WITH INACTIVATED PORCINE ENDOGENOUS RETROVIRUS (PERV) ELEMENTS

(71) Applicant: eGenesis, Inc., Cambridge, MA (US)

(72) Inventor: Luhan Yang, Brookline, MA (US)

(73) Assignee: EGENESIS, INC., Cambridge, MA (US)

( * ) Notice: Subject to any disclaimer, the term of this patent is extended or adjusted under 35 U.S.C. 154(b) by 588 days.

(21) Appl. No.: 16/607,074

(22) PCT Filed: Apr. 20, 2018

(86) PCT No.: PCT/US2018/028539
§ 371 (c)(1),
(2) Date: Oct. 21, 2019

(87) PCT Pub. No.: WO2018/195402
PCT Pub. Date: Oct. 25, 2018

(65) Prior Publication Data
US 2020/0404891 A1 Dec. 31, 2020

Related U.S. Application Data

(60) Provisional application No. 62/543,610, filed on Aug. 10, 2017, provisional application No. 62/527,702, filed on Jun. 30, 2017, provisional application No. 62/500,197, filed on May 2, 2017, provisional application No. 62/487,898, filed on Apr. 20, 2017.

(51) Int. Cl.
| | |
|---|---|
| *A01K 67/027* | (2006.01) |
| *A01K 67/0276* | (2024.01) |
| *A01K 67/0278* | (2024.01) |
| *C12N 9/22* | (2006.01) |
| *C12N 15/11* | (2006.01) |
| *C12N 15/877* | (2010.01) |

(52) U.S. Cl.
CPC ...... *A01K 67/0278* (2013.01); *A01K 67/0276* (2013.01); *C12N 9/22* (2013.01); *C12N 15/11* (2013.01); *C12N 15/111* (2013.01); *C12N 15/8778* (2013.01); *A01K 2217/072* (2013.01); *A01K 2227/108* (2013.01); *A01K 2267/02* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 6,039,784 A | 3/2000 | Luk | |
| 6,090,400 A | 7/2000 | Elliott | |
| 6,331,658 B1 | 12/2001 | Cooper et al. | |
| 6,455,037 B1 | 9/2002 | Ioannou et al. | |
| 6,534,261 B1 | 3/2003 | Cox, III et al. | |
| 6,548,741 B2 | 4/2003 | DeSousa et al. | |
| 6,586,240 B1 | 7/2003 | Singer et al. | |
| 6,867,347 B2 | 3/2005 | Patience | |
| 7,166,278 B2 | 1/2007 | Zhu | |
| 7,368,284 B2 | 5/2008 | Koike | |
| 7,485,769 B2 | 2/2009 | Murakami et al. | |
| 7,547,816 B2 | 6/2009 | Day et al. | |
| 7,795,493 B2 | 9/2010 | Phelps et al. | |
| 8,034,330 B2 | 10/2011 | Zhu | |
| 8,106,251 B2 | 1/2012 | Ayares et al. | |
| 8,142,769 B2 | 3/2012 | Elliott et al. | |
| 8,309,791 B2 | 11/2012 | Fahrenkrug et al. | |
| 8,697,359 B1 | 4/2014 | Zhang | |
| 8,785,718 B2 | 7/2014 | Fahrenkrug et al. | |
| 8,795,965 B2 | 8/2014 | Zhang | |
| 8,802,920 B2 | 8/2014 | McQuillan et al. | |
| 8,828,652 B2 | 9/2014 | Varki et al. | |
| 8,871,445 B2 | 10/2014 | Cong et al. | |
| 8,889,394 B2 | 11/2014 | Chalasani | |

(Continued)

FOREIGN PATENT DOCUMENTS

| | | |
|---|---|---|
| CA | 2534296 C | 3/2013 |
| CN | 1972593 A | 5/2007 |

(Continued)

OTHER PUBLICATIONS

Yang (Science, 2015, vol. 350, p. 1101-1104).*
Niu (Science, 2017, vol. 357, p. 1303-1307).*
Hryhorowicz (Mol. Biotechnol. 2017, vol. 59, p. 435-444).*
Hwang (Dev. Reprod., 2015, vol. 19, p. 79-84).*
Lee (Mol. Reprod. Develop., 2005, vol. 71, p. 45-51).*
Supplementary Materials for Yang (Science, 2015, vol. 350, No. 6264, p. 1101-1104.*
Chung et al. (2014). "Inhibition of porcine endogenous retrovirus in PK15 cell line by efficient multitargeting RNA interference." Transpl. Int., vol. 27, No. 1, pp. 96-105.

(Continued)

*Primary Examiner* — Michael C Wilson
(74) *Attorney, Agent, or Firm* — Wilson Sonsini Goodrich & Rosati

(57) ABSTRACT

The present disclosure provides methods of generating multiplexed genetically modified animals, for example, porcine endogenous retrovirus (PERV)-inactivated pigs. The disclosure also provides methods of improving the birth rate of multiplexed genetically modified animals. In some embodiments, the present closure is concerned with the generation and utilization of porcine cells in which porcine endogenous retroviral (PERV) elements have been inactivated. In sonic embodiments, the PERV-free or PERV-reduced porcine cells are cloned to produce porcine embryos. In some embodiments, the PERV-free or PERV-reduced embryos may be grown into adult swine from which organs and/or tissues may be extracted and used for such purposes as xenotransplantation into non-porcine animals such as humans.

30 Claims, 41 Drawing Sheets
Specification includes a Sequence Listing.

(56) References Cited

U.S. PATENT DOCUMENTS

| | | | |
|---|---|---|---|
| 8,906,616 B2 | 12/2014 | Zhang et al. |
| 8,932,814 B2 | 1/2015 | Cong et al. |
| 8,957,234 B2 | 2/2015 | Kolel-Veetil et al. |
| 8,980,579 B2 | 3/2015 | Mauro et al. |
| 8,993,233 B2 | 3/2015 | Zhang et al. |
| 8,999,641 B2 | 4/2015 | Zhang et al. |
| 9,023,649 B2 | 5/2015 | Mali et al. |
| 9,090,708 B2 | 7/2015 | Lechler et al. |
| 9,260,723 B2 | 2/2016 | Mali et al. |
| 9,267,135 B2 | 2/2016 | Church et al. |
| 9,339,519 B2 | 5/2016 | Ayares |
| 9,420,770 B2 | 8/2016 | Tector et al. |
| 9,585,374 B2 | 3/2017 | Wells et al. |
| 9,587,252 B2 | 3/2017 | Church et al. |
| 9,642,899 B2 | 5/2017 | McGregor et al. |
| 9,888,674 B2 | 2/2018 | Tector |
| 9,889,207 B2 | 2/2018 | Howard |
| 9,970,024 B2 | 5/2018 | Church et al. |
| 9,999,641 B2 | 6/2018 | Schneider et al. |
| 10,130,737 B2 | 11/2018 | Ayares et al. |
| 10,183,978 B2* | 1/2019 | Rogers | A01K 67/0276 |
| 10,266,850 B2 | 4/2019 | Doudna et al. |
| 10,273,501 B2 | 4/2019 | Church et al. |
| 10,300,112 B2 | 5/2019 | Ayares |
| 10,329,587 B2 | 6/2019 | Church et al. |
| 10,375,938 B2 | 8/2019 | Church et al. |
| 10,383,317 B2 | 8/2019 | Ayares |
| 10,435,708 B2 | 10/2019 | Mali et al. |
| 10,526,618 B2 | 1/2020 | Esvelt et al. |
| 10,563,225 B2 | 2/2020 | Church et al. |
| 10,640,789 B2 | 5/2020 | Church et al. |
| 10,667,500 B2 | 6/2020 | Tector |
| 10,717,990 B2 | 7/2020 | Mali et al. |
| 10,736,903 B2 | 8/2020 | Van Berkel et al. |
| 10,767,194 B2 | 9/2020 | Church et al. |
| 10,787,684 B2 | 9/2020 | Byrne et al. |
| 10,799,614 B2 | 10/2020 | Holzer et al. |
| 10,851,380 B2 | 12/2020 | Kim et al. |
| 10,925,263 B2 | 2/2021 | Church et al. |
| 10,959,413 B2 | 3/2021 | Church et al. |
| 10,968,276 B2 | 4/2021 | Moore et al. |
| 11,064,684 B2 | 7/2021 | Church et al. |
| 11,236,359 B2 | 2/2022 | Mali et al. |
| 11,359,211 B2 | 6/2022 | Church et al. |
| 11,365,429 B2 | 6/2022 | Church et al. |
| 11,459,585 B2 | 10/2022 | Church et al. |
| 11,512,325 B2 | 11/2022 | Church et al. |
| 11,535,863 B2 | 12/2022 | Church et al. |
| 11,746,349 B2 | 9/2023 | Church et al. |
| 2002/0010948 A1 | 1/2002 | Patience |
| 2003/0082559 A1 | 5/2003 | Beach et al. |
| 2003/0149254 A1 | 8/2003 | Anderson et al. |
| 2005/0090046 A1 | 4/2005 | So |
| 2005/0177882 A1* | 8/2005 | Gavin | C12N 15/877 |
| | | | 800/15 |
| 2005/0216964 A1 | 9/2005 | Patience |
| 2005/0220796 A1 | 10/2005 | Dynan et al. |
| 2005/0233994 A1 | 10/2005 | Kaykas et al. |
| 2005/0266561 A1 | 12/2005 | Wells |
| 2006/0107337 A1 | 5/2006 | Cui et al. |
| 2007/0020725 A1 | 1/2007 | Simmons et al. |
| 2009/0220455 A1 | 9/2009 | Chilkoti |
| 2010/0076057 A1 | 3/2010 | Sontheimer et al. |
| 2010/0093617 A1 | 4/2010 | Barrangou et al. |
| 2011/0059502 A1 | 3/2011 | Chalasani |
| 2011/0145940 A1 | 6/2011 | Voytas et al. |
| 2011/0189776 A1 | 8/2011 | Terns et al. |
| 2011/0223638 A1 | 9/2011 | Wiedenheft et al. |
| 2011/0301073 A1 | 12/2011 | Gregory et al. |
| 2011/0301341 A1 | 12/2011 | Zhu |
| 2012/0025518 A1 | 2/2012 | Kuranishi et al. |
| 2012/0060230 A1 | 3/2012 | Collingwood et al. |
| 2012/0191082 A1 | 7/2012 | Markowitz |
| 2013/0130248 A1 | 5/2013 | Haurwitz et al. |
| 2013/0253040 A1 | 9/2013 | Miller et al. |
| 2014/0017215 A1 | 1/2014 | Ayares |
| 2014/0068797 A1 | 3/2014 | Doudna et al. |
| 2014/0179006 A1 | 6/2014 | Zhang |
| 2014/0179770 A1 | 6/2014 | Zhang et al. |
| 2014/0242699 A1 | 8/2014 | Zhang |
| 2014/0256046 A1 | 9/2014 | Zhang et al. |
| 2014/0310830 A1 | 10/2014 | Zhang et al. |
| 2014/0315985 A1 | 10/2014 | May et al. |
| 2014/0335620 A1 | 11/2014 | Zhang et al. |
| 2014/0342456 A1 | 11/2014 | Mali et al. |
| 2014/0342457 A1 | 11/2014 | Mali et al. |
| 2015/0031132 A1 | 1/2015 | Church et al. |
| 2015/0031133 A1 | 1/2015 | Church et al. |
| 2015/0166969 A1 | 6/2015 | Takeuchi et al. |
| 2015/0232833 A1 | 8/2015 | Mali et al. |
| 2015/0247150 A1 | 9/2015 | Zhang et al. |
| 2015/0259704 A1 | 9/2015 | Church et al. |
| 2015/0284727 A1 | 10/2015 | Kim et al. |
| 2015/0291965 A1 | 10/2015 | Zhang et al. |
| 2015/0322457 A1 | 11/2015 | Kim et al. |
| 2016/0002670 A1 | 1/2016 | Church et al. |
| 2016/0017366 A1 | 1/2016 | Chen et al. |
| 2016/0153006 A1 | 6/2016 | Zhang et al. |
| 2016/0160210 A1 | 6/2016 | Mali et al. |
| 2016/0201089 A1 | 7/2016 | Gersbach et al. |
| 2016/0208243 A1 | 7/2016 | Zhang et al. |
| 2016/0237456 A1 | 8/2016 | Church et al. |
| 2016/0278350 A1 | 9/2016 | Ayares |
| 2016/0298134 A1 | 10/2016 | Chen et al. |
| 2016/0340662 A1 | 11/2016 | Zhang et al. |
| 2016/0355795 A1 | 12/2016 | Ran et al. |
| 2016/0355806 A1 | 12/2016 | Lee et al. |
| 2017/0191078 A1 | 7/2017 | Zhang et al. |
| 2017/0191082 A1 | 7/2017 | Chen et al. |
| 2017/0311579 A1 | 11/2017 | Tector |
| 2018/0073019 A1 | 3/2018 | Khalili |
| 2018/0153146 A1 | 6/2018 | Tector |
| 2018/0235194 A1 | 8/2018 | Fahrenkrug et al. |
| 2018/0249688 A1 | 9/2018 | Ayares et al. |
| 2018/0265848 A1 | 9/2018 | Kariko et al. |
| 2019/0076479 A1 | 3/2019 | Lin |
| 2019/0083542 A1 | 3/2019 | Lin |
| 2020/0228810 A1 | 7/2020 | Batard |
| 2020/0277631 A1 | 9/2020 | Doudna et al. |
| 2020/0299732 A1 | 9/2020 | Church et al. |
| 2020/0308599 A1 | 10/2020 | Church et al. |
| 2021/0100225 A1 | 4/2021 | Church et al. |
| 2021/0222193 A1 | 7/2021 | Church et al. |
| 2022/0267805 A1 | 8/2022 | Yang et al. |
| 2023/0131972 A1 | 4/2023 | Church et al. |
| 2023/0295653 A1 | 9/2023 | Church et al. |

FOREIGN PATENT DOCUMENTS

| | | |
|---|---|---|
| CN | 101160044 A | 4/2008 |
| CN | 102548394 | 7/2012 |
| CN | 103397019 A | 11/2013 |
| CN | 105154471 | 12/2015 |
| CN | 107249318 | 10/2017 |
| CN | 108486152 | 9/2018 |
| CN | 110373389 A | 10/2019 |
| EP | 1582591 | 10/2005 |
| EP | 2077329 A1 | 7/2009 |
| JP | 2007501626 A | 2/2007 |
| JP | 2009136298 A | 6/2009 |
| JP | 2011207893 A | 10/2011 |
| JP | 2016500003 A | 1/2016 |
| JP | 2016502840 A | 2/2016 |
| JP | 2016504026 A | 2/2016 |
| JP | 2018518438 | 7/2018 |
| JP | 2018530336 A | 10/2018 |
| JP | 2021097693 A | 7/2021 |
| JP | 7059468 | 4/2022 |
| WO | WO-1995/028412 | 10/1995 |
| WO | WO-1997/041863 | 11/1997 |
| WO | WO-1999/003336 | 1/1999 |
| WO | WO-1999/057266 | 11/1999 |
| WO | WO-2001/093908 | 12/2001 |
| WO | WO-0192337 A2 | 12/2001 |

(56) References Cited

FOREIGN PATENT DOCUMENTS

| WO | WO-2002/032437 | | 4/2002 |
|---|---|---|---|
| WO | WO-2002/083838 | | 10/2002 |
| WO | WO-2002/086060 | | 10/2002 |
| WO | WO-2003/002746 | | 1/2003 |
| WO | WO-2003/055302 | | 7/2003 |
| WO | WO-2004/016742 | | 2/2004 |
| WO | WO-2006/110054 | | 10/2006 |
| WO | WO-2007/033221 | | 3/2007 |
| WO | WO-2007/053565 | | 5/2007 |
| WO | WO-2008108989 | A2 | 9/2008 |
| WO | WO-2010/051288 | | 5/2010 |
| WO | WO-2010054108 | A2 | 5/2010 |
| WO | WO-2011/020120 | | 2/2011 |
| WO | WO-2011020120 | A2 | 2/2011 |
| WO | WO-2011/068798 | | 6/2011 |
| WO | WO-2011/139488 | | 11/2011 |
| WO | WO-2011143124 | A2 | 11/2011 |
| WO | WO-2011146121 | A1 | 11/2011 |
| WO | WO-2012/112586 | | 8/2012 |
| WO | WO-2012164565 | A1 | 12/2012 |
| WO | WO-2013098244 | A1 | 7/2013 |
| WO | WO-2013126794 | A1 | 8/2013 |
| WO | WO-2013141680 | A1 | 9/2013 |
| WO | WO-2013142578 | A1 | 9/2013 |
| WO | WO-2013/148049 | | 10/2013 |
| WO | WO-2013/169929 | | 11/2013 |
| WO | WO-2013/176772 | | 11/2013 |
| WO | WO-2013/188358 | | 12/2013 |
| WO | WO-2014022702 | A2 | 2/2014 |
| WO | WO-2014/065596 | | 5/2014 |
| WO | WO-2014/066505 | | 5/2014 |
| WO | WO-2014/093595 | | 6/2014 |
| WO | WO-2014/093622 | | 6/2014 |
| WO | WO-2014/093635 | | 6/2014 |
| WO | WO-2014/093655 | | 6/2014 |
| WO | WO-2014/093661 | | 6/2014 |
| WO | WO-2014/093694 | | 6/2014 |
| WO | WO-2014/093701 | | 6/2014 |
| WO | WO-2014/099744 | | 6/2014 |
| WO | WO-2014/099750 | | 6/2014 |
| WO | WO-2014089290 | A1 | 6/2014 |
| WO | WO-2014093712 | A1 | 6/2014 |
| WO | WO-2014093718 | A1 | 6/2014 |
| WO | WO-2014/138188 | | 9/2014 |
| WO | WO-2015/006290 | | 1/2015 |
| WO | WO-2015/013583 | | 1/2015 |
| WO | WO-2015/031775 | | 3/2015 |
| WO | WO-2015/089465 | | 6/2015 |
| WO | WO-2016/065046 | | 4/2016 |
| WO | WO-2016/094679 | | 6/2016 |
| WO | WO-2016/154299 | | 9/2016 |
| WO | WO-2016/187904 | | 12/2016 |
| WO | WO-2016/197357 | | 12/2016 |
| WO | WO-2016/197362 | | 12/2016 |
| WO | WO-2016/205711 | | 12/2016 |
| WO | WO-2016/210280 | | 12/2016 |
| WO | WO-2017/044864 | | 3/2017 |
| WO | WO-2017/062723 | | 4/2017 |
| WO | WO-2018/144546 | | 8/2018 |
| WO | WO-2018/156824 | | 8/2018 |
| WO | WO-2018/195402 | | 10/2018 |
| WO | WO-2020/228039 | | 11/2020 |
| WO | WO-2020/228043 | | 11/2020 |
| WO | WO 2020/228810 | | 11/2020 |
| WO | WO-2021/072777 | | 4/2021 |
| WO | WO-2021/072778 | | 4/2021 |
| WO | WO-2021139722 | A1 | 7/2021 |
| WO | WO-2022/104155 | | 5/2022 |

OTHER PUBLICATIONS

Hryhorowicz et al. (2017). "Genetically Modified Pigs as Organ Donors for Xenotransplantation." Mol Biotechnol. 59(9): 435-444. doi: 10.1007/s12033-017-0024-9.

Li et al. (2013). "Knockdown of Porcine Endogenous Retroviruses by RNA Interference in Chinese Experimental Miniature Pig Fibroblasts." Transplantation Proceedings, vol. 45, No. 2, pp. 748-755.

Kemter et al. (2018). "Will genetic engineering carry xenotransplantation of pig islets to the clinic?. " Current Diabetes Reports. vol. 18, No. 11, pp. 1-12.

Fishman. (2020). "Prevention of infection in xenotransplantation: Designated pathogen-free swine in the safety equation." Xenotransplantation. 27: e12595. https://doi.org/10.1111/xen.12595.

Guell et al. (2017). "PERV inactivation is necessary to guarantee absence of pig-to-patient PERVs transmission in xenotransplantation." Xenotransplantation. 24: e12366. https://doi.org/10.1111/xen.12366.

McGregor et al. (2018). "PERVading strategies and infectious risk for clinical xenotransplantation." Xenotransplantation. 25:e12402. Retrieved from https://doi.org/10.1111/xen.12402.

Borner et al. (2014). Human Gene therapy, vol. 25, No. 11, pp. A24, Abstract No. OR001.

Butler et al. (2015). "Recent advances in genome editing and creation of genetically modified pigs," International Journal of Surgery, vol. 23, Pt. B, pp. 217-222.

Cong et al. (2013). "Multiplex genome engineering using CRISPR/Cas systems." Science. 339(6121): 819-23.

Cooper et al. (2013). "The potential of genetically-engineered pigs in providing an alternative source of organs and cells for transplantation." Journal of Biomedical Research. 27(4): 249.

Cooper et al. (2016). "The role of genetically engineered pigs in xenotransplantation research." The Journal of pathology. 238(2): 288-99.

Denner. (2015). "Elimination of porcine endogenous retroviruses from pig cells." Xenotransplantation, pp. 411-412.

Dicarlo et al. (2013). "Genome engineering in *Saccharomyces cerevisiae* using CRISPR-Cas systems." Nucleic acids research. 41(7): 4336-43.

Dieckhoff et al. (2008). "Knockdown of porcine endogenous retrovirus (PERV) expression by PERV-specific sh RNA in transgenic pigs." Xenotransplantation. vol. 15 No. 1: pp. 36-45.

Dunn et al. (2015). "Genetic modification of porcine endogenous retrovirus (PERV) sequences in cultured pig cells as a model for decreasing infectious risk in xenotransplantation." The FASEB Journal. (1_supplement):LB761.

Ericsson et al. (2001). Journal of Virology, vol. 75, No. 6, pp. 2765-2770.

Estrada et al. (2015). "Evaluation of human and non ?human primate antibody binding to pig cells lacking GGTA 1/CMAH/β4Gal NT 2 genes." Xenotransplantation. 22(3):194-202.

Fang et al. (2012). "The sequence and analysis of a Chinese pig genome." GigaScience. vol. 1, No. 1, pp. 1-11.

Kaminski et al. (2015). Journal of the International AIDS Society, vol. 18, Supp. Suppl. 4, pp. 33, Abstract No. TUAA0203.

Karlas et al. (2004). "Inhibition of porcine endogenous retroviruses by RNA interference: increasing the safety of xenotransplantation." Virology. 325(1): 18-23.

Klymiuk et al. (2006). "Phylogeny, recombination and expression of porcine endogenous retrovirus γ2 nucleotide sequences." Journal of general virology. 87(4):977-86.

Leberfinger et al. (2019). "Bioprinting functional tissues." Acta Biomaterialia. 95:32-49.

Mali et al. (2013). "RNA-guided human genome engineering via Cas9." Science. 339(6121): 823-6.

Niu et al. (2017). "Inactivation of porcine endogenous retrovirus in pigs using CRISPR-Cas9." Science. 357: 1303-1307.

Park et al. (2018). "Tissue engineering and regenerative medicine 2017: a year in review." Tissue Engineering Part B: Reviews. 24(5): 327-44.

PCT/CN2019/087310, International Search Report and Written Opinion dated May 8, 2020, 16 pages.

PCT/CN2019/087314, International Search Report and Written Opinion dated Feb. 2, 2020, 14 pages.

PCT/CN2019/112038, International Search Report and Written Opinion dated Jul. 21, 2020, 12 pages.

PCT/CN2019/112039, International Search Report and Written Opinion dated Jul. 21, 2020, 12 pages.

(56) References Cited

OTHER PUBLICATIONS

PCT/CN2020/090440, International Search Report and Written Opinion dated Aug. 19, 2020, 16 pages.
PCT/US2013/075317, International Search Report and Written Opinion dated Apr. 15, 2014, 7 pages.
PCT/US2013/075326, International Search Report and Written Opinion dated Aug. 22, 2014, 12 pages.
PCT/US2014/045691, International Search Report and Written Opinion dated Nov. 7, 2014, 7 pages.
PCT/US2014/048140, International Search Report and Written Opinion dated Jan. 23, 2015, 15 pages.
PCT/US2016/055916, International Search Report and Written Opinion dated Dec. 30, 2016, 10 pages.
PCT/US2018/016152, International Search Report and Written Opinion dated Jun. 21, 2018, 13 pages.
PCT/US2018/019313, International Search Report and Written Opinion dated May 30, 2018, 14 pages.
PCT/US2018/028539, International Search Report and Written Opinion dated Jul. 9, 2018, 14 pages.
Ramakrishnan et al. (2018). "The Adipose Stromal Vascular Fraction as a Complex Cellular Source for Tissue Engineering Applications." Tissue Engineering, Part B, vol. 4, No. 4, p. 289-299.
Semaan et al. (2012). "Long?term effects of PERV?specific RNA interference in transgenic pigs." Xenotransplantation. 19(2): 112-21.
Semaan et al. (2015). "Cytotoxic effects during knock out of multiple porcine endogenous retrovirus (PERV) sequences in the pig genome by zinc finger nucleases (ZFN)." PLoS One. 10(4): e0122059.
Third Party Observation filed in PCT/US2016/055916 on Feb. 7, 2018.
Weiss et al. (2009). "HLA-E/human ?2-microglobulin transgenic pigs: protection against xenogeneic human anti-pig natural killer cell cytotoxicity." Transplantation. 87(1):35-43.
Yang et al. (2015). "Genome-wide inactivation of porcine endogenous retroviruses (PERVs)." Science. vol. 350, No. 6264, pp. 1101-1104.
Zhang et al. (2018). Cold Spring Harbor Perspectives in Medicine, 8: a025718, p. 1-15.
Zou et al. (2020). "Selective germline genome edited pigs and their long immune tolerance in Non-Human Primates." bioRxiv preprint doi: https://doi.org/10.1101/2020.01.20.912105.
Denner. (2016). "How Active Are Porcine Endogenous Retroviruses (PERVs)?" Viruses 2016, 8, 215; doi:10.3390/v8080215.
PCT/CN2019/112038, International Preliminary Report on Patentability dated Apr. 19, 2022, 5 pages.
PCT/CN2020/090440, International Preliminary Report on Patentability dated Nov. 16, 2021, 7 pages.
PCT/US2018/028539, International Preliminary Report on Patentability dated Oct. 22, 2019, 11 pages.
PCT/US2021/059265, International Search Report and Written Opinion dated Apr. 1, 2022, 21 pages.
Ahlborg, H.G. et al., "Bone Loss and Bone Size after Menopause," N Engl J Med., 2003;349(4):327-334.
Aigner et al., "Transgenic pigs as models for translational biomedical research." J. Mol. Med., 2010;88:653-664.
Angstrom et al., "Structural characterization of alpha1,3-galactosyltransferase knockout pig heart and kidney glycolipids and their reactivity with human and baboon antibodies," Xenotransplantation, 2010;17:48-60.
Araki et al., "Comparative analysis of right element mutant lox sites on recombination efficiency in embryonic stem cells." BMC Biotechnology, 2010;10:29.
Araki et al., "Targeted integration of DNA using mutant lox sites in embryonic stem cells." Nucleic Acids Res., 1997;25:868-872.
Armstrong, J.A. et al., "C-type Virus Particles in Pig Kidney Cell Lines," J Gen Virol., 1971;10(2):195-198.
Baertschiger, R.M. et al., "Absence of humoral and cellular alloreactivity in baboons sensitized to pig antigens," Xenotransplantation, 2004;11(1):27-32.

Belsham et al., "A region of the 5' noncoding region of foot-and-mouth disease virus RNA directs efficient internal initiation of protein synthesis within cells: involvement with the role of L protease in translational control." J Virol, 1990;64:5389-5395.
Buermann et al., "Pigs expressing the human inhibitory ligand PD-L1 (CD 274) provide a new source of xenogeneic cells and tissues with low immunogenic properties." Xenotransplantation, 2018;25(5): e12387.
Burlak et al., "N-linked glycan profiling of GGTA 1/CMAH knock-out pigs identifies new potential carbohydrate xenoantigens." Xenotransplantation, 2013;20(5):277-291.
Byrne et al., "B4GALNT2 and xenotransplantation: A newly appreciated xenogeneic antigen." Xenotransplantation, 2013;e12394.
Byrne, G.W. et al., "Cloning and expression of porcine b1,4 N-acetylgalactosaminyl transferase encoding a new xenoreactive antigen," Xenotransplantation, 2014;21(6):543-554.
Campbell et al., "Sheep cloned by nuclear transfer from a cultured cell line." Nature, 1996;380:64-66.
Chen et al., "Inhibition of intravascular thrombosis in murine endotoxemia by targeted expression of hirudin and tissue factor pathway inhibitor analogs to activated endothelium." Blood, 2004; 104:1344-1349.
Chui et al., "Alpha-Mannosidase-II Deficiency Results in Dyserythropoiesis and Unveils an Alternate Pathway in Oligosaccharide Biosynthesis." Cell, 1997;90:157-167.
Chui et al., "Genetic remodeling of protein glycosylation in vivo induces autoimmune disease." PNAS, 2001;98(3):1142-1147.
Chung, J.H. et al., "Characterization of the chicken beta-globin insulator", PNAS, 1997;94(2):575-80.
Cibelli, J.B. et al., "Cloned transgenic calves produced from nonquiescent fetal fibroblasts," Science, 1998;280(5367):1256-1258.
Clemenceau, B. et al., "Microchimerism and transmission of porcine endogenous retrovirus from a pig cell line or specific pathogen-free pig islets to mouse tissues and human cells during xenografts in nude mice," Diabetologia, 2002;45(6):914-923.
Cooper, D.K.C. et al., "Alloantibody and xenoantibody cross-reactivity in transplantation," Transplantation, 2004;77(1):1-5.
Cooper, D.K.C. et al., "Immunobiological Barriers to Xenotransplantation," Int J Surg., 2015;23(Pt B):211-216.
Cooper et al., "Progress in Pig-To-Nonhuman Primate Transplantation Models (1998-2013): A Comprehensive Review of the Literature." Xenotransplantation, 2014;21(5):397-419.
Cowan, P.J. et al., "Kidney Xenotransplantation," Kidney Int., 2014;85(2):265-275.
Crew et al., "An HLA-E single chain trimer inhibits human NK cell reactivity towards porcine cells." Molecular Immunology, 2005;42:1205-1214.
Dall'Olio et al., "The expanding roles of the Sda/Cad carbohydrate antigen and its cognate glycosyltransferase B4GALNT2." Biochimica et Biophysica Acta (BBA)-General Subjects. 2014;1840(1):443-53.
Davis, A.E. et al., "Changes in geographic disparity in kidney transplantation since the final rule," Transplantation, 2014;98(9):931-936.
Donati-Bourne, J. et al., "Donor-Recipient Size Mismatch in Paediatric Renal Transplantation," J Transplant, 2014;204:317574.
Ekser, B. et al., "Progress toward clinical xenotransplantation," Int J Surg., 2015;23(Pt B): 197-198.
FDA Guidance for Industry: Gene Therapy Clinical Trials—Observing Subjects for Delayed Adverse Events (Nov. 2006).
FDA Guidance for Industry: Source Animal, Product, Preclinical, and Clinical Issues Concerning the Use of Xenotransplantation Products in Humans (Apr. 2003, revised Dec. 2016).
FDA Guidance: Preclinical Assessment of Investigational Cellular and Gene Therapy Products (Nov. 2013).
Fiebig, U. et al., "Neutralizing antibodies against conserved domains of p15E of porcine endogenous retroviruses: basis for a vaccine for xenotransplantation?" Virology, 2003;307(2):406-413.
Fischer, K. et al., "Efficient production of multi-modified pigs for xenotransplantation by 'combineering', gene stacking and gene editing," Sci Rep., 2016;6:29081.
Gardiner-Garden, M. et al., "CpG islands in vertebrate genomes," J Mol Bio., 1987;196(2):261-82.

(56) References Cited

OTHER PUBLICATIONS

Gourishankar, S. et al., "The Stability of the Glomerular Filtration Rate after Renal Transplantation Is Improving," J Am Soc Nephrol., 2003;14(9):2387-2394.
Grams, M.E. et al., "Recipient age and time spent hospitalized in the year before and after kidney transplantation," Transplantation, 2012;94(7):750-756.
Haberle, V. et al., "Eukaryotic core promoters and the functional basis of transcription initiation," Nat Rev Mol Cell Biol., 2018;19(10): 621-637.
Hai et al., "One-step generation of knockout pigs by zygote injection of CRISPR/Cas system." Cell Research, 2014;24:372-375.
Higginbotham, L. et al., "Pre-transplant antibody screening and anti-CD154 costimulation blockade promote long-term xenograft survival in a pig-to-primate kidney transplant model," Xenotransplantation, 2015;22(3):221-230.
Hotta et al., "Long-term nonhuman primate renal allograft survival without ongoing immunosuppression in recipients of delayed donor bone marrow transplantation." Transplantation, 2018;102(4):e128-e136.
Hsu, P.D. et al., "Development and Applications of CRISPR-Cas9 for Genome Engineering," Cell, 2014;157(6):1262-1278.
Ide, K. et al., "Role for CD47-SIRPα signaling in xenograft rejection by macrophages," PNAS, 2007;104:5062-5066.
International Preliminary Report on Patentability issued in PCT/US2021/059265, dated May 16, 2023.
International Search Report and Written Opinion issued in PCT/US2021/059265, mailed Apr. 1, 2022.
Iwase, H. et al., "Current status of pig kidney xenotransplantation," Int J Surg., 2015;23(Pt B):229-233.
Iwase, H. et al., "Pig kidney graft survival in a baboon for 136 days: longest life-supporting organ graft survival to date," Xenotransplantation, 2015;22(4):302-309.
Kasiske, B.L. et al., "A simple tool to predict outcomes after kidney transplant," Am J Kidney Dis., 2010;56(5):947-960.
Kaufman et al., "Improved vectors for stable expression of foreign genes in mammalian cells by use of the untranslated leader sequence from EMC virus." Nucleic Acids Res., 1991;19:4485-4490.
Kim, E. et al., "An Improved System for Generation of Diploid Cloned Porcine Embryos Using Induced Pluripotent Stem Cells Synchronized to Metaphase," PLoS One, 2016;11(7):e0160289.
Kim et al., "High Cleavage Efficiency of a 2A Peptide Derived from Porcine Teschovirus 1 in Human Cell Lines, Zebrafish and Mice," PLoS One, 2011;6(4):e18556.
Kim et al., "Long-Term Survival of Pig-to-Rhesus Macaque Renal Xenografts is Dependent on CD4 T cell Depletion." Am J Transplant, 2019;19(8):2174-2185.
Kim, S. et al., "Highly efficient RNA-guided genome editing in human cells via delivery of purified Cas9 ribonucleoproteins," Genome Res., 2014;24(6):1012-1019.
Kim, W.R. et al., "OPTN/SRTR 2015 Annual Data Report: Liver," Am J Transplant., 2017;17 Suppl 1:174-251.
Lai, L. et al., "Production of alpha-1,3-galactosyltransferase knockout pigs by nuclear transfer cloning," Science, 2002;295(5557):1089-1092.
Larsen, C., et al., "Rational development of LEA29Y a High-Affinity Variant of CTLA4-Ig with Potent Immunosuppressive Properties," Am. I Transplant, 2005;5:443-453.
Lee, D. et al., "Rapid Determination of Perv Copy Number From Porcine Genomic DNA by Real-Time Polymerase Chain Reaction," Anim Biotechnol., 2011;22(4):175-180.
Lee et al., "Complete humanization of the mouse immunoglobulin loci enables efficient therapeutic antibody discovery." Nat Biotechnol., 2014;32:356-363.
Levey, A.S. et al., "The definition, classification, and prognosis of chronic kidney disease: a KDIGO Controversies Conference report," Kidney International, 2011;80(1):17-28.
Levitt, "Definition of an efficient synthetic poly(A) site", Genes & Development, 1989;3:1019-1025.
Lilienfeld, B.G. et al., "Transgenic expression of HLA-E single chain trimer protects porcine endothelial cells against human natural killer cell-mediated cytotoxicity," Xenotransplantation, 2007;14(2):126-134.
Liu, Z. et al., "Systematic comparison of 2A peptides for cloning multi-genes in a polycistronic vector," Scientific Reports, 2017;7(2193).
Loveland, B.E. et al., "Characterization of a CD46 transgenic pig and protection of transgenic kidneys against hyperacute rejection in non-immunosuppressed baboons," Xenotransplantation, 2009;11(2):171-183.
Lutz, A.J. et al., "Double knockout pigs deficient in N-glycolylneuraminic acid and galactose α-1,3-galactose reduce the humoral barrier to xenotransplantation," Xenotransplantation, 2013;20(1):27-35.
Maizels, N., "Genome Engineering with Cre-IoxP," J Immunol., 2013;191(1).
Marcen, R. et al., "Long-term graft function changes in kidney transplant recipients," NDT Plus, 2010;3(Suppl_2):ii2-ii8.
Martens, G.R. et al., "Humoral Reactivity of Renal Transplant-Waitlisted Patients to Cells From GGTA1/CMAH/B4GalNT2, and SLA Class I Knockout Pigs," Transplantation, 2017;101(4):e86-e92.
McGregor, C.G.A. et al., "Human CD55 expression blocks hyperacute rejection and restricts complement activation in Gal knockout cardiac xenografts," Transplantation, 2012;93(7):686-692.
Merry et al., "Glycoscience finally comes of age." EMBO reports, 2005;6(10):900-903.
Moalic, Y. et al., "Porcine Endogenous Retrovirus Integration Sites in the Human Genome: Features in Common with Those of Murine Leukemia Virus," J Virol., 2006;80(22):10980-10988.
Mohiuddin, M.M. et al., "Chimeric 2010R4 anti-CD40 antibody therapy is critical for long-term survival of GTKO.hCD46.hTBM pig-to-primate cardiac xenograft," Nat Commun., 2016;7:11138.
Mohlke et al., "Mvwf, a dominant modifier of murine von Willebrand factor, results from altered lineage-specific expression of a glycosyltransferase." Cell, 1999;96:111-120.
Mulder et al., "Human CD46 aberrant splicing in transgenic mice." Gene, 1997;186:83-86.
Muller-Kuller et al., "A minimal ubiquitous chromatin opening element (UCOE) effectively prevents silencing of juxtaposed heterologous promoters by epigenetic remodeling in multipotent and pluripotent stem cells." Nucleic Acids Research, 2015;43:1577-1592.
Neville, J.J. et al., "Ubiquitous Chromatin-opening Elements (UCOEs): Applications in biomanufacturing and gene therapy," Biotechnology Advances, 2017;35:557-564.
Niwa et al., "Efficient selection for high-expression transfectants with a novel eukaryotic vector." Gene, 1991;108:193-199.
Nojima, T. et al., "Definition of RNA Polymerase II CoTC Terminator Elements in the Human Genome," Cell Reports, 2013;3(4):1080-1092.
Nonaka et al., "Determination of carbohydrate structure recognized by prostate-specific F77 monoclonal antibody through expression analysis of glycosyltransferase genes." The Journal of Biological Chemistry, 2014;289(23):16478-16486.
Ojo, A.O. et al., "The impact of simultaneous pancreas-kidney transplantation on long-term patient survival," Transplantation, 2001;71(1):82-90.
Patience, C. et al., "Infection of human cells by an endogenous retrovirus of pigs," Nat Med., 1997;3(3):282-286.
Patience, C. et al., "Multiple Groups of Novel Retroviral Genomes in Pigs and Related Species," J Virol., 2001;75(6):2771-2775.
PCT/CN2021/070659, International Search Report and Written Opinion mailed Apr. 6, 2021, 10 pages.
Pelletier et al., "Internal initiation of translation of eukaryotic mRNA directed by a sequence derived from poliovirus RNA." Nature, 1988;334:320-325.
Pinheiro, L.B. et al., "Evaluation of a droplet digital polymerase chain reaction format for DNA copy number quantification," Anal Chem., 2012;84(2):1003-1011.
Ramsoondar, J. et al., "Production of transgenic pigs that express porcine endogenous retrovirus small interfering RNAs," Xenotransplantation, 2009;16(3):164-180.

(56) References Cited

OTHER PUBLICATIONS

Reyes, L.M. et al., "Creating class I MHC-null pigs using guide RNA and the Cas9 endonuclease," J Immunol., 2014;193(11):5751-5757.
Reynders et al., "How Golgi glycosylation meets and needs trafficking: the case of the COG complex." Glycobiology, 2011;21(7): 853-863.
Sato et al. (2019). "Recent advance in genome editing-based gene modification in pigs." Reproductive Biology and Technology in Animals, 2019:1-36.
Sato et al., "Direct injection of CRISPR/Cas9-related mRNA into cytoplasm of parthenogenetically activated porcine oocytes causes frequent mosaicism for indel mutations." Int. J. Mol. Sci., 2015;16:17838-17856.
Schuurman, H.J., "The International Xenotransplantation Association consensus statement on conditions for undertaking clinical trials of porcine islet products in type 1 diabetes—chapter 2: Source pigs," Xenotransplantation, 2009;16(4):215-222.
Sharma, P. et al., "Does stage-3 chronic kidney disease matter ?: A systematic literature review," British Journal of General Practice, 2010;60(575):e266-e276.
Shen, Z. et al., "Immunoregulation Effect by Overexpression of Heme Oxygenase-1 on Cardiac Xenotransplantation," Transplant Proc., 2011;43(5):1994-1997.
Starzl, T.E. et al., "Cell Migration and Chimerism After Whole-organ Transplantation: The Basis of Graft Acceptance," Hepatology, 1993;17(6):1127-1152.
Starzl, T.E. et al., "Renal Heterotransplantation From Baboon To Man: Experience With 6 Cases," Transplantation, 1964;2:752-756.
Suzuki, K. et al., "In vivo genome editing via CRISPR/Cas9 mediated homology independent targeted integration," Nature, 2016;540(7631):144-149.
Tanabe, T. et al., "Role of Intrinsic (Graft) Versus Extrinsic (Host) Factors in the Growth of Transplanted Organs Following Allogeneic and Xenogeneic Transplantation," Am J Transplant., 2017;17(7):1778-1790.
Tseng, Y. et al., "Elicited antibodies in baboons exposed to tissues from alpha 1,3-galactosyltransferase gene-knockout pigs," Transplantation, 2006;81(7):1058-1062.
Vagefi, P. et al., "Progress towards inducing tolerance of pig-to-primate xenografts," Int J Surg., 2015;23(Pt B):291-295.
Veer, C. et al., "Inhibitory Mechanism of the Protein C Pathway on Tissue Factor-induced Thrombin Generation: Synergistic Effect in Combination With Tissue Factor Pathway Inhibitor," J Biol Chem., 1997;272(12):7983-7994.
Wang et al., "Eliminating xenoantigen expression on swine RBC." Transplantation, 2017;101(3): 517-523.
Wang, Y. et al., "Efficient generation of B2m-null pigs via injection of zygote with TALENs," Sci Rep., 2016;6:38854.
Yang, L. et al., "Optimization of scarless human stem cell genome editing," Nucleic Acids Res., 2013;41(19):9049-9061.
Ye, Y. et al., "Secondary Organ Allografting After a Primary "Bridging" Xenotransplant," Transplantation, 1995;60(1):19-22.
Zhao, Z. et al., "CpG islands: algorithms and applications in methylation studies," Biochem Biophys Res Commun., 2009;382(4):643-645.
Zheng et al., "Efficient and Safe Editing of Porcine Endogenous Retrovirus Genomes by Multiple-Site Base-Editing Editor." Cells, 2022;11:3975.
Al-Attar et al., Clustered Regularly Interspaced Short Palindromic Repeats (CRISPRs): The Hallmark of an Ingenious Antiviral Defense Mechanism in Prokaryotes, Bio Chem. (2011) vol. 392, Issue 4, pp. 277-289.
Alberts et al., Molecular Biology of the Cell, Fifth Ed., 699-707 (2008).
Baker, M., Gene editing at CRISPR speed, Nature Biotechnology, 2014, vol. 32(4), pp. 309-312.
Barrangou, R. (2012). RNA-mediated programmable DNA cleavage. Nature biotechnology, 30(9), 836-838. doi:10.1038/nbt.2357.
Bassett, A.R. and Liu, J.-L., CRISPR!Cas9 and Genome Editing in Drosophila, Journal of Genetics and Genomics, 2014, vol. 41, pp. 7-19 (including supplementary materials).
Bobis-Wozowicz, et al., Targeted genome editing in pluripotent stem cells using zinc-finger nucleases, Methods, 2011, vol. 53, pp. 339-346.
Borner et al., Human Gene Therapy, vol. 25, No. 11, pp. A24, Abstract No. OR001 (2014).
Brouns, SJ Molecular biology. A Swiss army knife of immunity. Science 337(6069)808-9 (Aug. 17, 2012).
Brunet et al., Chromosomal translocations induced at specified lociin human stem cells. PNAS 106(26):10620-10625 (2009).
Buerck et al., LEA29Y expression in transgenic neonatal porcine islet-like cluster promotes long-lasting xenograft survival in humanized mice without immunosuppressive therapy, Scientific Reports, 2017;7:3572.
Campeau, E. et al., A versatile viral system for expression and depletion of proteins in mammalian cells. PLoS One 4, e6529 (2009).
Carlson et al., Targeting DNA with Fingers and TALENs. Molecular Therapy-Nucleic Acid, 1 (2012): 1-4.
Carney, J. et al., Induction of DNA Double-Strand Breaks by Electrocorporation of Restriction Enzymes into Mammalian Cells. Methods in Mol. Bioi., vol. 113, pp. 465-471 (1999).
Carroll, a CRISPR Approach to Gene Targeting 20(9) Molecular Therapy 1658-1660 (Sep. 2012).
Carroll, D. et al., Design, construction and in vitro testing of zinc finger nucleases. Nature Protocols, vol. 1(3), pp. 1329-1341 (2006).
Carroll, Progress and prospects: Zinc-finger nucleases as gene therapy agents, Gene Therapy 15: 1463-1468 (2008).
Cermak et al., Efficient design and assembly of custom TALEN and other TAL effector-based constructs for DNA targeting. Nucleic Acids Research 39(12):e82 (2011).
Chang et al., Genome editing with RNA-guided Cas9 nuclease in zebrafish embryos. Cell Res 23:465-472 (2013).
Chapdelaine, P. et al., Meganucleases can restore the reading frame of a mutated dystrophin. Gene Therapy, vol. 17, pp. 846-858 (2010).
Chen, C. et al., Transfection and expression of plasmid DNA in plant cells by an arginine-rich intracellular delivery peptide without protoplast preparation, FEBS Letters, vol. 581, pp. 1891-1897 (2007).
Cho et al., Targeted genome engineering in human cells with the Cas9 RNA-guided endonuclease. Nat Biotechnol 31(3):230-232 (2013).
Christian et al., Targeting DNA Double-Strand Breaks with TAL Effector Nucleases, Genetics 186: 157-161 (2010).
Cong et al., Comprehensive interrogation of natural TALE DNA-binding modules and transcriptional repressor domains. Nat Commun. Jul. 24, 2012;3:968. doi: 10.1038/ncomms1962.
Cooper et al., The Role of Genetically Engineered Pigs in Xenotransplantation Research. Journal of Pathology 238: 288-299 (2016).
Deltcheva, E. et al., CRISPR RNA maturation by trans-encoded small RNA and host factor RNase III, Nature, vol. 471(7340), pp. 602-607 (doi:10.1038/nature09886), plus Supplementary Material (2011).
Dominguez et al., Beyond editing: repurposing CRISPR-Cas9 for precision genome regulation and interrogation. Nat Rev Mol Cell Biol 17: 5-15 (2015).
Dunn et al., Genetic Modification of Porcine Endogenous Retrovirus (PERV) Sequences in Cultured Pig Cells as a Model for Decreasing Infectious Risk in Xenotransplantation, FASEB Journal, vol. 29, No. 1_Supplement, Abstract No. LB761. (2015).
Eggers, P.W., Mortality Rates Among Dialysis Patients in Medicare's End-Stage Renal Disease Program, Am J Kidney Dis., 1990;15(5):414-421.
Fieck, A. et al., Modifications of the *E. coli* Lac repressor for expression in eukaryotic cells: effects of nuclear signal sequences on protein activity and nuclear accumulation. Nucleic Acids Res., vol. 20{7), pp. 1785-1791 {1992).

(56) References Cited

OTHER PUBLICATIONS

Fischer-Fantuzzi, L. et a., Cell-Dependent Efficiency of Reiterated Nuclear Signals in a Mutant Simian Virus 40 Oncoprotein Targeted to the Nucleus, Molecular and Cellular Biology, vol. 8(12), pp. 5495-5503 (1988).
Fisicaro et al., Versatile Co-expression of Graft-Protective Proteins Using 2A-Linked Cassettes. Xenotransplantation 18: 121-130 (2011).
Fujii, Wataru, et al., Efficient generation of large-scale genome-modified mice using gRNA and CAS9 endonuclease. Nucleic acids research. Vol. 41, Issue No. 20 (2013): e187.
Gaj et al., Targeted gene knockout by direct delivery of zinc-finger nuclease proteins. Nat Methods, 1;9(8):805-7 (2012).
Gantz, J. et al., Targeted Genomic Integration of a Selectable Floxed Dual Fluorescence Reporter in Human Embryonic Stem Cells. PLOS One, vol. 7(10):e46971 (2012).
Gao, Z. et al., Delineation of the Exact Transcription Termination Signal for Type 3 Polymerase III, Molecular Therapy—Nucleic Acids, vol. 10, pp. 36-44, plus Supplementary Material (2018).
Gasiunas et al., Cas9-crRNA ribonucleoprotein complex mediates specific DNA cleavage for adaptive immunity in bacteria. Proc Natl Acad Sci U S A. Sep. 25, 2012; 109(39): E2579-E2586.
Gene Transfer and Expression in Mammalian Cells, Elsevier Science B.V., Table 1 (2003).
Gietz et al., High-Efficiency Yeast Transformation Using the LiAc/SS Carrier DNA/PEG Method. Nature Protocols 2:31-34 (2007).
Gilbert et al., CRISPR-Mediated modular RNA-guided regulation of transcription in Eukaryotes. Cell 154(2): 442-451 (2013).
Good et al., Expression of small, therapeutic RNAs in human cell nuclei Gene Therapy (1997) 4, pp. 45-54.
Gopalan, V. et al., RNase P. Variations and Uses*. The Journal of Biological Chemistry, vol. 277(9), pp. 6759-6762 (2002).
Gratz, S. et al., Genome engineering of Drosophila with the CRISPR RNA-guided Cas9 nuclease, Genetics, vol. 194, pp. 1029-1035, plus Supplementary Material (2013).
Groth, et al., A phage integrase directs efficient site-specific integration in human cells, PNAS, 2000, vol. 97, No. 11, paQes 5995-6000.
Gustafsson, C. et al., Codon bias and heterologous protein expression. Trends Biotech., vol. 22(7), pp. 346-353 (2004).
Hale et al., Essential Features and Rational Design of CRISPR RNAs That Function With the Cas RAMP Module Complex to Cleave RNAs, Molecular Cell, (2012) vol. 45, Issue 3, 292-302.
Handel et al., Versatile and efficient genome editing in human cells by combining zinc-finger nucleases with adeno-associated viral vectors. Human Gene Therapy. 23(3):321-329 (2012).
Hatoum-Aslan, et al., Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.
Hockemeyer, D. et al., Gene Targeting in Human Pluripotent Cells. Cold Spring Harbor Symposia for Quantitative Biology, vol. 75, pp. 201-209 (2010).
Hsu et al., Development and applications of CRISPR-Cas9 for genome engineering. Cell 157:1262-1278 (2014).
Hsu, et al., DNA targeting specificity of RNA-guided Cas9 nucleases. Nat Biotechnol. vol. 31, Issue No. 9 (2013): 827-832.
Hu, P. et al., Comparison of Various Nuclear Localization Signal-Fused Cas9 Proteins and Cas9 mRNA for Genome Editing in Zebrafish. G3, vol. 8, pp. 823-831 (2018).
Huang et al., The Flaws and Future of Islet volume Measurements. Cell Transplant 27: 1017-1026 (2018).
Hwang et al., Efficient genome editing in zebrafish using a CRISPR-Cas system. Nat. Biotechnol 31:227-229 (2013), and Supplementary Materials.
Jinek et al., A programmable dual-RNA-guided DNA endonuclease in adaptive bacterial immunity. Science 337(6096):816-821 (2012).
Jinek et al., RNA-programmed genome editing in human cells, eLife 2013;2:e00471 doi:10.7554/eLife.00471. 14 pages. Retrieved Mar. 23, 2020 from URL: https://elifesciences.org/articles/00471.
Joung et al., TALENs: a widely applicable technology for targeted genome editing. Nat Rev Mol Cell Bio 14:49-55 (2013).
Kalderon, D. et al., A Short Amino Acid Sequence Able to Specify Nuclear Location, Cell, vol. 39, pp. 499-509 (1984).
Kefeng Dou., Xenotransplantation. People's Military Medical Press 316-318 (2014).
Kim et al., Precision genome engineering with programmable DNA-nicking enzymes. Genome Res 22(7):1327-1333 (2012).
Kong et al., Genetic Characteristics of Polycistronic System-mediated Randomly-inserted Multi-transgenes in Miniature Pigs and Mice. Molecular Medicine Reports 17: 37-50 (2018).
Kuspa, A. et al., Tagging developmental genes in Dictyostelium by restriction enzyme-mediated integration of plasmid DNA. Proc. Natl. Acad. Sci. USA, vol. 89(18), pp. 8803-8807 (1992).
Kuzmine, I. et al., Binding of the priming nucleotide in the initiation of transcription by T7 RNA polymerase. J. Biol. Chem. 278(5): 2819-2823 (2003).
Lange, et al. Classical Nuclear Localization Signals: Definition, Function, and Interaction with Importin α*,s. J Biol Chem. Feb. 23, 2007; 282(8): 5101-5105.
Le Provost et al., Zinc Finger Nuclease Technology Heralds a New Era in Mammalian Transgenesis. Trends in Biotechnology, 28.3 (Mar. 2010): 134-141. Available online Dec. 16, 2009. DOI: https://doi.org/10.1016/j.tibtech.2009.11.007.
Lee, Ciaran M., et al., Correction of the DF508 Mutation in the Cystic Fibrosis Transmembrane Conductance Regulator Gene by Zinc-Finger Nuclease Homology-Directed Repair, BioResearch Open Access? Jun. 2012, vol. 1, pp. 99-108.
Lee et al., Targeted Chromosomal Deletions in Human Cells Using Zinc Finger Nucleases. Genome Research, 20 (Dec. 1, 2009): 81-89.
Lee, H. et al., Targeted chromosomal duplications and inversions in the human genome using zinc finger nucleases. 3enome Res., vol. 22, pp. 539-548 {2012}.
Lewin, B. et al., Cells, p. 224 (2007) 3 pages.
Li et al., Modularly assembled designer TAL effector nucleases for targeted gene knockout and gene replacement in eukaryotes. Nucleic Acids Res. Aug. 2011; 39(14): 6315-6325. Published online Mar. 3, 20111. doi: 10.1093/nar/gkr188.
Li et al., TAL Nucleases (TALNs): Hybrid Proteins Composed of TAL Effectors And Fokl DNA-Cleavage Domain. Nucleic Acids Research, 39.1 (Aug. 10, 2010): 359-372.
Link, K. et al., Engineering ligand-responsive gene-control elements: lessons learned from natural riboswitches. Gene Therapy, vol. 16{10}, pp. 1189-1201 {2009}.
Lipofectamine 2000 Transfection Reagent (ThermoFisher Scientific website).
Liu et al., Combinatorial RNAi Against HIV-1 Using Extended Short Hairpin RNAs, Molecular Therapy, vol. 17, No. 10, pp. 1712-1723 (2009).
Liu, P. et al., Generation of a Triple-Gene Knockout Mammalian Cell Line Using Engineered Zinc-Finger Nucleases. Biotechnol Bioeng., vol. 106(1), pp. 97-105 (2010).
Lyssenko, N. et al., Cognate putative nuclear localization signal effects strong nuclear localization of a GFP reported and facilitates gene expression studies in Caenhoghabditis elegans, Biotechniques, vol. 43, pp. 596-600 (2007).
Ma S. et al., Highly Efficient and Specific Genome Editing in Silkworm Using Costom TALENs. PLoS One, vol. 7(9), e45035 (2012).
Makarova et al., Annotation and Classification of CRISPR-Cas Systems. Method Mol Biol 1311:47-75 (2015).
Makarova et al., Evolution and classification of the CRISPR-Cas systems. Nat Rev Microbiol. 9(6):467-77 (2011).
Mali et al., Cas9 as a versatile tool for engineering biology. Nat Methods 10:957-963 (2013).
Mali et al., RNA-Guided Human Genome Engineering via Cas9. Science 339: 823-826 (2013).
Maraia, R. et al., 3' processing of eukaryotic precursor tRNAs, Wiley Interdiscip Rev RNA, vol. 2 (3), pp. 362-375 (2010).
Martin et al., Expression of pig endogenous retrovirus by primary porcine endothelial cells and infection of human cells. Lancet. 352:692-694 (1998).

(56) References Cited

OTHER PUBLICATIONS

Mastroianni, M. et al., Group II Intron-Based Gene Targeting Reactions in Eukaryotes. PLoS One, vol. 3(9), e3121 (2008).
Miller et al., A Tale nuclease architecture for efficient genome editing. Nat Biotechnol. 29.2 (Feb. 2011): 143-8. doi: 10.1038/nbt. 1755. Epub Dec. 22, 2010.
Morgan, W. et al., Inducible Expression and Cytogenetic Effects of the EcoRI Restriction Endonuclease in Chinese Hamster Ovary Cells. Molecular and Cellular Biology, vol. 8(10), pp. 4204-4211 (1988).
Nishimasu et al., Crystal Structure of Cas9 in Complex with Guide RNA and Target DNA. Cell 156(5):935-949 (2014).
Niu et al., Inactivation of porcine endogenous retrovirus in pigs using CRISPR-Cas9. Science, Published Aug. 10, 2017 on Science First Release DOI: 10.1126/science.aan4187, plus Supplementary Materials.
Perez-Pinera, P. Advances in Targeted Genome Editing. Current Opinion in Chemical Biology, 16 (3-4), 268-277 (2012).
PHcRed1 Vector Information Sheet, Clontech Laboratories, Inc. (2003).
Planey, S. et al., Mechanisms of Signal Transduction: Inhibition of Glucocorticoid-induced Apoptosis in 697 Pre-B Lymphocytes by the Mineralocorticoid Receptor N-terminal Domain. J. Bioi. Chem, vol. 277{44), pp. 42188-42196 (2002).
Porteus et al., Chimeric Nucleases and Gene Targeting GFP Gene Targeting System, Science. May 2, 2003; vol. 300 (5620):763.
Pougach et al., CRISPR Adaptive Immunity Systems of Prokaryotes, Molecular Biology, vol. 46, No. 2, pp. 175-182 (2012).
PShooter Vector User Guide, Invitrogen (2012).
Qi, L. et al., RNA Processing Enables Predictable Programming of Gene Expression, Nature Biotechnology, 2012, vol. 30(1 0), pp. 1002-1007 (including Supplementary Information).
Radulovich, N. et al., Modified gateway system for double shRNA expression and Cre/lox based gene expression. BMC Biotech. 11, 1-9 (2011).
Ramirez et al., Engineered zinc finger nickases induce homology-directed repair with reduced mutagenic effects. Nucl Acids Res 40(12):5560-5568 (2012).
Ran, Ann, et al., Genome engineering using the CRISPR-Cas9 system. Nature Protocols. Vol. 8, Issue No. 11 (2013): 2281-2308.
Raymond, C.S. and Soriano, P., High-Efficiency FLP and PhiC31 Site-Specific Recombination in Mammalian Cells, PLoS One, 2007, vol. 2(1), p. e162.
Rebar, E.J. et al., Induction of angiogenesis in a mouse model using engineered transcription factors. Nature Medicine. 8: 1427-1432 (2002).
Regaldo: Who owns the biggest biotech discover of the century ?. MIT Technology Review. 4 pages (2014).
Reiss et al., RecA protein stimulates homologous recombination in plants. Proceedings of the National Academy of Sciences, 93 (Apr. 1996): 3094-3098.
Rho, Mina et al., Diverse CRISPRs Evolving in Human Microbiomes.' PLoS Genetics. vol. 8, No. 6. 1-14 pp. 1-12. Jun. 2012. entire document.
Rhun, Anais et al., Small RNAs in streptococci, RNA Biology, Apr. 2012, vol. 9, pp. 414-426.
Robson et al., Disordered Regulation of Coagulation and Platelet Activation in Xenotransplantation. Xenotransplantation 7: 166-176 (2000).
Sanjana, N. et al., A Transcription Activator-Like Effector (TALE) Toolbox for Genome Engineering. Nat. Proto. vol. 7(1):171-192 (2011).
Sauer, Brian et al., Site-specific DNA recombination in mammalian cells by the Cre recombinase of bacteriophage P1, Proc. Natl. Acad. Sci. USA, vol. 85, pp. 5166-5170, Jul. 1988. Genetics.
Schiestl, R. et al., Integration of DNA fragments by illegitimate recombination in Saccharomyces cerevisiae. Proc. Natl. Acad. Sci. USA, vol. 88(17), pp. 7585-7589 (1991).
Schultz, J. et al., Development of a CRISPR/Cas9 system for high efficiency multiplexed gene deletion in Rhodosporidium toruloides. Biotechnology and Bioengineering, vol. 116, pp. 2103-2109 (2019).
Singer et al., Applications of Lentiviral Vectors for shRNA Delivery and Transgenesis, Curr. Gene Ther., vol. 8(6), pp. 483-488 (2008).
Sontheimer et al., Project 7: Establishing RNA-Directed DNA Targeting in Eukaryotic Cells; Project dates: Nov. 16, 2011 to Dec. 31, 2012 (Feb. 4, 2012).
Suzuki et al., In Vivo Genome Editing via CRISPR/Cas9 Mediated Homology-independent Targeted Integration. Nature 540:144-149 (2016).
Tuschl et al., Expanding small RNA interference, Nat. Biotech. 20:446-448 (2002).
Urnov, F.D., et al., Genome editing with engineered zinc finger nucleases Nature Reviews Genetics, Sep. 2010, vol. 11, pp. 636-646.
Wiedenheft et al., RNA-guided genetic silencing systems in bacteria and archaea. Nature 482:331-338 (2012).
Wieland, M. et al., Engineering of ribozyme-based riboswitches for mammalian cells. Methods, vol. 56., pp. 351-357 {2012).
Wilson et al., Mammal Species of the World: a Taxonomic and Geographic Reference. Smithsonian Institution Press. 2nd Edition 75: 239-243 (1993).
Wong et al., The ABCs of Gene Cloning, Springer Science & Business Media, 93-124 (2005).
Yamamoto et al., Old World Monkeys Are Less Than Ideal Transplantation Models for Testing Pig Organs Lacking Three Carbohydrate Antigens (Triple-knockout). Scientific Reports 10: 9771 (2020).
Zhang et al., Efficient construction of sequence-specific TAL effectors for modulating mammalian transcription. Nature Biotechnology, 29(2): 149-153; Published online Jan. 19, 2011.
Zhang et al., Programmable Sequence-Specific Transcriptional Regulation of Mammalian Genome Using Designer TAL Effectors, Nat Biotechnol. Feb. 2011; 29(2): 149-153.

\* cited by examiner

| Validated Human PERV junction sequences | Position (GRCh38.p7) | Gene | Intron/Exon |
|---|---|---|---|
| SEQ ID No. 182 GACCATTACCAAGCAGGGTCTGACAGGTACTGAAAGGATGAA | chr1:32818962-32818933 | S100PBP | intron |
| SEQ ID No. 183 ATTAAACAACTCAGCCGGGTCCAGTGCCTCTCGAAAGGATGAA | chr6:43630446-43630475 | MAD2L1BP | intron |
| SEQ ID No. 184 AACTGTATAGTCTTGGATAAACAGTTCAGGTGAAAGGATGAA | chr6:143062056-143062027 | AIG1 | intron |
| SEQ ID No. 185 CGTGGGAAACAGGGGCTCCCGCGACTGCGCTTGAAAGGATGAA | chr4:1683715-1683744 | FAM53A | intron |
| SEQ ID No. 186 GCAAATGTCTTTATTGTTTGTTGCTGGTTTGAAAGGATGAA | chr14:61764943-61764972 | SNAPC1 | intron |
| SEQ ID No. 187 GGAGTGCAGTGATCTGATCTCGCTCATGGTGAAAGGATGAA | chr18:58882490-58882519 | ZNF532 | intron |
| SEQ ID No. 188 CCGTTCCTCCCAAGGCGGGCCTTGAAAGGATGAAAGGATGAA | chr5:172984005-172983976 | ATP6V0E1 | intron |

FIGURE 1B

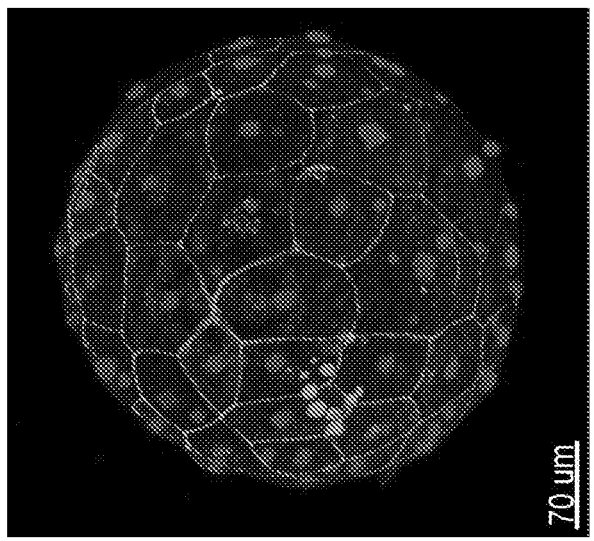
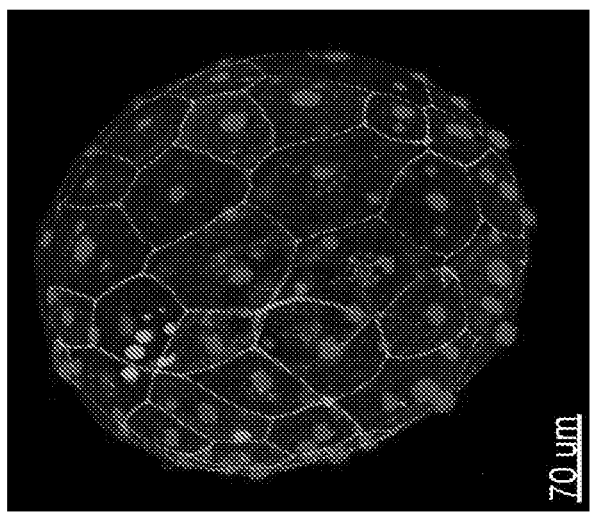
FIGURE 3A

|  | >80 PERV-ko clones/total | >90% PERV-ko clones/total |
|---|---|---|
| No large T | 2.92% | 0.83% |
| With large T | 10.94% | 4.20% |
| Folds increased | 3.75 | 5.06 |

FIGURE 6B

Primer used to detect PERV junctions in FF3CF

PERV junction primers for FF3CF (Black: 5'LTR; Red: 3'LTR)

| PERV | LTR | | Forward | | Reverse |
|---|---|---|---|---|---|
| 1 | 5' | SEQ ID No. 189 | ACTCTATCCTATAAGGTTGACA | SEQ ID No. 190 | TAGGTTGCATTTTCATCCTT |
| 14 | 5' | SEQ ID No. 191 | GGAGCAAAAGAGCAGTATG | SEQ ID No. 192 | TAGGTTGCATTTTCATCCTT |
| 15 | 5' | SEQ ID No. 193 | TATATGACGCATTCAGTTG | SEQ ID No. 194 | TAGGTTGCATTTTCATCCTT |
| 16 | 5' | SEQ ID No. 195 | TTTTCGGAGGATTTTCAGG | SEQ ID No. 196 | TAGGTTGCATTTTCATCCTT |
| 17 | 5' | SEQ ID No. 197 | TACTGCATTTGATACCACAT | SEQ ID No. 198 | TAGGTTGCATTTTCATCCTT |
| 18 | 5' | SEQ ID No. 199 | GACTTCCGTCATTTATGTAAAC | SEQ ID No. 200 | TAGGTTGCATTTTCATCCTT |
| 19 | 5' | SEQ ID No. 201 | CTCTGGTCGTTCAGTGG | SEQ ID No. 202 | TAGGTTGCATTTTCATCCTT |
| 20 | 5' | SEQ ID No. 203 | CAGATGAGTGGAGCAAGG | SEQ ID No. 204 | TAGGTTGCATTTTCATCCTT |
| 2 | 5' | SEQ ID No. 205 | GTTACTGGGTCAGGGATAA | SEQ ID No. 206 | TAGGTTGCATTTTCATCCTT |
| 3 | 5' | SEQ ID No. 207 | CCCTCCATATACATTTTCTCTA | SEQ ID No. 208 | TAGGTTGCATTTTCATCCTT |
| 4 | 5' | SEQ ID No. 209 | GAGTCCCATTCACCAAGT | SEQ ID No. 210 | TAGGTTGCATTTTCATCCTT |
| 5 | 3' | SEQ ID No. 211 | ACGCACAAGACAAAGACA | SEQ ID No. 212 | CTCCCACCCAGTTTCATAG |
| 6 | 5' | SEQ ID No. 213 | CCCGCAAATCTCAGGAG | SEQ ID No. 214 | TAGGTTGCATTTTCATCCTT |
| 7 | 5' | SEQ ID No. 215 | GTTTGACAGTGGTGTTGT | SEQ ID No. 216 | TAGGTTGCATTTTCATCCTT |
| 8 | 5' | SEQ ID No. 217 | TGTTGAGACAATAGGGTGAT | SEQ ID No. 218 | TAGGTTGCATTTTCATCCTT |
| 9 | 5' | SEQ ID No. 219 | TCATGAACAAGTGCTGTATT | SEQ ID No. 220 | TAGGTTGCATTTTCATCCTT |
| 10 | 5' | SEQ ID No. 221 | GGAATAGATTGTCTTGGGAAT | SEQ ID No. 222 | TAGGTTGCATTTTCATCCTT |
| 11 | 3' | SEQ ID No. 223 | GGCTCTCTGGGGCATCT | SEQ ID No. 224 | CAGGGGCCTGGGGAATG |
| 12 | 5' | SEQ ID No. 225 | TGTTTGAGAGGCAGAAGAT | SEQ ID No. 226 | TAGGTTGCATTTTCATCCTT |
| 13 | 5' | SEQ ID No. 227 | AGGTACTTGGTGGTGAATG | SEQ ID No. 228 | TAGGTTGCATTTTCATCCTT |
| 21 | 5' | SEQ ID No. 229 | TGAGTATCAGTATCATTTGTGA | SEQ ID No. 230 | TAGGTTGCATTTTCATCCTT |

FIGURE 8

METHOD FOR GENERATING A GENETICALLY MODIFIED PIG WITH INACTIVATED PORCINE ENDOGENOUS RETROVIRUS (PERV) ELEMENTS

PRIORITY CLAIM

This application is a national stage filing under 35 U.S.C. § 371 of International Patent Application No. PCT/US2018/028539, filed Apr. 20, 2018, which claims the benefit of priority to U.S. Provisional Application No. 62/487,898, filed Apr. 20, 2017, U.S. Provisional Application No. 62/500,197, filed May 2, 2017, U.S. Provisional Application No. 62/527,702, filed Jun. 30, 2017, and U.S. Provisional Application No. 62/543,610, filed Aug. 10, 2017, the disclosures of which are incorporated by reference herein in their entireties.

BACKGROUND OF THE DISCLOSURE

The shortage of human organs and tissues for transplantation represents a significant unmet medical need. In the United States and Europe alone, approximately 200,000 patients await organ transplantation, but only a small fraction of these patients ever receives donor organs (U.S. Department of Health and Human Services, Organ Procurement and Transplantation Network-2017; European Commission, Journalist workshop on organ donation and transplantation, Recent Facts & Figures, 2016). Several strategies have been envisioned to alleviate the critical shortage of donor organs, including developing organs in vitro from human induced pluripotent stem cells (hiPSCs), repopulating decellularized organ scaffolds, constructing 3D-printed organs, producing chimeric animals with human organs, and performing cross-species transplantation (i.e.; xenotransplantation), in particular, xenotransplantation is an attractive potential solution to the organ donation and transplantation shortage. Porcine organs are considered favorable resources for xenotransplantation since they are similar to human organs in size and function. Furthermore, pigs can be bred in large numbers under designated pathogen-free conditions and used in commercial production (Xenotransplantation 2.0, 2016, Nat. Biotechnol, 34:1).

Xenotransplantation has the potential to provide an almost unlimited supply of transplant organs for patients with chronic organ failure. However, the clinical use of porcine organs has been hindered by immunological incompatibilities and by the potential risk of porcine endogenous retroviral (PERK) element transmission. PERVs are proviruses in the porcine genome that originally became integrated in germ line chromosomes during exogenous retroviral infections (Gifford, R. & Tristem, M., 2003, Virus Genes 26, 291-315). There are three major subtypes of PERVs: PERV A, PERV B, and PERV C. Subtypes A and B are ubiquitous and can be transmitted to pigs and humans, whereas C is only present in some pig strains and can be transmitted among pigs (Patience et al., 2001, J. Virol, 75:2771-2775). PERVs, by definition, are not shared by other species and are typically the result of recent retroviral infections (Gifford and Tristem).

Most PERVs have become inactive over time with accumulated mutations, but certain intact PERVs have been shown to infect human cells in vitro (Patience et al., 1997, Nat. Med., 3:282-286; Yang et al., 2015, Science, 350: 110141104). These intact PERVs pose a potential risk of zoonosis in pig-to-human xenotransplantation (Denner et al., 2016, Xenotransplantation, 23:53-59; Denner J and Tonjes R, 2012, Clin Microbiol Rev, 2.5:318-343), Because mutagenesis from PERV integration could potentially lead to tumorigenesis and immunodeficiency, as reported with other retroviruses (Bendinelli et al., 1985, Advances in Cancer Research, 45:125-181), PERVs have been considered to be a major safety concern in the context of clinical xenotransplantation. Previously, several groups have attempted to inactivate PERVs using TAL effector nucleases (Dunn et al., 2015, FASEB J, 29:LB761) or Zinc Finger Nucleases (Semaan et al., 2015, PLUS One, 10), but these attempts have been unsuccessful.

Genetically modified animals, engineered to have deliberate modifications in their genomes, have been used for decades for scientific purposes, to improve livestock, and for production of recombinant proteins, among other uses. Many techniques have been developed for generating genetically modified animals including transcription activator-like effector nuclease (TALEN), zinc finger nuclease (ZEN), deaminases, and clustered regularly interspaced short palindromic repeats (CRISPR)-based systems, such as CRISPR-Cas9. Recently, these techniques have been employed to target multiple nucleic acid sequences for multiplexed genome editing in vitro. However, the success rate of a live birth and/or survival after birth for genetically modified animals depends on numerous factors including the technique used, genomic region(s) targeted, and the species of animal modified, but the rate is lower than for non-genetically modified animals.

As such, there is a need for developing PERV-free pigs as a source of cells, tissues, and/or organs for transplantation to humans and for techniques to improve the birth and/or survival rate of genetically modified animals, in particular, those engineered to have multiple genetic modifications.

SUMMARY OF THE DISCLOSURE

In some aspects the disclosure provides swine grown from an embryo, wherein the embryo comprises porcine cells having at least 75% inactive porcine endogenous retroviral (PERV) elements.

In some aspects the disclosure provides methods of generating a porcine endogenous retrovirus (PERV)-inactivated pig comprising: obtaining a nuclear donor cell having a nucleus, wherein at least 75% of the PERV elements in the nuclear donor cell are inactive; transferring the nucleus of the nuclear donor cell into a recipient enucleated oocyte to generate nucleus-transferred oocyte; subjecting the nucleus-transferred oocyte to activation; culturing the nucleus-transferred oocyte to generate a blastocyst or embryo; transferring the blastocyst or embryo to a surrogate; and generating a living PERV-inactivated pig from the blastocyst or embryo.

In some aspects the disclosure provides methods of generating a porcine endogenous retrovirus (PERV)-inactivated pig comprising: using a nucleus from a nuclear donor cell to generate a blastocyst or embryo, wherein at least 75% of the PERV elements in the nuclear donor cell are inactive; and transferring the blastocyst or embryo to a surrogate to generate a PERV-inactivated pig.

In some aspects the disclosure provides methods of improving the birth rate of PERV-inactivated pigs comprising: using nuclei from nuclear donor cells to generate blastocysts or embryos, wherein at least 75% of the PERV elements in the nuclear donor cells are inactive; and transferring the blastocysts or embryos to at least one surrogate to generate at least one PERV-inactivated pig, wherein the miscarriage rate is reduced as compared to the miscarriage rate of fetuses generated from a cell wherein more than 25% of the PERV elements in the cell are active.

In some aspects the disclosure provides methods of generating a genetically modified animal comprising: using a nucleus from a nuclear donor cell to generate a blastocyst or embryo, wherein a plurality of nucleic acid sequences in the nuclear donor cell are modified; and transferring the blastocyst or embryo to a surrogate to generate the genetically modified animal.

In some aspects the disclosure provides methods of preventing or reducing risk of pregnancy loss or miscarriage following somatic cell nuclear transfer (SCNT) of a genetically modified blastocyst or embryo comprising: using, a nucleus from a genetically modified nuclear donor cell to generate a blastocyst or embryo; and transferring the blastocyst or embryo to a surrogate to generate at least one a viable offspring wherein the rate of pregnancy loss or miscarriage is reduced as compared to the rate of pregnancy loss or miscarriage of a control.

Also provided are organs or tissues obtained from the swine of any of the embodiments disclosed and described herein. Also provided are isolated porcine cells generated by any of the methods disclosed and described herein.

In some embodiments, about 100% of the PERV elements in the cells are inactive. In some embodiments, 100% of the PERV elements in the cells are inactive.

In some embodiments, the PERV elements comprise one or more mutations or epigenetic changes that result in decreased or eliminated activity of PERV elements.

In some embodiments, the PERV elements of the porcine cell have been inactivated by a method comprising, administering to the cell a genome modifying agent specific to a gene involved in PERV replication and/or assembly, wherein the agent disrupts transcription and/or translation of the gene. In some embodiments, the agent is a nuclease or nickase or a nucleic acid encoding the nuclease or nickase, for example, the nuclease or nickase is a CRISPR-associated nuclease or nickase. In some embodiments, the agent further comprises: a) a CRISPR guide RNA car tracrRNA or; b) a nucleic acid encoding the CRISPR guide RNA.

In some embodiments, the CRISPR guide RNA comprises the nucleotide sequence of any one of SEQ ID NOs: 1-3 or 26-181, any strain specific genetic variant thereof, or any combination thereof. In some embodiments, the CRISPR guide RNA comprises the nucleotide sequence of any one of SEQ ID NOs: 1-3 or 26-116, any strain specific genetic variant thereof, or any combination thereof. In some embodiments, the CRISPR guide RNA comprises the nucleotide sequence of any one of SEQ ID NOs: 35, 36, 48, 99, 101, 102, 106, 108, 111, 113, or any combination thereof. In some embodiments, the agent is a nucleic acid encoding the CRISPR-Cas9 nuclease or nickase, wherein the cell is engineered to stably express the agent, wherein the agent further comprises at least one guide RNA, and wherein at least one guide RNA sequence comprises the nucleotide sequence of any one of SEQ. ID NOs: 1-3 or 26-116.

In some embodiments, the swine maintains a same or substantially same level of VERY inactivation for at least a month, at least 6 months, at least 1 year, at least 5 years, at least 10 years post-gestation.

In some embodiments, the nuclear donor cell is a somatic cell, a fetal cell, a germline cell, a stem cell, or and induced pluripotent stem cell (iPSC). In some embodiments, the nuclear donor cell is a fetal cell. In some embodiments, the nuclear donor cell is isolated from a chimeric PERU inactivated fetus. In some embodiments, the chimeric. PER inactivated fetus is at about 10 days, about 20 days, about 30 days, or about 3 months gestation.

In some embodiments, the chimeric PERV-inactivated fetus is generated using a genome modifying agent, for example, Zinc Finger nuclease or nickase, TAL effector nuclease or nickase, deaminase, and CRISPR associate nuclease or nickase.

In some embodiments, the nuclear donor cell undergoes less than 30, less than 20, less than 10, less than 5, or less than 2 population doublings in vitro. In some embodiments, the nuclear donor cell is isolated from a pig. In some embodiments, the nuclear donor cell is isolated from the pig when the pig is less than 10 weeks, less than 8 weeks, less than 6 weeks, less than 5 weeks, less than 4 weeks, less than 3 weeks, less than 2 weeks, or less than 1 week in age. In some embodiments, at least about 80%, at least about 90%, at least about 95%, at least about 99% of the PEPS elements in the nuclear donor cell are inactive.

In some embodiments, the PERV-inactivated pig maintains a same or similar level of PERV inactivation for at least a month, at least 6 months, at least 1 year, at least 5 years, at least 10 years post-gestation.

In some embodiments, the methods further comprise transferring at least one wild type blastocyst or embryo to the surrogate.

In some embodiments, at least about 80%, at least about 90%, at least about 95%, at least about 99% of the PERV elements in the nuclear donor cell are inactive, in some embodiments, 100% of the PERV elements in the nuclear donor cell are inactive.

In some embodiments, the PERV-inactivated pig maintains a same or similar level of Fe RV inactivation for at least a month, at least 6 months, at least 1 year, at least 5 years, at least 10 years post-gestation. In some embodiments, the PERV-inactivated pig is a PERV-free pig. In some embodiments, the PERV-inactivated pigs has at least about 75%, at least about 80%, at least about 85%, at least about 90%, at least about 95%, or at least about 99% inactive PERV elements.

BRIEF DESCRIPTION OF THE DRAWINGS

FIG. 1B shows the PERV insertion sites in highly infected i-HEK293T-GFP clones. Among the 22 PERV insertion sites detected by inverse PCR, 15 were mapped to the intragenic region, A portion of the intragenic hits were tested, Seven out of 12 were validated by junction PCR and are shown. The 30 bp human genomic sequences are shown with solid underlining, whereas the PERV LTRs are shown in double underlining. The genomic sequences are aligned to the UCSC Genome Browser and the corresponding genes are listed.

FIG. 3A shows porcine blastocysts cloned from 100% PERV-free PFFF3. Day 7 PERV-free porcine blastocysts were stained with SOX2 (inner cell mass), DAPI (nuclei), and phalloidin (cell boundaries). Stained blastocysts were imaged using laser scanning confocal microscopy.

FIG. 6B is a table illustrating the effects of the large T antigen on clones grown from sorted single cells used to analyze the PERV editing efficiency. Large T antigen treatment increased the ratio of >80% and >90% PERV-ko clones by 3.75 and 5.06 folds, respectively, compared with the untreated group.

FIG. 8 shows primers used to detect PERV junctions in FF3CF.

DETAILED DESCRIPTION OF THE DISCLOSURE

Figure 1A:
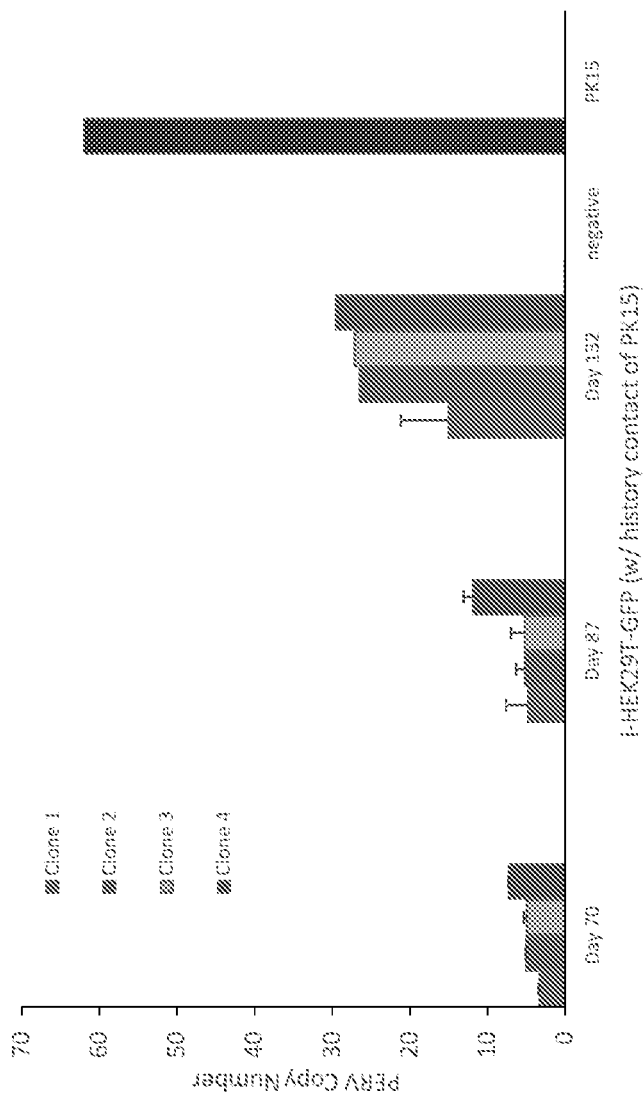
FIG. 1A shows that PERV copy number in infected human cells increases over time. Human HEK293T-GFP cells were co-cultured with equivalent numbers of pig PK15 cells for one week. The HEK293T-GFP single cells were isolated by flow cytometry based on the GFP signal and subsequently grown into clones. The HEK293T-GFP clones were isolated and cultured for the period of 70, 87 and 132 days. PERV copy numbers were analyzed by ddPCR using PEPS primers. HEK293T-GFP without any contact of PK15 cells were used as control.

The present disclosure provides for one or more genetically modified porcine cells having reduced intact PERVs, or methods of generating these cells. In some embodiments, the one or more porcine cells do not have any intact PERVs, or methods of generating these cells. In some embodiments, the PERV-reduced or PERV-free porcine cells may be cloned to produce porcine embryos, which may in turn be grown into adult swine from which organs and/or tissues may be extracted and used for such purposes as xenotransplantation into humans.

I. Definitions

The terms "about" and "approximately" as used in connection with a numerical value throughout the specification and the claims denotes an interval of accuracy, familiar and acceptable to a person skilled in the art.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers. As used herein, the term "comprises" also encompasses the use of the narrower terms "consisting" and "consisting essentially of."

The terms "pig", "swine" and "porcine" are used herein interchangeably to refer to anything related to the various breeds of domestic pig, species *Sus scrofa*.

The term "biologically active" when used to refer to a fragment or derivative of a protein or polypeptide means that the fragment or derivative retains at least one measurable and/or detectable biological activity of the reference full-length protein or polypeptide. For example, a biologically active fragment or derivative of a CRISPRCas9 protein may be capable of binding a guide RNA, binding a target DNA sequence when complexed with a guide RNA, and/or cleaving one or more DNA strands.

The terms "treatment", "treating", "alleviation" and the like, when used in the context of a disease, injury or disorder, are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms).

II. Porcine Cells, Tissues and Organs

In some embodiments, the cell is a mammalian cell. In some embodiments, the mammalian cell is a human cell. In some embodiments, the mammalian cell is a non-human mammalian cell, for example, equine, porcine, bovine, ovine, caprine, canine, or feline. In some embodiments, the cell is a porcine cell.

In some embodiments, the present disclosure provides for one or more porcine cells having reduced intact PERVs. In some embodiments, the porcine cell has been genetically modified such that the intact PERVs present in the porcine cell have been inactivated. In some embodiments, the porcine cell has less than 60, less than 50, less than 40, less than 30, less than 25, less than 20, less than 15, less than 10, less than 5, less than 3, less than 2, 1 or zero copies of intact PERVs. In some embodiments, the porcine cell has less than 10, less than 5, less than 3, less than 2, 1 or zero copies of intact PERVs. In some embodiments, the porcine cell has zero copies of intact PERVs. In some embodiments, the porcine cell has between about 60 copies and about 1 copy, between about 50 copies and about 1 copy, between about 40 copies and about 1 copy, between about 30 copies and about 1 copy, between about 20 copies and about 5 copies, between about 15 copies and about 10 copies, or between about 5 copies and about 1 copy of intact PERVs. In some embodiments, at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of the PERVs in the cell are inactive. In some embodiments, between about 30% and 100%, between about 35% and 100%, between about 40% and 100%, between about 45% and 100%, between about 50% and 100%, between about 55% and 100%, between about 60% and 100%, between about 65% and 100%, between about 70% and 100%, between about 75% and 100%, between about 80% and 100%, between about 85% and 100%, between about 90% and 100%, between about 95% and 100%, between about 96% and 100%, between about 97% and 100%, between about 98% and 100%, or between about 99% and 100% of the PERVs in the cell are inactive. In some embodiments, 100% of the PERVs in the cell are inactive.

In some embodiments, the cell is a primary cell, for example, a pig primary cell. In some embodiments, the cell is a somatic cell. In some embodiments, the cell is a post-natal cell. In some embodiments, the cell is an adult cell (e.g., an adult ear fibroblast). In some embodiments, the cell is a fetal/embryonic cell (e.g., an embryonic blastomere). In some embodiments, the cell is a germ line cell. In some embodiments, the cell is an oocyte. In some embodiments, the cell is a stem cell. In some embodiments, the cell is a cell from a primary cell line. In some embodiments, the cell is an epithelial cell, a muscle cell, a fibroblast, an endothelium cell, a liver cell, a granulosa cell, a fat cell. In particular embodiments, the cell is a fibroblast. In some embodiments, the fibroblast is a fetal fibroblast, for example a female fetal fibroblast. In some embodiments, the cell is a cancer cell. In some embodiments, the cell is not a cancer cell. In some embodiments, the cell is in vitro. In some embodiments, the cell is in vivo. In some embodiments, the cell is a single cell. In some embodiments, the cell is a member of a cell colony.

In some embodiments, the cell is a porcine cell. Non-limiting examples of porcine cells are cells that originates from or are derived from any of the following pig breeds: American Landrace, American Yorkshire, Aksai Black Pied, Angeln Saddleback, Appalachian English, Arapawa Island, Auckland Island, Australian Yorkshire, Babi Kampung, Ba Xuyen, Bantu, Basque, Bazna, Beijing Black, Belarus Black Pied, Belgian Landrace, Bengali Brown Shannaj, Bentheim Black Pied, Berkshire, Bisaro, Bangur, Black Slavonian, Black Canarian, Breitovo, British Landrace, British Lop, British Saddleback, Bulgarian White, Cambrough, Cantonese, Celtic, Chato Murciano, Chester White, Chiangmai Blackpig, Choctaw Hog, Creole, Czech Improved White, Danish Landrace, Danish Protest, Dermantsi Pied, Li Yan, Duroc, Dutch Landrace, East Landrace, East Balkan, Essex, Estonian Bacon, Fengjing, Finnish Tandrace, Forest Mountain, French Landrace, Gascon, German Landrace, Gloucestershire Old Spots, Gottingen minipig, Grice, Guinea Hog, Hampshire, Hante, Hereford, Hezuo, Hogan Hog, Huntington Black Hog, Iberian, Italian Landrace, Japanese Landrace, Jeju Black, Jinhua, Kakhetian, Kele, Kemerovo, Korean Native, Krskopolje, Kunekune, Lamcombe, Large Black, Large Black-White, Large White, Latvian White, Leicoma, Lithuanian Native, Lithuanian White, Lincolnshire Curly-Coated, Livny, Malhado de Alcobaca, Mangalitsa, Meishan, Middle White, Minzhu, Minokawa Buta, Mong Cai, Mora Romagnola, Moura, Mukota, Mulefoot, Murom, Myrhorod, Nero dei Nebrodi, Neijiang, New Zealand, Ningxiang, North Caucasian, North Siberian, Norwegian Landrace, Norwegian Yorkshire, Ossabaw Island, Oxford Sandy and Black, Pakchong 5, Philippine Native, Pietrain, Poland China, Red Wattle, Saddleback, Semirechensk, Siberian Black Pied, Small Black, Small White, Spots, Surabaya Babi, Swabian-Hall, Swedish Landrace, Swallow Belied Mangalitza, Taihu pig, Tamworth, Thuoc Nhieu, Tibetan, Tokyo-X, Tsivilsk, Turopolje, Ukrainian Spotted Steppe, Ukrainian White Steppe, Urzhum, Vietnamese Potbelly, Welsh, Wessex Saddleback, West French White, Windsnyer, Wuzhishanm, Yanan, Yorkshire and Yorkshire Blue and White.

In some embodiments, the cell (e.g., the donor nuclear cell) is isolated from a chimeric/mosaic fetus. As used herein the terms "chimeric" and "mosaic" may be used interchangeably and refer to a fetus having two or more populations of cells with different genotypes in the one fetus that has developed from a single fertilized egg. In some embodiments, the chimeric fetus is at about 5 days, about 10 days, about 15 days, about 20 days, about 25 days, about 30 days, about 2 months, about 3 months, about 4 months, about 5 months, about 6 months, about 7 months, about 8 months, about 9 months gestation or longer. In some embodiments, the chimeric fetus is less than about 5 days, less than about 10 days, less than about 15 days, less than about 20 days, less than about 25 days, less than about 30 days, less than about 2 months, less than about 3 months, less than about 4 months, less than about 5 months, less than about 6 months, less than about 7 months, less than about 8 months, or less than about 9 months gestation.

In some embodiments, the chimeric fetus is generated using a genome modifying agent, for example Zinc Finger nuclease or nickase, TAL effector nuclease or nickase, deaminase, and CRISPR associate nuclease or nickase. In some embodiments, the chimeric fetus is generated by direct zygote injection.

In some embodiments, the nuclear donor cell is isolated from an animal that is less than about 10 weeks, less than about 9 weeks, less than about 8 weeks, less than about 7 weeks, less than about 6 weeks, less than about 5 weeks, less than about 4 weeks, less than about 3 weeks, less than about 2 weeks, or less than 1 about week in age.

In some embodiments, the nuclear donor cell, for example, one isolated from a chimeric fetus, is expanded in vitro for a period of time. In some embodiments, the cell is expanded in vitro for less than about 30, less than about 25, less than about 20, less than about 15, less than about 10, less than about 5, or less than about 2 population doublings. In some embodiments, the cell is expanded in vitro for not more than about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 population doublings.

In some embodiments, the cells, before or after genetic modification, are cultured in the presence of one or more factors that improves the health and/or survival of the cell. In some embodiments the factor is BEPP monohydrochloride, pifithrin-$\alpha$, R18 trifluoroacetate, fibroblast growth factor (fgf), large T antigen, BCL, or any combination thereof. In some embodiments the factor(s) induces RNA-dependent protein kinase apoptosis, inhibits p53 mediated apoptosis, inhibits 14-3-3 proteins, promotes proliferation, promotes immortalization, is antiapoptotic, or any combination thereof.

In some embodiments, the factor is a cell cycle checkpoint inhibitor. In some embodiments, the factor is an anti-apoptotic factor. In some embodiments, the factor is bcl-2. In some embodiments, the factor is an inhibitor of any one of the following: c-Myc, Bax, p53, tBid, and BCL. The skilled worker is aware of various small molecules and possible derivatives of those small molecules that may be used as anti-apoptotic checkpoint inhibitors or anti-apoptotic factors. In some embodiments, the factor is the SV40 antigen.

In some embodiments, the factor is a p53 inhibitor. In some embodiments, the factor is a pifithrin molecule or derivative thereof. In some embodiments, the factor is pifithrin-alpha and/or pifithrin-beta. Pifithrin (PFT)-α has been demonstrated to reversibly inhibit p53-dependent transcriptional activation and apoptosis, and PFT-μ has been demonstrated to inhibit p53 binding to mitochondria by reducing p53-binding affinity to Bcl-xL and Bcl-2. In some embodiments, the p53 inhibitor is a cyclized PFT-α p53 inactivator such as cyclic Pifithrin-α hydrobromide. In some embodiments, the p53 inhibitor is a nucleic acid that reduces or eliminates p53 expression in the cell. In some embodiments, the nucleic acid is an antisense and/or RNAi molecule. In some embodiments, the p53 inhibitor is a dominant negative p53 protein, or a nucleic acid encoding a dominant negative p53 inhibitor. In some embodiments, the p53 inhibitor is selected from the group consisting of pifithrin-α, pifithrin-beta, pifithrin-α hydrobromide, pifithrin-mu, ellipticine, 9-hydroxyellipticine, nutlin-3, roscovitine, and SJ 172550.

In some embodiments, the factor is a growth factor. In some embodiments, the growth factor is of porcine origin. In some embodiments, the growth factor is a growth factor useful for the cell type that has been genetically modified. For example, if the genetically modified cell is fibroblast cell or cell of fibroblast lineage, than in some embodiments, the growth factor is fibroblast growth factor. In some embodiments, the fibroblast growth factor is basic fibroblast growth factor (bFGF) or fibroblast growth factor-2 (FGF-2). In some embodiments, the fibroblast growth factor is basic fibroblast growth factor (bFGF). In some embodiments, the growth factor is selected from the group consisting of: epidermal growth factor (EGF), insulin-like growth factor (IGF), platelet derived growth factor (PDGF), vascular endothelial growth factor (VEGF), and keratinocyte growth factor (KGF).

In some embodiments, the cells are administered both a p53 inhibitor and a growth factor. In certain embodiments, the cells are administered both bFGF and pifithrin-alpha.

In some embodiments, the cells of the disclosure are cultured in conditions of about 1-20% oxygen ($O_2$), about 1-20% carbon dioxide ($CO_2$), about 50-90% $N_2$, or any combination thereof. In some embodiments, the cells of the present disclosure are cultured under hypoxic conditions (e.g., in the presence of less than 10% $O_2$). In some embodiments, the cells of the present disclosure are cultured at about 37° C. In some embodiments, the cells of the present disclosure can be cultured at about 5% $O_2$, 5% $CO_2$ and 90% $N_2$. In some embodiments, the cells are cultured in a tri-gas incubator for at least a period of time.

In some embodiments, the cells of the present disclosure when cultured in vitro are split and/or frozen when the cells are below about 80%, about 70%, about 60%, about 50%, about 40%, about 30%, about 20%, about 10%, or less confluency. In some embodiments, the cells are split and/or frozen when the cells are below about 50% confluency.

III. Genetic Modifications

The present disclosure provides methods of generating genetically modified cells and animals derived therefrom.

In some embodiments, a plurality of endogenous nucleic acid sequences are modified by inactivation, insertion of exogenous nucleic acids, subtraction of endogenous nucleic acids, or any combination thereof to generate genetically modified cells and animals derived therefrom.

In some embodiments, a plurality of nucleic acid sequences in the cell (e.g., a nuclear donor cell) are modified. In some embodiments, at least about 2, at least about 5, at least about 10, at least about 20, at least about 30, at least about 40, at least about 50, at least about 60, at least about 70, at least about 80, at least about 90, at least about 100, or more nucleic acid sequences are modified. In some embodiments, the plurality of genetic modifications are to a single, repetitive gene sequence. In other embodiments, at least a portion of the genetic modifications are to different genes.

In some embodiments, the present disclosure provides for one or more cells having reduced intact viral elements (e.g., PERVs). In some embodiments, the nuclear donor cell has been genetically modified such that the intact viral elements present in the cell have been inactivated. In some embodiments, the cell has less than 60, less than 50, less than 40, less than 30, less than 25, less than 20, less than 15, less than 10, less than 5, less than 3, less than 2, 1 or zero copies of intact viral elements. In some embodiments, the porcine cell has less than 10, less than 5, less than 3, less than 2, 1 or zero copies of intact viral elements. In some embodiments, the porcine cell has zero copies of intact viral elements. In some embodiments, the cell has between about 60 copies and about 1 copy, between about 50 copies and about 1 copy, between about 40 copies and about 1 copy, between about 30 copies and about 1 copy, between about 20 copies and about 5 copies, between about 15 copies and about 10 copies, or between about 5 copies and about 1 copy of intact viral elements. In some embodiments, at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of the viral elements in the cell are inactive. In some embodiments, between about 30% and 100%, between about 35% and 100%, between about 40% and 100%, between about 45% and 100%, between about 50% and 100%, between about 55% and 100%, between about 60% and 100%, between about 65% and 100%, between about 70% and 100%, between about 75% and 100%, between about 80% and 100%, between about 85% and 100%, between about 90% and 100%, between about 95% and 100%, between about 96% and 100%, between about 97% and 100%, between about 98% and 100%, or between about 99% and 100% of the viral elements in the cell are inactive.

In some embodiments, the cells, tissues, organs or animals (e.g., pigs) of the present disclosure lack (or have been engineered to lack activated strains of) infectious viruses. In some embodiments, the cells lack an endogenous retrovirus. In some embodiments, the cells of the present disclosure lack (or have been engineered to lack activated strains of) any one or more of herpesvirus, porcine lymphotrophic herpesvirus (PLHV), pig cytomegalovirus (PCMV), encephalomyocarditis virus (EMCV), pig circovirus (PCV), hepatitis E virus (HEV), rabies viruses, pseudorabies viruses, parvovirus, swine vesicular disease viruses, porcine polio virus, hemagglutinating encephalomyocarditis viruses, swine influenza type A, adenovirus, transmissible gastroenteritis virus, vesicular stomatitis virus, feline leukemia virus, mouse mammary tumor virus, murine leukemia virus, simian immunodeficiency virus (SIV), equine infectious anemia, bovine immunodeficiency virus (BIV), and the like. In some embodiments, the cells, tissues, organs or pigs of the present disclosure lack (or have been engineered to lack activated strains of) PERVs.

In some embodiments, the cells, tissues, organs or animal (e.g., pigs) of the disclosure comprise one or more inactivating mutations. In some embodiments, the cells, tissues, organs or animals comprise one or more mutations or epigenetic changes that result in decreased or eliminated activity of the nucleic acid sequence (e.g., a gene or retroviral element such as PERV elements). In some embodiments, the one or more nucleic acid sequences (e.g., PERV element) is inactivated by genetically modifying the nucleic acid(s) present in the cell, tissue, organ or animal. In some embodiments, the inactivation of one or more nucleic acid sequences (e.g., PERV elements) is confirmed by means of an assay. In some embodiments, the assay is an infectivity assay, reverse transcriptase PCR assay, RNA-seq, real-time PCR, or junction PCR mapping assay.

The cells, tissues, organs or animals can be genetically modified according to any method known by one of skill in the art. In some embodiments, the nucleic acid(s) in the cell are genetically modified such that one or more nucleic acid sequences (e.g., genes or retroviral elements) in the cell are inactivated. In some embodiments, the nucleic acid sequences are genetically modified using any of the genetic modifications systems known in the art and/or disclosed herein. In some embodiments, the genetic modification system is a TALEN, a zinc finger nuclease, and/or a CRISPR-based system. In some embodiments, the genetic modification system is a CRISPR-Cas9 system. In some embodiments, the cell is genetically modified such that one or more nucleic acid sequences in the cell are inactivated, and the cell is further genetically modified such that the cell has reduced expression of one or more genes that would induce an immune response if the cell (or a tissue or organ cloned/derived from the cell) were transplanted to a human. In some embodiments, the cell is genetically modified such that one or more nucleic acid sequences in the cell are inactivated and the cell is further genetically modified such that the cell has increased expression of one or more genes that would suppress an immune response if the cell (or a tissue or organ cloned/derived from the cell) were transplanted to a human. In some embodiments, the cell is genetically modified such that one or more nucleic acid sequences in the cell are inactivated, and the cell is further genetically modified such that the cell has reduced expression of one or more genes that would induce an immune response if the cell (or a tissue or organ cloned/derived from the cell) were transplanted to a human, and the cell is further genetically modified such that the cell has increased expression of one or more genes that would suppress an immune response if the cell (or a tissue or organ cloned/derived from the cell) were transplanted to a human.

In some embodiments, the disclosure provides for a blastocyst or an embryo that was cloned from the genetically modified cell. In some embodiments, the genetically modified nucleic acid(s) are extracted from the genetically modified cell and cloned into a different cell. For example, in somatic cell nuclear transfer, the genetically modified nucleic acid from the genetically modified cell is introduced into an enucleated oocyte. In some embodiments, oocytes can be enucleated by partial zona dissection near the polar body and then pressing out cytoplasm at the dissection area. In some embodiments, oocytes are obtained with all or substantially all of the cytoplasm intact. In some embodiments, the oocytes are screened for multiple layers of cumulus cells. In some embodiments, an injection pipette with a sharp beveled tip is used to inject the genetically modified cell into an enucleated oocyte arrested at meiosis 2. Oocytes arrested at meiosis-2 are frequently termed "eggs." In some embodiments, an embryo is generated by fusing and activating the oocyte. Such an embryo may be referred to herein as a "genetically modified embryo." In some embodiments, the genetically modified embryo is transferred to the oviducts of a recipient female pig.

A genetically modified blastocyst or embryo can be generated according to any embodiment disclosed herein. In one embodiment, a porcine fetal fibroblast cell can be obtained and transfected using neon transfection reagent, biotin-conjugated beads can be used to counter select for knockout genes and/or antibody binding selection for knock-in genes through FACS, single cells having the desired modifications sorted and expanded in vitro, cells genotyped and/or PCR verified for positive clones, followed by cell transportation and SCNT cloning, or any combination thereof. In some embodiments, the genetic modifications are conducted on a zygote using, for example, microinjection instead of cells in vitro. It is contemplated that direct injection into a zygote may be less stressful on the cells. When zygote modification is performed, embryos are then transferred to obtain mosaic animals and cells are isolated from the mosaic fetus to be used for SCNT cloning.

In some embodiments, the cells, blastocysts, embryos and the like that are generated according to any embodiment disclosed herein are tested for quality control. Non-limiting examples of quality control include any of Miseq and Sanger sequencing to detect gene targeting efficiency, Exome sequencing and/or whole genome sequencing to detect off-targeting, karyotyping to detect chromosome abnormalities, RT-qPCR to detect target gene expression, RNAseq to detect the normality of whole gene expression pattern, antibody binding counter selection for knockout gene (e.g., by bead enrichment), specific gene antibody binding selection for knock-in genes (e.g., by flow cytometry sorting); specific gene antibody binding, human serum antibody binding, complement cytotoxicity, or natural killer (NK) cell assay to detect the physiological function of target gene, blastocyst development ratio to check whether gene editing influences embryo development, and any combination thereof.

IV. Surrogates and/or Somatic Cell Nuclear Transfer

In some embodiments, the genetically modified blastocyst or embryo is transferred to a surrogate, for example, the oviduct of the surrogate. In some embodiments, the genetically modified blastocyst or embryo is transferred to the oviducts of a surrogate about 20 to 24 hours after activation. In some embodiments, more than one blastocyst or embryo is transferred to the surrogate. In some embodiments between about 1 and about 600, between about 50 and about 500, between about 100 and about 400, or between about 200 and about 300 blastocysts or embryos are transferred. In some embodiments, the embryos are checked for quality control prior to transferring, for example, checking the cleavage and blastocyst ratio. In some embodiments, embryos or blastocysts derived from the sample cell are transferred into multiple surrogates, for example, between about 5-20 surrogates/cell line. In some embodiments, at least one wild type blastocyst or embryo is transferred to the surrogate at the same time or substantially the same time as the genetically modified blastocyst or embryo. In some embodiments, at least one wild type blastocyst or embryo is transferred to the surrogate prior to or after the genetically modified blastocyst or embryo is transferred to the surrogate. In some embodiments, surrogate is checked for pregnancy approximately 20-21 days after transfer of the genetically modified blastocyst or embryo.

In some embodiments, the surrogate is screened for certain characteristics prior to transferring of the blastocyst or embryo. Non-limiting examples of surrogate characteristics include physiological stage, age, fertility, maternal behavior, lactation and rearing ability, abortion frequency, disease, or any combination thereof. In some embodiments, the surrogate is selected for prior litter size, suitable age, having more than one birth history, and/or with suitable physiological stage. In some embodiments, the blastocyst or embryo transfer is performed in the spring or fall. In some embodiments, the blastocyst or embryo transfer is not performed in the summer and/or winter.

In some embodiments, a large surrogate is selection. It is contemplated that larger surrogates can improve the pig production as measured by any one, or combination of, outcome measures including delivery rate, liter size, survival rate, and expected pigs per sow as compared to smaller surrogates.

In some embodiments, a first round of SCNT is performed to generate an embryo that is transferred to a surrogate to generate a fetus and then cells are isolated from a fetus. The isolated cells are then used for a second round of SCNT and transferred to a surrogate to generate a genetically modified animal. In some embodiments, the fetus used in the second round of SCNT is sacrificed at about 10 days, about 20 days, about 30 days, about 40 days, about 50 days, about 60 days, about 70 days, about 80 days, about 90 days, about 100 days, or about 100 days gestation. In some embodiments, the fetus used in the second round of SCNT is less than about 50 days, less than about 40 days, less than about 30 days, less than about 20 days, or less than about 10 days gestation.

In some embodiments, the genetically modified blastocyst or embryo is grown into a post-natal genetically modified animal (e.g., pig). In some embodiments, the post-natal genetically modified animal is a neo-natal genetically modified animal. In some embodiments, the genetically modified animal is a juvenile genetically modified animal. In some embodiments, the genetically modified animal is an adult genetically modified animal (e.g., older than 5-6 months). In some embodiments, the genetically modified animal is a female genetically modified animal. In some embodiments, the animal is a male genetically modified animal. In some embodiments, the genetically modified animal is bred with a non-genetically modified animal. In some embodiments, the genetically modified animal is bred with another genetically modified animal. In some embodiments, the genetically modified animal is bred with another genetically modified animal that has reduced or no active retrovirus (e.g., PERVs). In some embodiments, the genetically modified animal is bred with a second genetically modified animal that has been genetically modified such that the cells, tissues or organs from the second genetically modified animal are less likely to induce an immune response if transplanted to a human.

V. Genetically Modified Animals

The present disclosure also provides for methods of preventing or reducing risk of pregnancy loss or miscarriage following somatic cell nuclear transfer (SCNT) of a genetically modified blastocyst or embryo comprising: using a nucleus from a genetically modified nuclear donor cell to generate a blastocyst or embryo; and transferring the blastocyst or embryo to a surrogate to generate at least one a viable offspring wherein the rate of pregnancy loss or miscarriage is reduced as compared to the rate of pregnancy loss or miscarriage of a control.

In some embodiments, the rate of pregnancy loss or miscarriage is reduced by at least about 5%, at least about 10%, at least about 20%, at least about 30%, at least about 40%, at least about 50%, at least about 60%, at least about 70%, at least about 80%, at least about 90%, or more as compared to the rate of pregnancy loss or miscarriage of a control genetically modified blastocyst or embryo.

In some embodiments the genetically modified animal maintains a same or similar level of genetic modification for at least a month, at least 6 months, at least 1 year, at least 5 years, at least 10 years post-gestation.

In some embodiments, the genetically modified animal remains alive for at least a month, at least 2 months, at least 3 months, at least 4 months, at least 5 months, at least 6 months, at least 7 months, at least 8 months, at least 9 months, at least 10 months, at least 11 months, at least a year, at least 2 years, at least 3 years, at least 4 years, at least 5 years, at least 6 years, at least 7 years, at least 8 years, at least 9 years, at least 10 years, or more.

In some embodiments the genetically modified pig are PERV-inactivated genetically modified pigs and maintain a same or similar level of PERV inactivation for at least a month, at least 6 months, at least 1 year, at least 5 years, at least 10 years post-gestation. In some embodiments, the genetically modified pig remains PERV-inactivated genetically modified pigs even after delivery from a non-PERV-inactivated surrogate or after being in a facility/space with other non-PERV-inactivated pigs.

In some embodiments, the disclosure provides for cells, tissues or organs obtained from any of the post-natal genetically modified animals (e.g., pigs) described herein. In some embodiments, the cell, tissue or organ is selected from the group consisting of: liver, lung, heart, brain, pancreas, muscle, blood, bone, testes and ovary. In some embodiments, the organ is liver, lung or heart. In some embodiments, the cell from the post-natal genetically modified animal is selected from the group consisting of: pancreatic islets, lung epithelial cells, cardiac muscle cells, skeletal muscle cells, smooth muscle cells, hepatocytes, non-parenchymal liver cells, gall bladder epithelial cells, gall bladder endothelial cells, bile duct epithelial cells, bile duct endothelial cells, hepatic vessel epithelial cells, hepatic vessel endothelial cells, sinusoid cells, choroid plexus cells, fibroblasts, Sertoli cells, neuronal cells, stem cells, and adrenal chromaffin cells. In some embodiments, the genetically modified organs, tissues or cells have been separated from their natural environment (i.e., separated from the animal in which they are being grown). In some embodiments, separation from the natural environment means a gross physical separation from the natural environment, e.g., removal from the genetically modified donor animal, and alteration of the genetically modified organs', tissues' or cells' relationship with the neighboring cells with which they are in direct contact (e.g., by dissociation).

III. Methods of Generating PERV-Reduced or PERV-Free Porcine Cells

The disclosure provides for methods of generating any of the PERV-reduced PERV-free porcine cells disclosed herein. In some embodiments, the disclosure provides a method of inactivating a PERV element in any of the porcine cells disclosed herein, comprising administering to the cell a genome modifying agent specific to a gene involved in PERV replication and/or assembly, wherein the agent disrupts transcription and/or translation of the gene. In some embodiments, the agent targets the start codon of the gene and inhibits transcription of the gene. In some embodiments, the agent targets an exon in the gene and the agent induces a frameshift mutation in the gene. In some embodiments, the agent introduces an inactivating mutation into the gene. In some embodiments, the agent represses transcription of the gene.

The skilled worker is aware of numerous assays for determining whether a cell is PERV free. One method would be to expose a human cell to a genetically modified cell believed to be PERV-reduced or PERV-free and monitor PERV infection of the human cell, i.e., an infectivity assay. See, e.g., Examples 1 and 2. Other methods of monitoring PERV activity in a genetically modified cell include, e.g., RNAseq, Reverse Transcriptase-PCR, microarrays, and/or junction PCR reactions to monitor expression and/or chromosomal integrity of PERV related genes (e.g., gag, pol and/or env).

In some embodiments, any of the agents disclosed herein is a polynucleotide. In some embodiments, the polynucleotide encodes one or more of the nucleases and/or nickases and/or RNA or DNA molecules described herein. In some embodiments, the polynucleotide agent is introduced to one or more PERV porcine cells. In some embodiments, the polynucleotide is introduced to the one or more PERV porcine cells in a manner such that the polynucleotide is transiently expressed by the one or more cells. In some embodiments, the polynucleotide is introduced to the one or more PERV porcine cells in a manner such that the polynucleotide is stably expressed by the one or more cells. In some embodiments, the polynucleotide is introduced in a manner such that it is stably incorporated in the porcine cell genome. In some embodiments, the polynucleotide is introduced along with one or more transposonal elements. In some embodiments, the transposonal element is a polynucleotide sequence encoding a transposase. In some embodiments, the transposonal element is a polynucleotide sequence encoding a PiggyBac transposase. In some embodiments, the transposable element is inducible. In some embodiments, the transposable element is doxycycline-inducible. In some embodiments, the polynucleotide further comprises a selectable marker. In some embodiments, the selectable marker is a puromycin-resistant marker. In some embodiments, the selectable marker is a fluorescent protein (e.g., GFP).

In some embodiments, the agent is a nuclease or a nickase that is used to target PERV DNA in the cell. In some embodiments, the agent specifically targets and suppresses expression of a PERV. In some embodiments, the agent comprises a transcription repressor domain. In some embodiments, the transcription repressor domain is a Krüppel associated box (KRAB).

In some embodiments, the agent is any programmable nuclease. In some embodiments, the agent is a natural homing meganuclease. In some embodiments, the agent is a TALEN-based agent, a ZFN-based agent, or a CRISPR-based agent, or any biologically active fragment, fusion, derivative or combination thereof. In some embodiments, the agent is a deaminase or a nucleic acid encoding a deaminase. In some embodiments, a cell is engineered to stably and/or transiently express a TALEN-based agent, a ZFN-based agent, and/or a CRISPR-based agent.

A. TALEN-Based Agents

In some embodiments, the agent is a TALEN-based agent. In some embodiments, the TALEN-based agent is one or more TALEN polypeptides/proteins or biologically active fragments or derivatives thereof, or one more nucleic acids encoding one or more TALEN polypeptides or fragments or derivatives thereof. Transcription activator-like (TAL) effector sequences can be assembled to bind DNA targets with specificity by assembling sequences of repeat variable-diresidues (RVDs). Fusion proteins of TAL effectors and nucleases (TALENs) can make targeted double-stranded breaks in cellular DNA that can be used to make specific genetic modifications to cells. In some embodiments, the agent is a TALEN polypeptide/protein or fragment or derivative thereof that targets one or more PERV DNA sequences in a PERV cell. In some embodiments, the Repeat Variable Diresidue (RVD) portion of the TALEN has been engineered to target one or more PERV DNA sequences in a PERV cell. In some embodiments, the TALEN-based agent is a nucleic acid encoding one or more TALEN protein. In some embodiments, the nucleic acid is in a plasmid. In some embodiments, the nucleic acid is mRNA.

In some embodiments, the TALEN protein is expressed in a cell and induces a site-specific double stranded DNA break in one or more PERV gene. In some embodiments, the TALEN protein introduces a donor sequence, wherein the donor sequence partially or completely replaces the PERV gene, thereby silencing or inactivating the PERV gene. In some embodiments, the TALEN is a left TALEN and further comprising a right TALEN that cooperates with the left TALEN to make the double strand break in the PERV gene. In another embodiment, the nucleic acid encoding the TALEN and/or the nucleic acid donor sequence is part of a vector or plasmid. In some embodiment, the TALEN includes a spacer (e.g., the spacer sequence is 12 to 30 nucleotides in length).

In some embodiments, the TALEN protein comprises a TAL effector DNA-binding domain and/or a modified FokI nuclease catalytic domain. In some embodiments, the TAL effector DNA-binding domain binds to a region in a PERV gene. In some embodiments, the TALEN comprises, from the N-terminus to the C-terminus: (i) a first segment of about 50 to about 200 amino acids in length; (ii) a TAL effector DNA-binding domain providing sequence-specific binding to a PERV nucleotide sequence; (iii) a second segment of about 20 to 100 amino acids in length; and (iv) a modified FokI nuclease catalytic domain.

Methods of engineering a TALEN to bind to specific nucleic acids are described in Cermak, et al, Nucl. Acids Res. 1-1 1 (2011). US Published Application No. 2011/0145940 discloses TAL effectors and methods of using them to modify DNA. Miller et al. Nature Biotechnol 29: 143 (2011) describes the generation of TALENs for site-specific nuclease architecture by linking TAL truncation variants to the catalytic domain of Fok I nuclease. General design principles for TALEN binding domains can be found in, for example, WO 2011/072246. Each of these documents is incorporated herein in its entirety.

In some embodiments, the TALEN-based agent targets a nucleotide sequence of a PERV. In some embodiments, the TALEN-based agent targets a nucleotide sequence that is conserved across more than one strain of PERV. In some embodiments, the TALEN-based agent targets a PERV pol, env, and/or gag gene. In some embodiments, the TALEN-based agent targets a PERV pol gene. In some embodiments, the TALEN-based agent targets the sequence encoding the catalytic core of a PERV pol gene.

B. ZFN-Based-Agents

In some embodiments, the agent is a zinc finger nuclease (ZFN)-based agent. In some embodiments, the ZFN-based agent is one or more ZFN polypeptides or biologically active fragments or derivatives thereof, or one more nucleic acids encoding one or more ZFN polypeptides or fragments or derivatives thereof. ZFNs are artificial restriction enzymes generated by fusing a zinc finger DNA-binding domain to a nuclease. Zinc finger domains can be engineered to target specific desired DNA sequences and this enables zinc-finger nucleases to target unique sequences within complex genomes. The DNA-binding domains of individual ZFNs typically contain between three and six individual zinc finger repeats and can each recognize between 9 and 18 base pairs (bp). If the zinc finger domains perfectly recognize a 3 basepair DNA sequence to generate a 3-finger array, that array can recognize a 9 basepair target site. In some embodiments, either I-finger or 2-finger modules are utilized to generate zinc-finger arrays with six or more individual zinc fingers. Because the specificities of individual zinc fingers can overlap and can depend on the context of the surrounding zinc fingers and DNA, ZFNs may not be useful for targeting specific PERVs.

Numerous selection methods have been developed to generate zinc-finger arrays capable of targeting desired sequences. In some embodiments, initial selection efforts utilize phage display to select proteins that bind a given DNA target from a large pool of partially randomized zinc-finger arrays. In some embodiments, yeast one-hybrid systems, bacterial one-hybrid and two-hybrid systems (e.g., the "OPEN" system), and mammalian cells may be used to select proteins that bind a given DNA. In particular, the OPEN system combines pre-selected pools of individual zinc fingers that were each selected to bind a given triplet and then utilizes a second round of selection to obtain 3-finger arrays capable of binding a desired 9-bp sequence.

In some embodiments, the process for editing the PERV gene sequence comprises introducing into a cell at least one nucleic acid encoding a zinc finger nuclease that recognizes the PERV sequence in the genome and is able to cleave a site in the PERV gene sequence. In some embodiments, process further comprises introducing at least one donor polynucleotide comprising a sequence for integration flanked by an upstream sequence and a downstream sequence that share substantial sequence identity with either side of the cleavage site. In some embodiments, process further comprises introducing at least one exchange polynucleotide comprising a sequence that is substantially identical to a portion of the genomic PERV sequence at the cleavage site and which further comprises at least one nucleotide change. In some embodiments, the cell is cultured to allow expression of the zinc finger nuclease such that the zinc finger nuclease introduces a double-stranded break into the genomic PERV sequence. In some embodiments, the double-stranded break is repaired by a non-homologous end-joining repair process such that a silencing or inactivating mutation is introduced into the chromosomal sequence. In some embodiments, the double-stranded break is repaired by a homology-directed repair process such that the sequence in the donor polynucleotide is integrated into the genomic PERV sequence or the sequence in the exchange polynucleotide is exchanged with the portion of the chromosomal sequence.

In some embodiments, the zinc finger nuclease targets a nucleotide sequence of a PERV. In some embodiments, the zinc finger nuclease targets a nucleotide sequence that is conserved across more than one strain of PERV. In some embodiments, the zinc finger nuclease targets a PERV pol, env, and/or gag gene. In some embodiments, the zinc finger nuclease targets a PERV pol gene. In some embodiments, the zinc finger nuclease targets the sequence encoding the catalytic core of a PERV pol gene.

C. CRISPR-Based Agents

In some embodiments, the agent is a CRISPR-based agent. In some embodiments, the CRISPR-based agent is one or more polynucleotides involved in the expression of or directing the activity of CRISPR-associated ("Cas") genes, including, but not limited to, sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus. In some embodiments, the CRISPR-based agent is a polynucleotide that encodes at least one CRISPR protein and one or more guide RNAs (gRNAs). In some embodiments, the one or more gRNAs comprise a sequence cognate to a PERV polynucleotide sequence and capable of binding to a protospacer adjacent motif ("PAM"). In some embodiments, the PAM includes the sequence NGG or NNGRRT.

In some embodiments, the agent is a CRISPR-based polypeptide or fragment or derivative thereof that targets one or more PERV DNA sequences in a PERV cell. In some embodiments, the CRISPR-based agent is characterized by elements that promote the formation of a CRISPR complex at the site of PERV DNA or RNA sequences. In some embodiments, the CRISPR-based agent is one or more CRISPR/Cas endonuclease or biologically active fragments or derivatives thereof, or one or more nucleic acids encoding one or more CRISPR/Cas polypeptides or fragments or derivatives thereof. In some embodiments, the CRISPR/Cas endonuclease or a derivative thereof is from the CRISPR Type I system. In some embodiments, the CRISPR/Cas endonuclease or a derivative thereof is from the CRISPR Type II system. In some embodiments, the CRISPR/Cas endonuclease or a derivative thereof is from the CRISPR Type III system. In some embodiments, the CRISPR % Cas endonuclease or a derivative thereof is from the CRISPR Type IV system. In some embodiments, the CRISPRCas endonuclease or a derivative thereof is from the CRISPR Type V system. In some embodiments, the CRISPRICas endonuclease or a derivative thereof is from the CRISPR Type VI system. In some embodiments, the CRISPR/Cas endonuclease or a derivative thereof is from the CRISPR Type IIA, Type JIB or Type HC systems. In some embodiments, the CRISPR/Cas endonuclease or a derivative thereof is from the CRISPR Type IIC system. In some embodiments, the type II CRISPR/Cas endonuclease is Cas9, or a derivative thereof. In some embodiments, the CRISPR/Cas endonuclease or a derivative thereof is a type V CRISPR/Cas endonuclease, such as Cpf1, or a derivative thereof. In some embodiments, the site-directed modifying polypeptide is a Type III-B Cmr complex, e.g., a Type III-B Cmr complex derived from *Pyrococcus furiosus, Sulfolobus sojatoricus,* or *Thermus thermophilus.* See, e.g., Hale, C. R. et al. *Genes & Development,* 2014, 28:2432-2443, and Makarova K. S. et al. *Nature Reviews Microbiology,* 2015, 13, 1-15.

In particular embodiments, the CRISPR-based agent utilizes the Type I cas9 endonuclease. In some embodiments, the CRISPR-based agent comprises the Type II cas9 endonuclease and an additional polynucleotide. In some embodiments, the additional polynucleotide is a tracrRNA, crRNA (also referred to as a "tracr-mate RNA) and/or a synthetic single guide RNA (sgRNA). See, e.g., Jinek, M., et al. (2012) Science, 337, 816-821.

In some embodiments, the CRISPR-based agent is a Cas protein that lacks the ability to cleave double stranded DNA.

In some embodiments, the Cas protein is capable of only cleaving a single strand of DNA, i.e., the Cas protein is a "nickase." In some embodiments, the Cas protein is incapable of cleaving either strand of DNA. In some embodiments, the Cas protein is a Cas9 protein that has been mutated such that it is a nickase or such that it lacks the ability to cleave either strand of DNA. In some embodiments, the Cas9 protein has a D10A and/or an H840A mutation. In some embodiments, the agent is a polynucleotide that encodes for a Cas9 protein having a DOA and/or an 11840A mutation. See, e.g., Cong L., ct al. (2013) Science, 339, 819-823; Jinck, M., et al. (2012) Science, 337, 816-821; Gasiunas, G., et al. (2012) Proc. Nat. Acad. Sci. USA. 109, E2579-2586; and Mali, P., et al. (2013) Science, 339, 823-826; each of which is incorporated by reference herein in its entirety.

In some embodiments, the CRISPR-based agent comprises a gRNA. In some embodiments, the gRNA targets a nucleotide sequence of a PERV. In some embodiments, the gRNA targets a nucleotide sequence that is conserved across more than one strain of PERV. In some embodiments, the gRNA targets a PERV pol, env, and/or gag gene. In some embodiments, the gRNA targets a PERV pol gene. In some embodiments, the gRNA targets the sequence encoding the catalytic core of a PERV pol gene. In some embodiments, the gRNA targets a non-catalytic core region of a PERV pol gene. In some embodiments, the non-catalytic core region of a PERV pol gene is upstream of the catalytic core region of a PER V pol gene.

In some embodiments, the gRNA comprises the nucleotide sequence of any one of SEQ ID NOs: 1-3 or 26-116, fragments, or any strain specific genetic variant thereof. In particular embodiments, the gRNA comprises the nucleotide sequence of any one of SEQ ID NOs: 1-3, fragments, or any strain specific genetic variant thereof. In some embodiments, the gRNA comprises the nucleotide sequence of any one of SEQ ID NOs: 1-3 or 26-181 fragments (e.g., protospacers), combinations, or any strain specific genetic variant thereof. It would be well understood by one of skill in the art that the guide RNA cutting site on the genome is composed of a 20 bp protospacer, typically followed by 3 pb PAM sequence (NGG, wherein N can be any nucleotide) and that the 20 bp protospacer is used as the guide RNA that pairs with Cas9 to make the genomic cut. It is also well established that truncation of the first 1-3 bp of a protospacer (e.g., truncated gRNA ("tru-gRNA")) can achieve similar cutting effects. See. e.g., Fu Y., et al. (2014) Nature, 32(3), 279-284. For tru-gRNAs, the genomic target sequences are considered identical if the last 17-19 bp of the gRNAs are identical and the first 1-3 bp truncated. In some embodiments, the agent comprises at least three guide RNAs, wherein the three guide RNA sequences comprise the nucleotide sequence of SEQ ID NOs: 1-3. In other embodiments, at least one guide RNA comprises the nucleotide sequence of any one of SEQ ID NOs: 35, 36, 48, 99, 101, 102, 106, 108, 111, 113, fragments (e.g., protospacers), any strain specific genetic variant or any combinations thereof.

In some embodiments, the agent comprises at least two guide RNAs, at least three guide RNAs, at least four guide RNAs, at least five guide RNAs, at least six guide RNAs, at least seven guide RNAs, at least eight guide RNAs, at least nine guide RNAs, at least 10 guide RNAs, at least 11 guide RNAs, at least 12 guide RNAs, at least 13 guide RNAs, at least 14 guide RNAs, at least 15 guide RNAs, at least 60 guide RNAs, at least 17 guide RNAs, at least 18 guide RNAs, at least 19 guide RNAs, at least about 20 guide RNAs, at least 3 about 0 guide RNAs, at least about 40 guide RNAs, at least about 50 guide RNAs, at least about 60 guide RNAs, at least about 70 guide RNAs, at least about 80 guide RNAs, at least about 90 guide RNAs, at least about 100 guide RNAs, or more.

In some embodiments, the agent comprises at least two guide RNAs. In some embodiments, using at least two guide RNAs results in at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of the PERVs in the cell becoming inactive. In some embodiments, using at least two guide RNAs results in at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of cells in a population of cells being at least about 95%, about 96%, about 97%, about 98%, about 99% or 100% PERV inactivated. Non-limiting combinations of guide RNAs include, for example, the combinations listed in the table below.

| | SEQ ID Nos. |
|---|---|
| Set 1: | 37, 169 |
| Set 2: | 48, 94 |
| Set 3: | 93, 179 |
| Set 4: | 94, 112 |
| Set 5: | 87, 157 |
| Set 6: | 95, 96, |
| Set 7: | 45, 50 |
| Set 8: | 99, 95 |
| Set 9: | 74, 127 |
| Set 10: | 99, 111 |
| Set 11: | 33, 103 |
| Set 12: | 96, 102, |
| Set 13: | 93, 167 |
| Set 14: | 48, 102 |
| Set 15: | 39, 118 |
| Set 16: | 111, 112 |
| Set 17: | 67, 119 |
| Set 18: | 110, 112 |
| Set 19: | 69, 142 |
| Set 20: | 102, 111 |

In some embodiments, the agent comprises at least three guide RNAs. In some embodiments, using at least three guide RNAs results in at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of the PERVs in the cell becoming inactive. In some embodiments, using at least three guide RNAs results in at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of cells in a population of cells being at least 95%, 96%, 97%, 98%, 99% or 100% PERV inactivated. Non-limiting combinations of guide RNAs include, for example, the combinations listed in the table below.

| | SEQ ID Nos. |
|---|---|
| Set 1: | 69, 92, 168 |
| Set 2: | 99, 102, 111 |
| Set 3: | 40, 80, 111 |
| Set 4: | 96, 102, 112 |
| Set 5: | 27, 100, 118 |
| Set 6: | 95, 96, 102 |

-continued

| | SEQ ID Nos. |
|---|---|
| Set 7: | 33, 69, 80 |
| Set 8: | 94, 99, 102 |
| Set 9: | 43, 112, 127 |
| Set 10: | 96, 99, 102 |
| Set 11: | 50, 67, 111 |
| Set 12: | 94, 96, 102 |
| Set 13: | 132, 135, 161 |
| Set 14: | 48, 94, 111 |
| Set 15: | 66, 76, 138 |
| Set 16: | 95. 96, 99 |
| Set 17: | 27, 49, 108 |
| Set 18: | 94, 102, 112 |
| Set 19: | 90, 134, 143 |
| Set 20: | 48, 94, 96 |

In some embodiments, the agent comprises at least four guide RNAs. In some embodiments, using at least four guide RNAs results in at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of the PERVs in the cell becoming inactive. In some embodiments, using at least four guide RNAs results in at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of cells in a population of cells being at least 95%, 96%, 97%, 98%, 99% or 100% PERV inactivated. Non-limiting combinations of guide RNAs include, for example, the combinations listed in the table below.

| | SEQ ID Nos. |
|---|---|
| Set 1: | 34, 124, 127, 161 |
| Set 2: | 104, 110, 111, 112 |
| Set 3: | 113, 118, 129, 171 |
| Set 4: | 102, 104, 110, 112 |
| Set 5: | 60, 67, 155, 170 |
| Set 6: | 99, 102, 104, 111 |
| Set 7: | 28, 101, 123, 126 |
| Set 8: | 96, 99, 102, 111 |
| Set 9: | 50, 66, 132, 173 |
| Set 10: | 95, 99, 102, 112 |
| Set 11: | 34, 76, 155, 163 |
| Set 12: | 48, 94, 96, 102 |
| Set 13: | 45, 117, 124, 180 |
| Set 14: | 102, 104, 111, 112 |
| Set 15: | 69, 122, 128, 178 |
| Set 16: | 48, 94, 96, 110 |
| Set 17: | 42, 63, 150, 177 |
| Set 18: | 48, 94, 99, 102 |
| Set 19: | 42, 92, 145, 172 |
| Set 20: | 48, 95, 96, 102 |

In some embodiments, the agent comprises at least five guide RNAs. In some embodiments, using at least five guide RNAs results in at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of the PERVs in the cell becoming inactive. In some embodiments, using at least five guide RNAs results in at least about 30%, about 35%, about 40%, about 45%, about 50%, about 55%, about 60%, about 65%, about 70%, about 75%, about 80%, about 85%, about 90%, about 95%, about 96%, about 97%, about 98%, about 99% or 100% of cells in a population of cells being at least 95%, 96%, 97%, 98%, 99% or 100% PERV inactivated. Non-limiting combinations of guide RNAs include, for example, the combinations listed in the table below.

| | SEQ ID Nos. |
|---|---|
| Set 1: | 51, 113, 137, 160, 169 |
| Set 2: | 49, 67, 102, 171, 179 |
| Set 3: | 53, 94, 111, 134, 145 |
| Set 4: | 49, 68, 102, 171, 174 |
| Set 5: | 45, 49, 54, 102, 115 |
| Set 6: | 33, 55, 83, 108, 133 |
| Set 7: | 85, 90, 119, 137, 170 |
| Set 8: | 58, 65, 67, 74, 115 |
| Set 9: | 65, 55, 83, 99, 133 |
| Set 10: | 37, 44, 59, 136, 178 |
| Set 11: | 65, 107, 164, 180, 181 |
| Set 12: | 48, 99, 102, 104, 110, |
| Set 13: | 67, 86, 117, 133, 177 |
| Set 14: | 48, 99, 111, 102, 104 |
| Set 15: | 49, 68, 102, 171, 174 |
| Set 16: | 95, 102, 104, 111, 112 |
| Set 17: | 86, 87, 106, 107, 155 |
| Set 18: | 94, 102, 104, 111, 112 |
| Set 19: | 41, 42, 106, 108, 154 |
| Set 20: | 48, 96, 99, 102, 111 |

In some embodiments, using at least two guide RNAs (e.g., between 2 and 10 guide RNAs) in the PERV KO generates a deletion on the PERV pol sequence. In some embodiments, the deletion is greater than 1 bp, greater than 2 bp, greater than 3 bp, greater than 4 bp, greater than 5 bp, greater than 6 bp, greater than 7 bp, greater than 8 bp, greater than 9 bp, greater than about 10 bp, greater than about 15 bp, greater than about 20 bp, greater than about 25 bp, greater than about 30 bp, greater than about 35 bp, greater than about 40 bp, greater than about 45 bp, greater than about 50 bp, greater than about 55 bp, greater than about 60 bp, greater than about 65 bp greater than about 70 bp, greater than about 75 bp, greater than about 80 bp, greater than about 85 bp, greater than about 90 bp, greater than about 95 bp, greater than about 100 bp, greater than about 125 bp, greater than about 130 bp, greater than about 135 bp, greater than about 140 bp, greater than about 145 bp, greater than about 150 bp, greater than about 200 bp.

In some embodiments, one or more elements of the CRISPR-based agents are derived from a particular organism comprising an endogenous CRISPR system, such as *Streptococcus pyogenes, Staphylococcus aureus, Neisseria meningitidis, Streptococcus thermophilus* or *Treponema denticola*.

In some embodiments, the CRISPR-based agent is a combination of any of the CRISPR, based polypeptides/proteins and CRISPR-based polynucleotides disclosed herein. For example, in some embodiments, the CRISPR-based agent comprises a Cas endonuclease and guide RNA. In some embodiments, the CRISPR-based agent comprises a Cas endonuclease, tracrRNA and tracr-mate sequence. In some embodiments, the tracrRNA and tracr-mate sequence are engineered such that they are in the same molecule. In some embodiments, the CRISPR-based agent is one or more polynucleotides encoding any of the foregoing.

In some embodiments, the CRISPR-based agent is a chimeric RNA such as a CRISPR-Cas system RNA. In some embodiments, the CRISPR-based agent has at least one second guide sequence capable of hybridizing to an RNA sequence of the CRISPR-Cas system or a nucleic acid molecule for expression of a component of the CRISPR-Cas complex to diminish or eliminate functional expression of the system or complex, whereby the system or complex can be self-inactivating; and, the second guide sequence can be capable of hybridizing to a nucleic acid molecule for expression of the CRISPR enzyme.

In some embodiments, the disclosure provides methods for using any of the CRISPR-based agents disclosed herein. In some embodiments, the disclosure provides an effective means for modifying PERV polynucleotide sequences by utilizing any of the CRISPR-based agents disclosed herein. The CRISPR complex of the invention has a wide variety of utilities including modifying (e.g., deleting, inactivating) PERV polynucleotide sequences in different types of cells from various tissues and organs. As such the CRISPR complex of the invention has a broad spectrum of applications in, e.g., gene or genome editing.

In some embodiments, the disclosure provides an in vivo method of genomic editing comprising providing a quantity of one or more vectors each encoding at least one CRISPR protein and one or more guide RNAs (gRNAs), and administering the one or more vectors to a mammal, wherein in vivo expression of the one or more vectors includes binding of the CRISPR protein to a PERV locus cognate to the gRNA and in vivo generation of a double stranded break (DSB) in a population of cells in the mammal, wherein in vivo homologous recombination (HR) of the DSB results in editing of the genome of a population of cells in the mammal. In some embodiments, the CRISPR protein is cas9 and the one or more gRNAs comprise a sequence capable of binding to a protospacer adjacent motif ("PAM"). In some embodiments, HR includes non-homologous end joining (NHEJ) introducing missense or nonsense of a protein expressed at the PERV locus.

In some embodiments, the CRISPR-based agent further comprises a portion that modulates PERV expression. In some embodiments, the CRISPR-based agent is a fusion protein that comprises a transcription repressor domain. In some embodiments, the transcription repressor domain is a Krippel associated box (KRAB).

D. Improving Health/Survival of Genetically Modified Cells

In some embodiments, the health and/or survival of any of the genetically modified porcine cells described herein is compromised as a result of the genetic modification process (e.g., multiplex DNA damage effects). In these situations, it may be advantageous to treat the genetically modified cell or cells with one or more factors that improves the health and/or survival of the genetically modified cell.

In some embodiments, the genetically modified cell or cells are administered both a p53 inhibitor and a growth factor. In certain embodiments, the genetically modified cell or cells are administered both bFGF and pifithrin-alpha.

IV. Methods of Treatment

In some embodiments, any of the genetically modified porcine cells, tissues or organs disclosed herein may be used to treat a non-porcine subject. In some embodiments, the disclosure provides for methods of transplanting any of the genetically modified cells, tissues or organs described herein into a non-porcine subject in need thereof. In some embodiments, the non-porcine subject is a human. In some embodiments, the subject is a non-human primate.

In some embodiments, a genetically modified organ for use in any of the methods disclosed herein may be selected from the heart, lung, brain, liver, basal ganglia, brain stem medulla, midbrain, pons, cerebellum, cerebral cortex, hypothalamus, eye, pituitary, thyroid, parathyroid, esophagus, thymus, adrenal glands, appendix, bladder, gallbladder, small intestine, large intestine, small intestine, kidney, pancreas, spleen, stomach, skin, prostate, testes, ovaries, and/or uterus of the genetically modified pig. In some embodiments, a genetically modified tissue for use in any of the methods disclosed herein may be selected from cartilage (e.g., esophageal cartilage, cartilage of the knee, cartilage of the ear, cartilage of the nose), muscle such as, but not limited to, smooth and cardiac (e.g., heart valves), tendons, ligaments, bone (e.g., bone marrow), cornea, middle ear and veins of the genetically modified pig. In some embodiments, a genetically modified cell for use in any of the methods disclosed herein includes blood cells, skin follicles, hair follicles, and/or stem cells. Any portion of an organ or tissue (e.g., a portion of the eye such as the cornea) may also be administered the compositions of the present invention.

In some embodiments, the disclosure provides for treating a subject having a disease, disorder or injury that results in a damaged, deficient or absent organ, tissue or cell function. In some embodiments, the subject has suffered from an injury or trauma (e.g., an automobile accident) resulting in the damage of one or more cells, tissues or organs of the subject. In some embodiments, the subject has suffered a fire or acid burn. In some embodiments, the subject has a disease or disorder that results in a damaged, deficient or absent organ, tissue or cell function. In some embodiments, the subject is suffering from an autoimmune disease. In some embodiments, the disease is selected from the group consisting of: heart disease (e.g., atherosclerosis), dilated cardiomyopathy, severe coronary artery disease, scarred heart tissue, birth defects of the heart, diabetes Type I or Type II, hepatitis, cystic fibrosis, cirrhosis, kidney failure, lupus, scleroderma, IgA nephropathy, polycystic kidney disease, myocardial infarction, emphysema, chronic bronchitis, bronchiolitis obliterans, pulmonary hypertension, congenital diaphragmatic hernia, congenital surfactant protein B deficiency, and congenital cystic emphysematous lung disease, primary biliary cholangitis, sclerosing cholangitis, biliary atresia, alcoholism, Wilson's disease, hemochromatosis, and/or alpha-1 antitrypsin deficiency.

In some embodiments, any of the genetically modified cells, tissues and/or organs of the disclosure are separated from the genetically modified donor pig and administered into a non-porcine subject host. "Administering" or "administration", as used in this context, includes, but is not limited to, introducing, applying, injecting, implanting, grafting, suturing, and transplanting. According to the disclosure, the genetically modified cells, tissues and/or organs may be administered by a method or route which results in localization of the organs, tissues, cells or compositions of the invention at a desired site. The organs, tissues, cells or compositions of the invention can be administered to a subject by any appropriate route which results in delivery of the cells to a desired location in the subject where at least a portion of the cells remain viable. In some embodiments, at least 10%, 20%, 30%, 40%, 50%, 60%, 70%, 80%, 90%, or 100% of the cells (whether administered separately or as part of a tissue or organ) remain viable after administration to the subject. Methods of administering organs, tissues, cells or compositions of the invention are well-known in the art. In some embodiments, the cells, tissues and/or organs are transplanted into the host. In some embodiments, the cells, tissues and/or organs are injected into the host. In some embodiments, the cells, tissues and/or organs are grafted onto a surface of the host (e.g., bone or skin).

In some embodiments, it will be necessary to protect the genetically modified cell(s), tissue(s) or organ(s) from the immune system of the host to whom the genetically modified cell(s), tissue(s) or organ(s) are being administered. For example, in some embodiments, the genetically modified cell(s), tissue(s) or organ(s) is administered with a matrix or coating (e.g., gelatin) to protect the genetically modified cell(s), tissue(s) or organ(s) from an immune response from the host. In some embodiments, the matrix or coating is a biodegradable matrix or coating. In some embodiments, the matrix or coating is natural. In other embodiments, the matrix or coating is synthetic.

In some embodiments, the genetically modified cell(s), tissue(s) or organ(s) is administered with an immunosuppressive compound. In some embodiments, the immunosuppressive compound is a small molecule, a peptide, an antibody, and/or a nucleic acid (e.g., an antisense or siRNA molecule). In some embodiments, the immunosuppressive compound is a small molecule. In some embodiments, the small molecule is a steroid, an mTOR inhibitor, a calcineurin inhibitor, an antiproliferative agent or an IMDH inhibitor. In some embodiments, the small molecule is selected from the group consisting of corticosteroids (e.g., prednisone, budesonide, prednisolone), calcineurin inhibitors (e.g., cyclosporine, tacrolimus), mTOR inhibitors (e.g., sirolimus, everolimus), IMDH inhibitors (azathioprine, leflunomide, mycophenolate), antibiotics (e.g., dactinomycin, anthracyclines, mitomycin C, bleomycin, mithramycin) and methotrexate, or salts or derivatives thereof. In some embodiments, the immunosuppressive compound is a polypeptide selected from the group consisting of: CTLA4, anti-b7 antibody, abatacept, adalimumab, anakinra, certolizumab, etanercept, golimumab, infliximab, ixekizumab, natalizumab, rituximab, seckinumab, tocilizumab, ustekinumab, vedolizumab, basiliximab, daclizumab, and murmonab.

In some embodiments, the genetically modified cell(s), tissue(s) or organ(s) to be administered to the subject have been further genetically modified such that they are less likely to induce an immune response in the subject. In some embodiments, the genetically modified cell(s), tissue(s) or organ(s) have been further genetically modified such that they do not express functional immunostimulatory molecules.

EXAMPLES

The disclosure now being generally described, it will be more readily understood by reference to the following examples, which are included merely for purposes of illustration of certain aspects and embodiments of the present disclosure, and are not intended to limit the disclosure. For example, the particular constructs and experimental design disclosed herein represent exemplary tools and methods for validating proper function. As such, it will be readily apparent that any of the disclosed specific constructs and experimental plan can be substituted within the scope of the present disclosure.

Example 1. PERVs Infect, Replicate, and Propagate in Human Cells

Figure 4A:
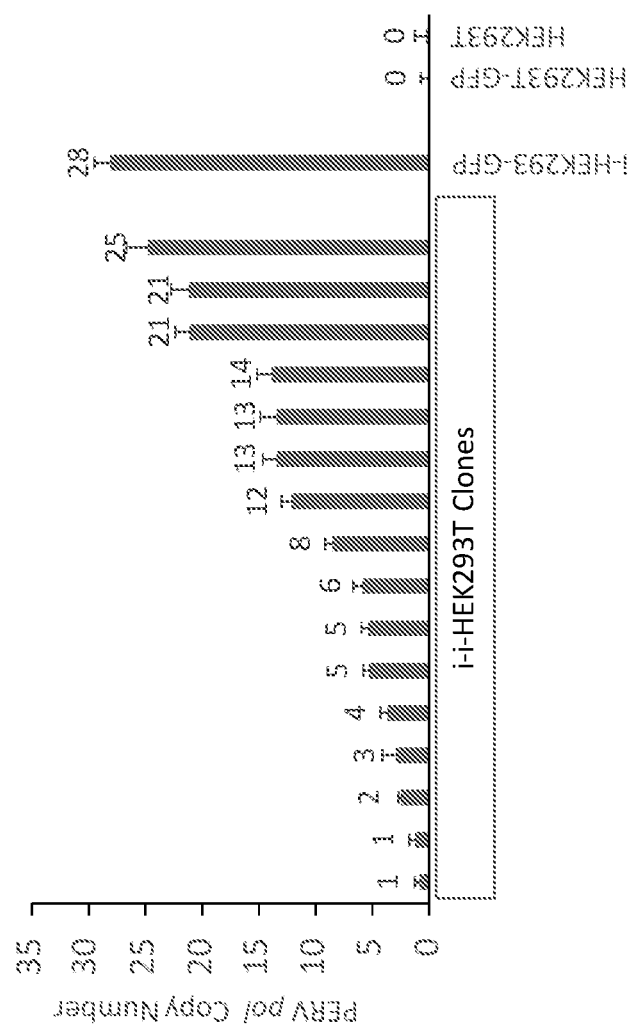
FIG. 4A shows PERV copy number in selected clones of iHEK293T-GFP. WT HEK293T (non-GFP) cells were co-cultured with equivalent number of cells of PERV infected HEK293T-GFP (i-HEK293T-GFP) clone 10 for two weeks. The GFP-negative single human cells were isolated by flow cytometry based on GFP signal. After the single cell colony grew up, genomic DNA was amplified via qPCR to detect and quantify PERV elements in the GFP-negative clones using i-HEK293T-GFP clone 10 PERV copy number as a standard marker (PERV copy number of clone 10 has been detected by ddPCR previous to the co-coculture experiment). PERV transmission from i-HEK293T-GFP clone 10 to WT HEK293T human cells was detected by qPCR of PERV pol gene and different WT HEK293T clones showed different copy number of PERVs.
Figure 4B:
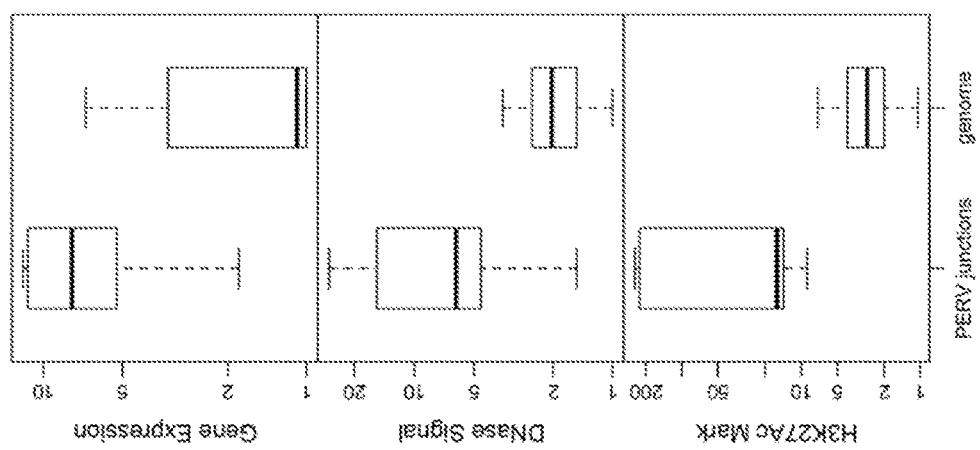
FIG. 4B shows that PERVs insert preferentially in open chromatin and transcriptionally active areas. Gene expression levels, DNase signal, and H3K27Ac signals between areas around PERVs insertion sites and the remaining junctions were measured and compared. Increased transcription, DNase signal, and H3K27Ac levels in PERVs insertion sites was observed.

Clinicians have feared that PERVs present in a pig donor organ or tissue could infect the cells of a human host. In order to determine if PERV remained active and propagated in human cells following infection, the PERV copy number was monitored both in a population and in clones of PERV-infected HEK293T-GFP cells (i-HEK293T-GFP) for more than 4 months. The PERV copy number increased over time (FIG. 1A) as determined by droplet digital PCR (ddPCR). There are three major subtypes of PERVs: PERV-A, PERV-B, and PERV-C. Subtypes A and B are ubiquitous and have been reported to be transmittable from pigs to humans, whereas subtype C is only present in some pig strains and can only be transmitted among pigs (Patience et al., 2001, J. Virol., 75, 2771-5). Consistent with previous reports, PERV-A and PERV-B were detected in the infected human cells (data not shown), confirming that they are humantropic. However, PERV-C was not detected in either PK15 or i-HEK293T-GFP cells (data not shown). To determine whether the PERVs integrate into the human genome or remain episomal in the infected human cells, junction capture sequencing was performed on the infected clonal i,HEK293T-GFP cells. Novel PERV junctions were detected in the human genome. These PERV junctions are overrepresented in intragenic regions (15 out of 22 detected junctions) (FIG. 1B). In addition, PERV insertion sites have markedly higher transcription levels, DNase sensitivity, and H3K27 acetylation than randomly chosen genomic locations (FIG. 4B), suggesting that PERVs tend to integrate into transcriptionally active regions.

Figure 1C:
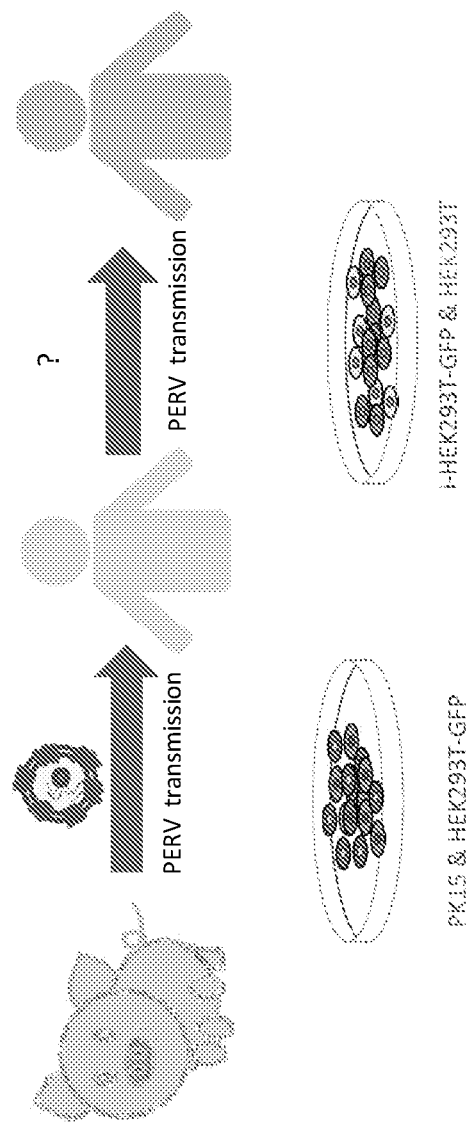
FIG. 1C shows a simplified schematic of the experimental design used to examine human-to-human PERVs transmission, PERVs-infected with human HEK293T cell labeled with GRP (i-HEK293T-GFP) were co-cultured with unlabeled WT HEK293T (HEK293T) for 14 days. The HEK293T clones were isolated from the co-culture and genomic DNA was extracted to determine whether the HEK293T clones were infected by PERV from i-HEK293T-GFP cells.
Figures 1D, 1E:
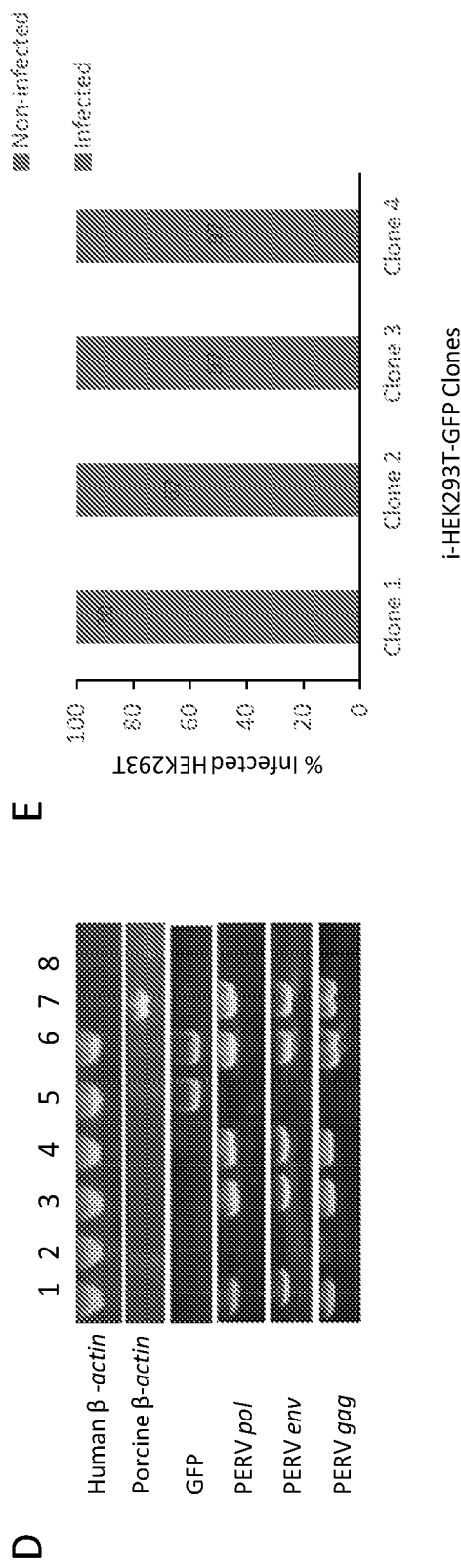
FIG. 1D shows the detection of human-to-human PERV transmission, individual clones of HEK293T were grown from the single cells isolated from the co-culture of i-HEK293T-GFP with HEK293T through flow cytometry. The PCR gel image shows that 3 out of 4 randomly tested HEK293T clones contained PERV sequences (PERV pol, env, and gag), but no sequence of GFP or pig genomic DNA (tested by pig specific GGTA). Sample orders are: 1) HEK293T clone 1; 2) HEK293T clone 2; 3) HEK293T clone 3; 4) HEK293T clone 4; 5) HEK293T-GFP control; 6) i-HEK293T-GFP; 7) PK15 WT; and 8) negative control.
FIG. 1E illustrates that different i-HEK293T-GFP clones have different infectious potential. The percentages of infected HEK293T clones from the co-culture of i-HEK293T-GFP and WT HEK2931 varied from 20% to 97%. The percentage corresponds to the PERV copy number of i-HEK293T-GFP clones in the culture. The PERV copy number of the 4 parent i-HEK293T-GFP clones are: 15, 28, 27 and 28, respectively.

In order to determine if the increased copy number of PERVs in i-HEK293T-GFP clones is caused by intracellular PERV replication or by intercellular PERV transmission among human cells, clonal i-HEK293T-GFP cells were co-cultured with WT HEK293T cells for two weeks. The PERV elements were subsequently assessed in the co-cultured WT clones via PCR (FIGS. 1C and 1D). The presence of PERV pol, env, and gag genes was detected in WT HEK293 cells with no history of contact with porcine cells. The percentage of infected WT HEK293T cells varies from 18% to 97%, with the lower and higher percentages corresponding, respectively, to lower and higher PERV copy numbers in the parent i-HEK293T-GFP clones in the co-culture (FIG. 1E). These results indicate that infected human cells can transmit PERVs to fresh human cell populations. Therefore, there is a risk of PERV transmission to human hosts in the context of xenotransplantation, confirming the need to eliminate this risk by producing PERV-free pigs.

Example 2. PERV-Free Primary Porcine Cells

Generating PERV-free pigs involves production of primary porcine cells devoid of PERV activity, which can be cloned via somatic cell nuclear transfer (SCNT) to produce porcine fetal fibroblast cell line (FFF3) was selected to be modified to create PERV-free primary porcine cells. First, PERVs present in the FFF3 genome were mapped and characterized. The copy number of functional PERVs was estimated to be ~25, as determined by ddPCR on the reverse transcriptase (pol) gene (data not shown). The estimated PERV copy number was close to the sum of 10 copies of the PERV-A env gene, 14 copies of the PERV-B env gene, and 0 copies of the PERV-C env gene which was identified in the genome (data not shown). Using whole genome sequencing, one copy of truncated PERV-B was detected. This truncated PERV-B was previously not detectable by ddPCR (data not shown).

Figure 2A:
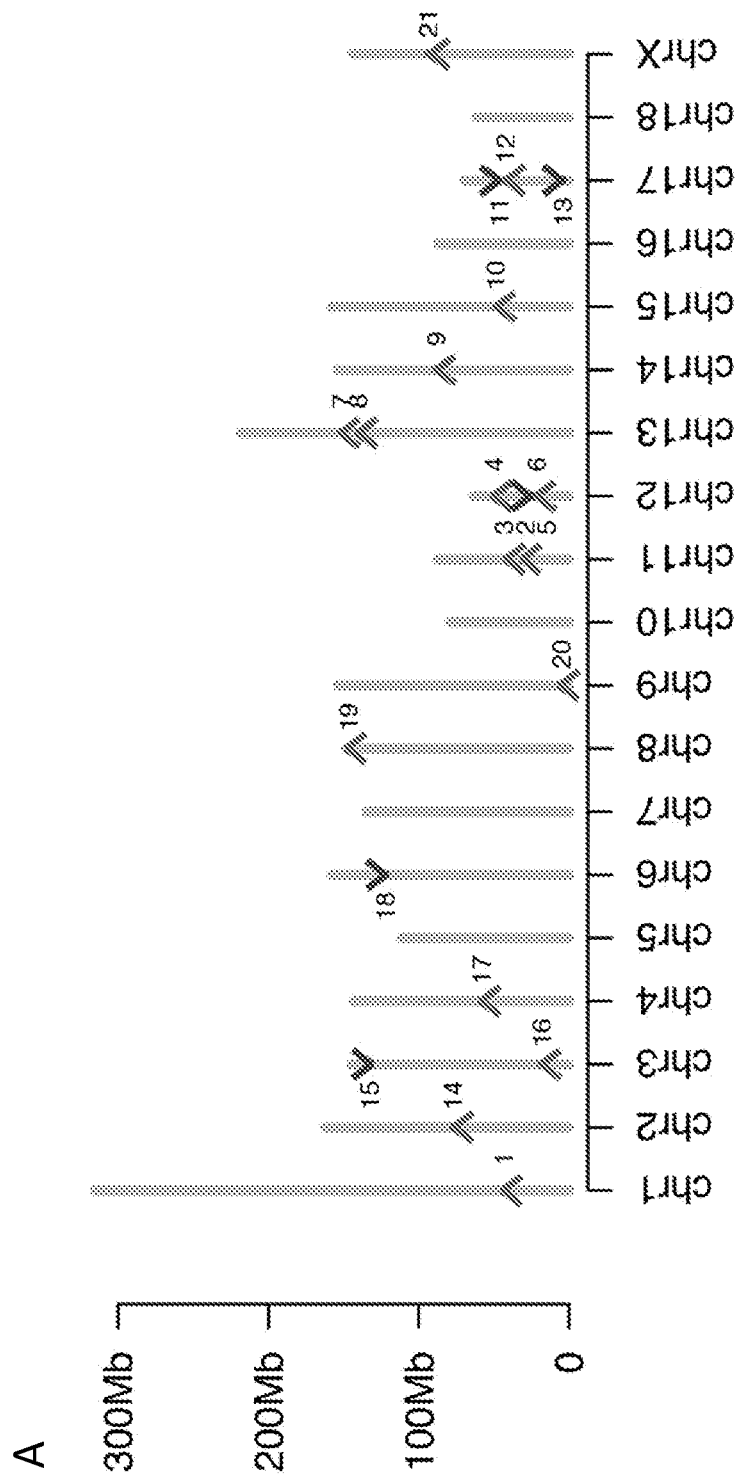
FIG. 2A shows chromosome mapping of PERV insertion sites. PERV integration sites on the chromosome were detected in the WT FFF3 cell line using hybridization capture and long reads Pacbio sequencing. Gray bars represent chromosomal scaffolds. Arrows (pointing up) represent PERVs in forward or plus chromosome strand. Arrows (pointing down) represent PERVs in the reverse or negative strand.
Figures 2B, 2C:
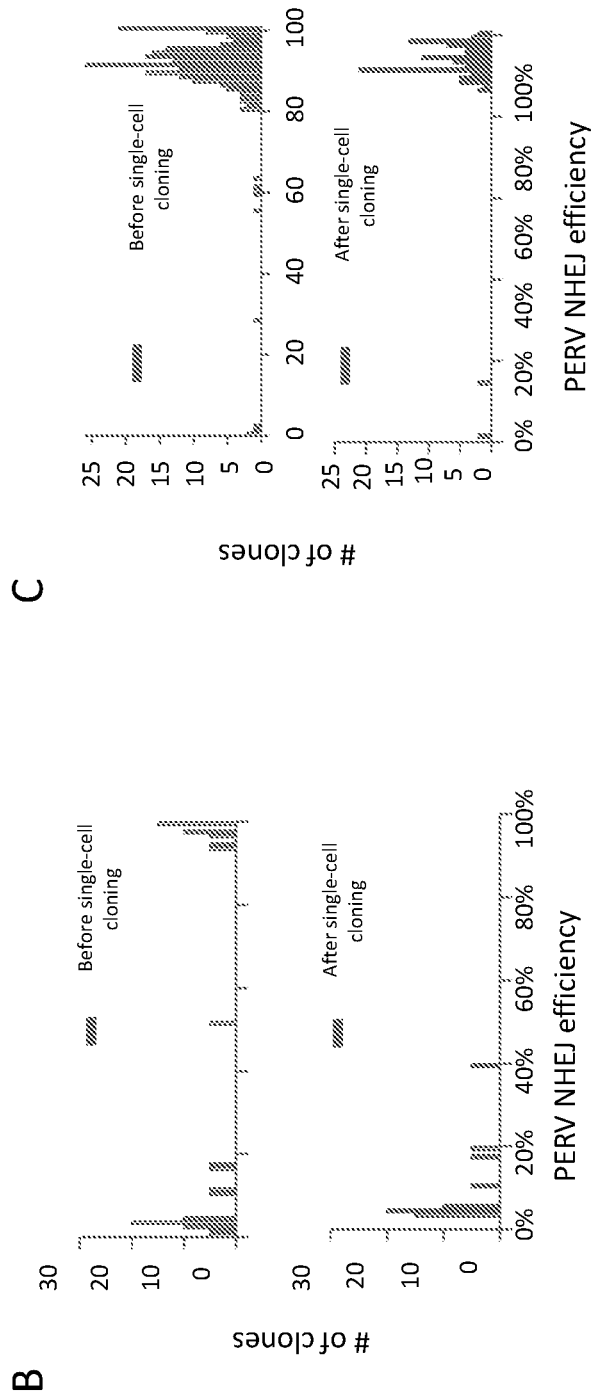
FIG. 2B graphs the survival of highly modified FFF3 clones. After targeting the PERVs in FFF3, single cells were sorted and immediately genotyped. A bimodal distribution of PERV targeting frequencies among single cells was observed (upper panel). 100% PERV-free FFF3 cells were present among the single cells directly genotyped. However, this pattern changed after expansion of the single cells (bottom panel). Among the single cell clones, only the ones with lower efficiency (<, 39%, the average targeting efficiency in the population was 37%) were obtained, and the persistence of some FFF3 clones that did not have 100% eradication of PERVs was observed (lower panel).
FIG. 2C shows treatment with PFTα and bFGF sustains the growth of highly modified FFF3 clones. The combined use of an inhibitor of p53 and a growth factor rescues the highly edited cells. A population of FFF3 was treated with PFTα, and bFGF during the gene editing experiment; then, single cells were sorted for direct genotyping and for colony growth, Followed genotyping. Both the single cells and expanded clones showed similar bimodal distribution in PERV targeting efficiency, and highly modified clones survived under this condition.

PacBio long-reads genome sequencing (N50=2,439 bp) were performed after PERVs-specific hybridization capture. The results mapped 21 copies of PERVs to non-repetitive regions of the genome (FIG. 2A). Two additional copies were mapped to repetitive regions, and 2 could not be mapped to the current pig genome assembly (11% gaps, *Sus scrofa* build 10.2) (Groenen et al., 2012, Nature, 491:393-8). To target these PERVs for inactivation, three CRISPR guide RNAs (gRNAs) specific to the catalytic core of the PERV pol gene were designed having the sequences of SEQ ID NOs: 1-3, respectively. After treating a population of FFF3 cells with CRISPR-Cas9 and the three gRNAs for twelve days, 37% of the PERV pol loci had acquired inactivating mutations. Interestingly, results showed a bimodal distribution of targeting efficiency among single cells. About 34% (8 out of 23) single cells had high editing efficiency (>90%) and 60% (14 out of 23) single cells had low editing efficiency (<20%). This is presumably the result of gene conversion (Yang et al., 2015, Science, 80:350) for repetitive sequence targeting. Surprisingly, despite the presence of highly modified cells in the population, the above-mentioned procedure did not yield any single-cell FFF3 clones with high efficiency (FIG. 2B).

Figures 2D, 2E:
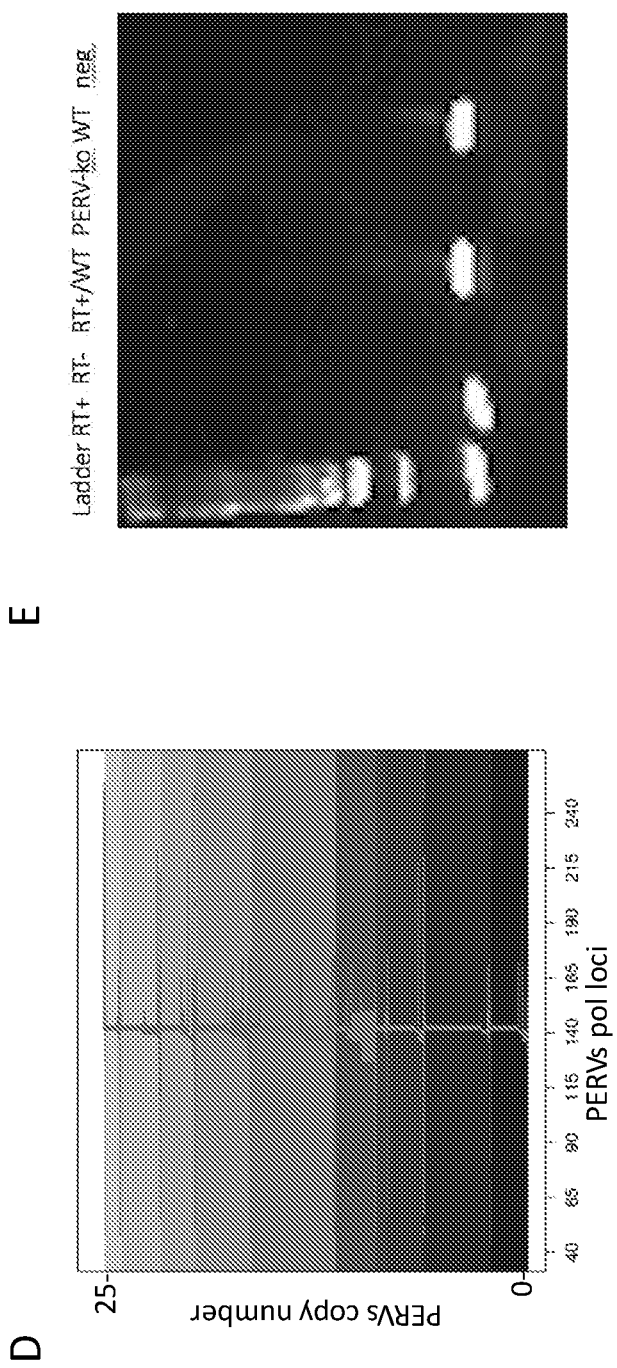
FIG. 2D shows haplotypes of one of the 100% PERV-free clones at PERV poi loci after CRISPR-Cas9 treatment. Several 100% PERV-free clones were achieved from the PFTα and bFGF treated FFF3 population. The y-axis indicates the edited PERVs loci. The x-axis indicates the relative locations of the indels within the PERV loci. Aligned indel events in the PERV poi sequence are represented in red. Shades of purple indicate different haplotypes of PERVs.
FIG. 2E shows that PERV production is eliminated in 100% PERV modified clones. The reverse transcriptase (RT) activity of PERV particles presented in the cell culture supernatant was detected by a reverse transcription assay. The results demonstrated no PERV production in 100% PERV-free clone supernatant, whereas the supernatant of WT FFF3 cells showed significant RT activity. The sample order from left to right: 2-log DNA ladder (New England Biolabs); RT+(using commercial reverse transcriptase (RT)); RT-(no RT enzyme); RT+/FF WT (commercial RT enzyme plus WT 3FFF lysis (lysis of virus pellet from 3FFF culture media); 100% FFF3 (100% PERV-inactivated FFF3 clone lysis); WT FF (WT 3FFF lysis); neg (no lysis or RT enzyme, no RNA template).
Figure 5A:
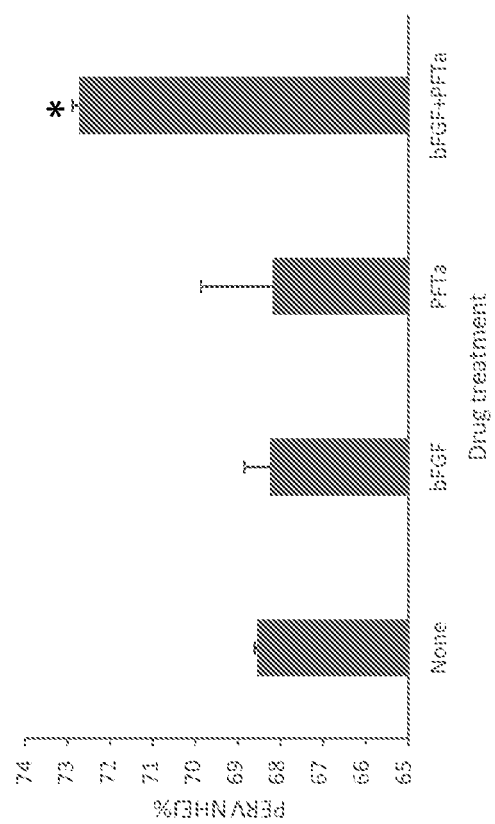
FIG. 5A is a graph illustrating the effects of modulators of DNA damage effects. FFF3 cells were treated with bFGF, PFTa, and bFGF+PFTa. Treatment with both the bFGF and PFTa alone did not increased PERV editing efficiency, whereas treatment with a cocktail of bFGF and PFTa significantly enhanced the targeting frequency (p-value=0.0016), demonstrating there exists a synergistic effect between bFGF and PFTa.
Figure 5B:
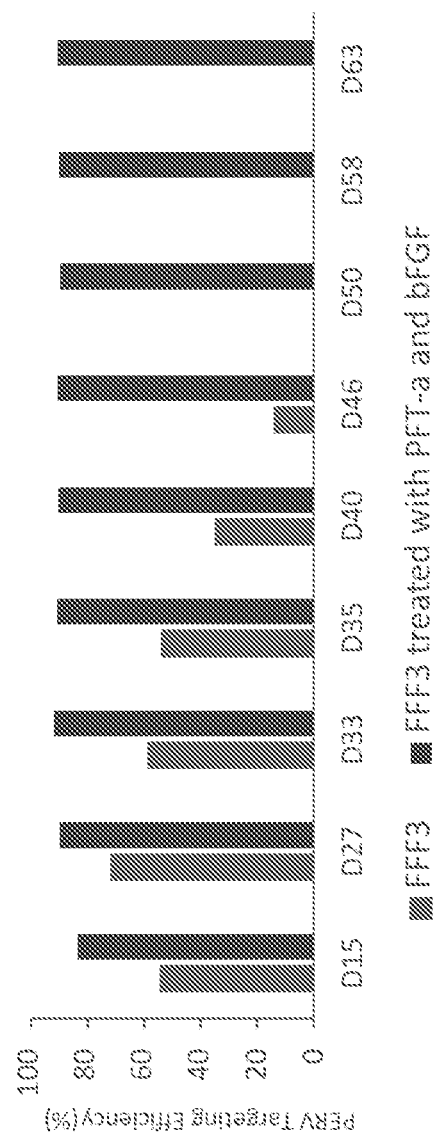
FIG. 5B is a graph illustrating the effect of treatment with a cocktail of PFT-a and bFGF on a population of FFF3-#5 over time (I)=days). Results showed a sustained high PERV targeting efficiency, whereas a population of FFF3-#4 that was not treated with the cocktail showed a decreased pattern of PERV editing efficiency. (ANOVA, day (p-value=0.23), PFTa/bFGF treatment (p-value=0.00002)).
Figure 5C:
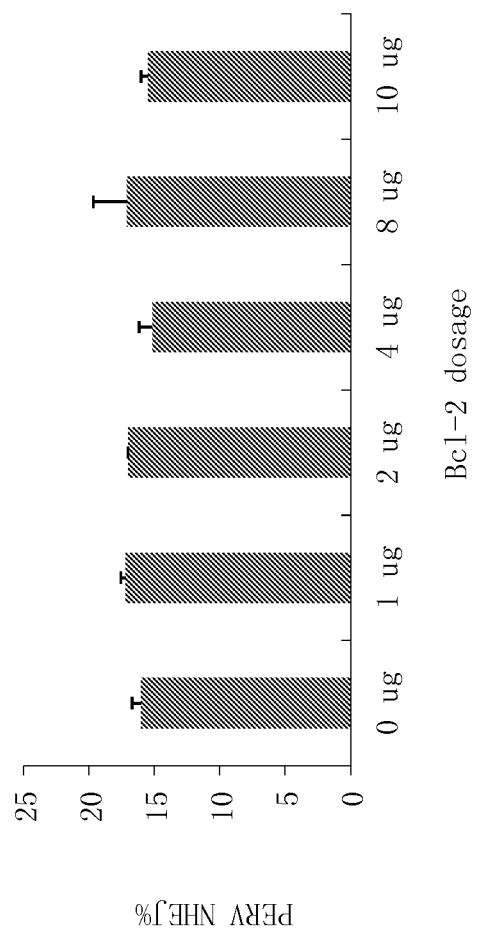
FIG. 5C is a graph illustrating the effects of seven days of treatment with bcl-2 on FFF3 cells. No significant difference (p-value=0.565) among treatments with different dosages of Bcl-2 was detected. Dose-dependent cytotoxicity of Bcl-2 was also observed during the experiment.
Figure 6A:
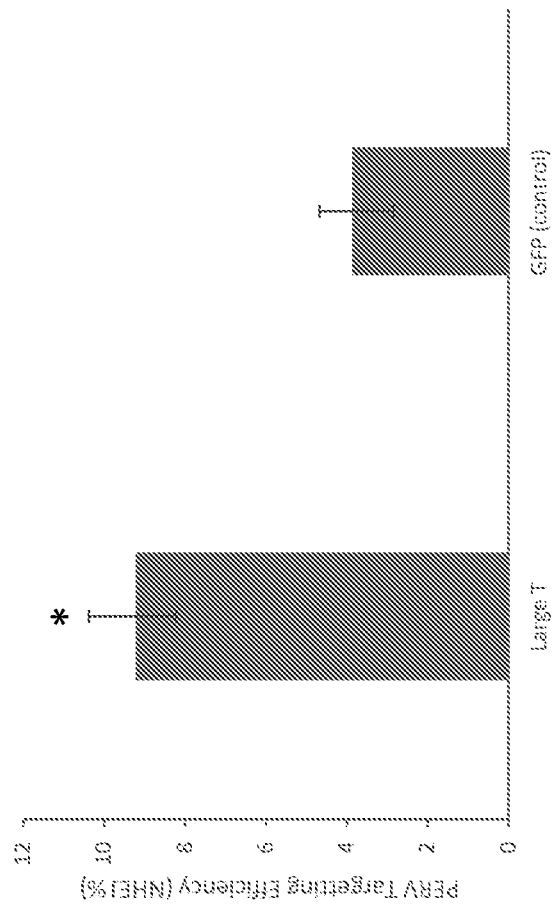
FIG. 6A is a graph illustrating the effects of the large T antigen on targeting efficiency of PERVs in FFF3 population (p-value=0.05, Wilcoxon Test (One sided)).

In order to determine if simultaneous DNA cleavages by Cas9 at multiple sites in the FFF3 genome could trigger DNA damage-induced senescence or apoptosis, the inhibition of senescence and/or apoptosis pathways were examined to determine if they could increase the targeting efficiency in FFF3 populations and enhance viability of the highly modified clones. The application of a cocktail containing p53 inhibitor, pifithrin alpha (PFTα), and growth factor bFGF during genetic modification resulted in significantly increased average targeting efficiency of the resulting FFF3 populations (FIG. 5A (ANOVA, p=0.0000$^2$), FIG. 5B). In addition, transiently over-expressing SV40 large T antigen, an inhibitor of both p53 and Rb pathways, also resulted in increased average targeting efficiency (FIG. 6A, one-sided Wilcoxon test, p=0.05). On the contrary, overexpression of Bcl-2, an apoptosis inhibitor, did not increase the average targeting efficiency (FIG. 5C, ANOVA, p=0.565). A PFTα and bFGF cocktail was used because of its higher efficiency, lower cytotoxicity, and ease of control. Using this optimized cocktail, 100% PERV-inactivated FFF3 cells were isolated from the population treated with CRISPR-Cas9 (FIGS. 2C, 2D).

Figure 7:
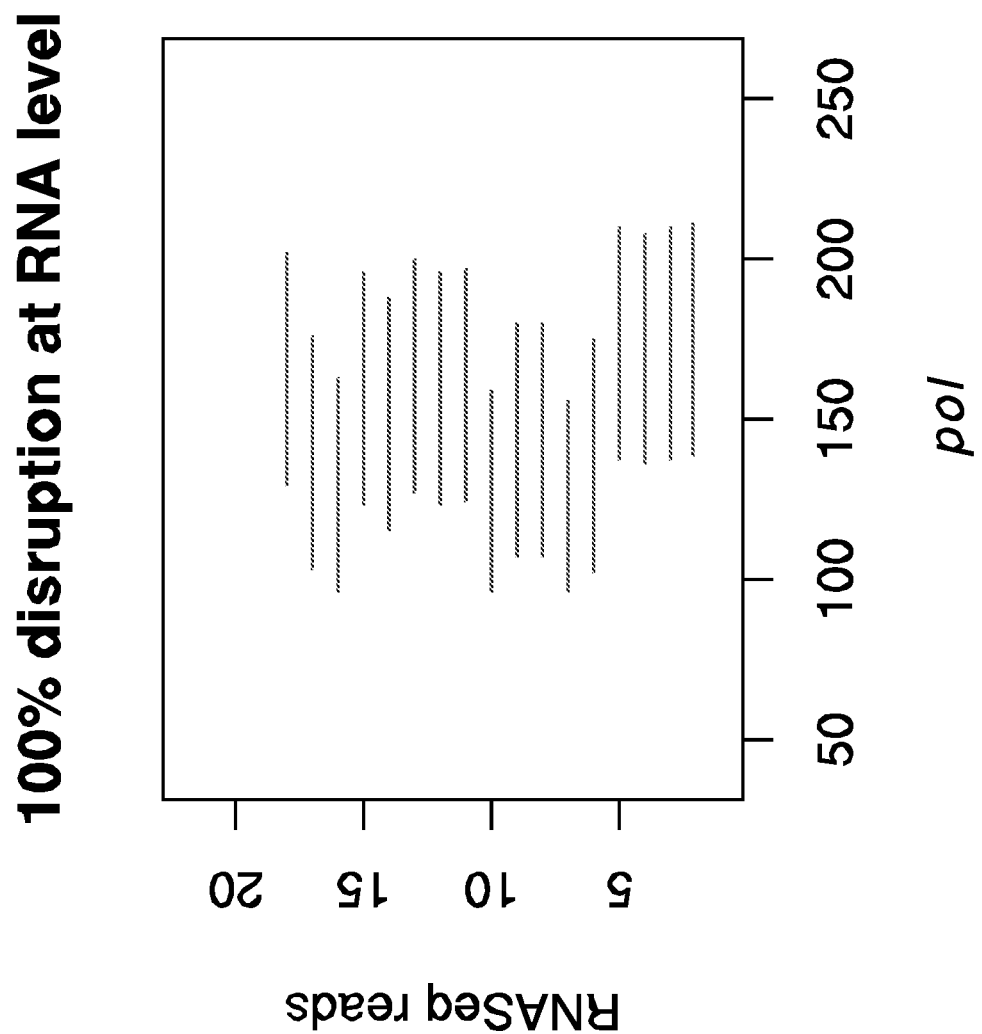
FIG. 7 shows the transcription profile of 100% PERV-free PFFF3. RNAseq was used to analyze PERVs inactivation of pol gene. The y-axis indicates the sites. The X-axis indicates the relative locations of the indels within the PERV loci. In red, aligned indel events in the PERV pol sequence are represented.

RNA-seq (FIG. 7) was performed on 100% PERV-inactivated FFF3 clones. The results confirmed that all pol transcripts had been mutated. Furthermore, the effect of genome-wide disruption of PERV pol and its role in in vitro production of PERVs from FFF3 was examined. There was no detection of reverse transcriptase (RT) activity of PERVs in the cell culture supernatant of the 100% PERV-inactivated FFF3 (FIG. 2E). Furthermore, strong RT activity was observed in WT FFF3, suggesting that modified cells produced few or no PERV particles.

In order to examine off-target effects of CRISPR-Cas9 in the 100% PERV-inactivated cells, karyotyping was conducted. The karyotyping results showed normal chromosomal structures (data not shown). To examine chromosomal integrity with higher resolution, junction PCR reactions were conducted to check the integrity of all PERV genomic junctions on one side that would be lost in PERV-PERV deletions. All tested junctions remained intact, which indicates that no PERV-PERV deletions were detected in these regions. Primers used in the junction PCR reactions are indicated in FIG. 8. Therefore, there was no detection of off-target effects or on-target genomic damage caused by CRISPR-Cas9 in the 100% PERV-inactivated FFF3.

Example 3. PERV-Free Embryos

Having obtained FFF3 cells with 100% eradication of PERV activity, PERV-free embryos were then produced using SCNT. Using hand-made pig cloning (Du et al., 2007, Theriogenology, 68:1104-10), porcine embryos with 50-78% efficiency were successfully cloned. These embryos grew for seven days in culture and reached blastocyst stage. Normal blastocyst structure was observed. Furthermore, the pluripotency of inner cell mass (SOX2+) was validated on day 7 (FIG. 3A).

Figure 3B:
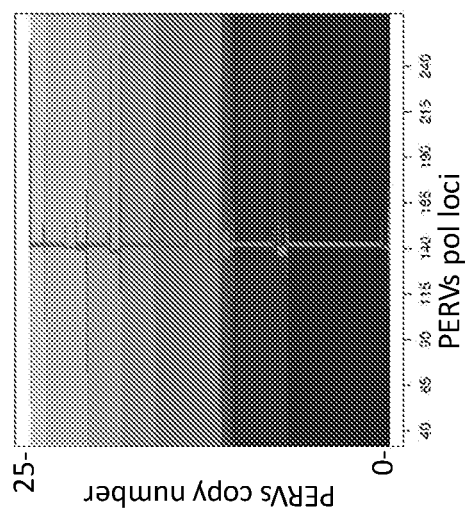
FIG. 3B shows PERV targeting efficiency of fetus cloned from 100% PERV-free PFFF3. The y-axis indicates the edited PERVs loci. The x-axis indicates the relative locations of the indels within the PERV loci. Aligned indel events in the PERV pol sequence are represented in red. Shades of purple indicate different PERV haplotypes.

Using the PERV-free FFF3 cell line, additional rounds of pig cloning were conducted through somatic cell nuclear transfer, and implanted in surrogate mothers (250 embryos transferred). At day 49 after embryo transfer, the fetuses were collected from one surrogate sow by C-section. Four live fetuses were isolated from the sow. The PERV inactivation levels and PERV copy number were checked by ddPCR. The results showed there is no reinfection of PERV in the fetuses produced from the PERV-free cell line (FIG. 3B). The fetuses exhibited the same PERV inactivation efficiency (100%, FIG. 3B) and PERV copy number (data not shown) as its originated PERV-free cell line. Using the cell line derived from the PERV-free fetus, the second round of pig cloning was conducted.

Example 4. PERV-Free Piglets

Figure 9:
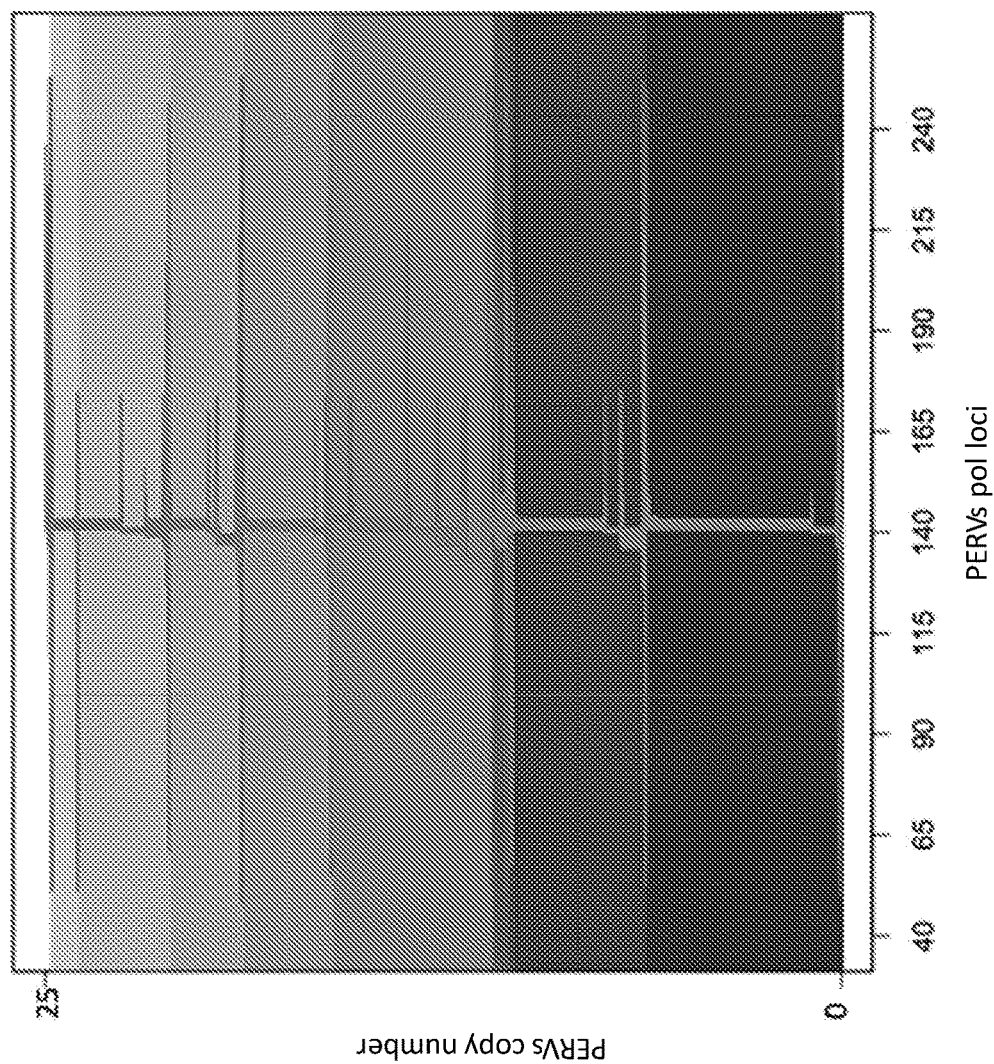
FIG. 9 shows PERV targeting efficiency of a piglet born PERV-free FFF3. The y-axis indicates the edited PERVs loci. The x-axis indicates the relative locations of the indels within the PERV loci. Aligned indel events in the PERV pol sequence are represented in red. Shades of purple indicate different PERVs haplotypes. The genotype of the pig showed that all the 25 copies of PERVs were functionally mutated.
Figure 10:
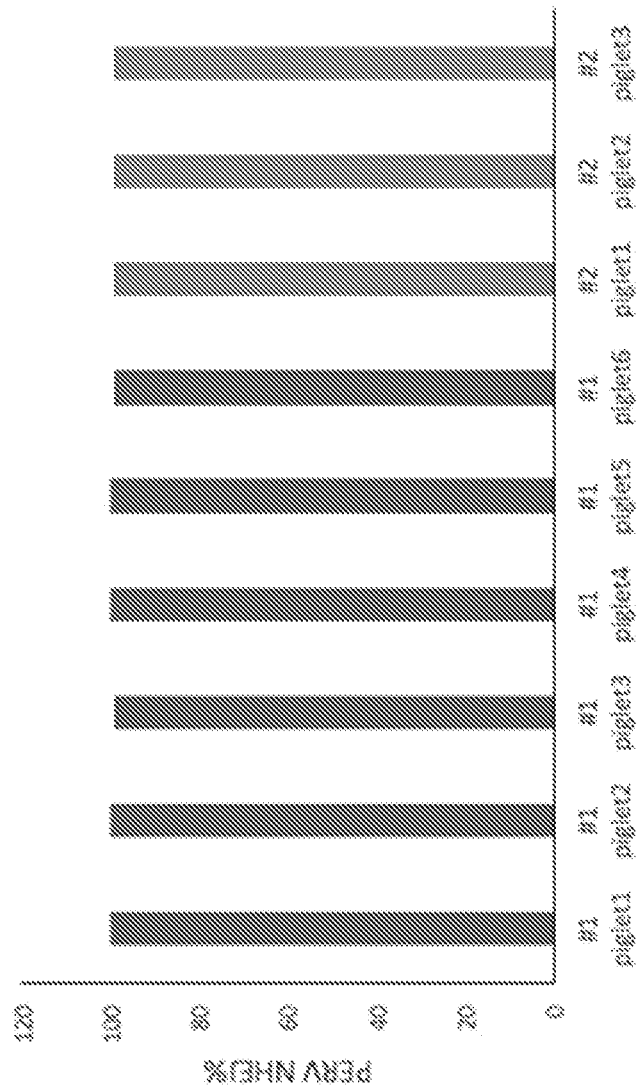
FIG. 10 shows PERV targeting efficiency of nine piglets born PERV-free FFF3. "#1" piglets (six bars to left) and "#2" piglets (three bars to right) indicate two different PERV-free FFF3 clones.
Figure 11:
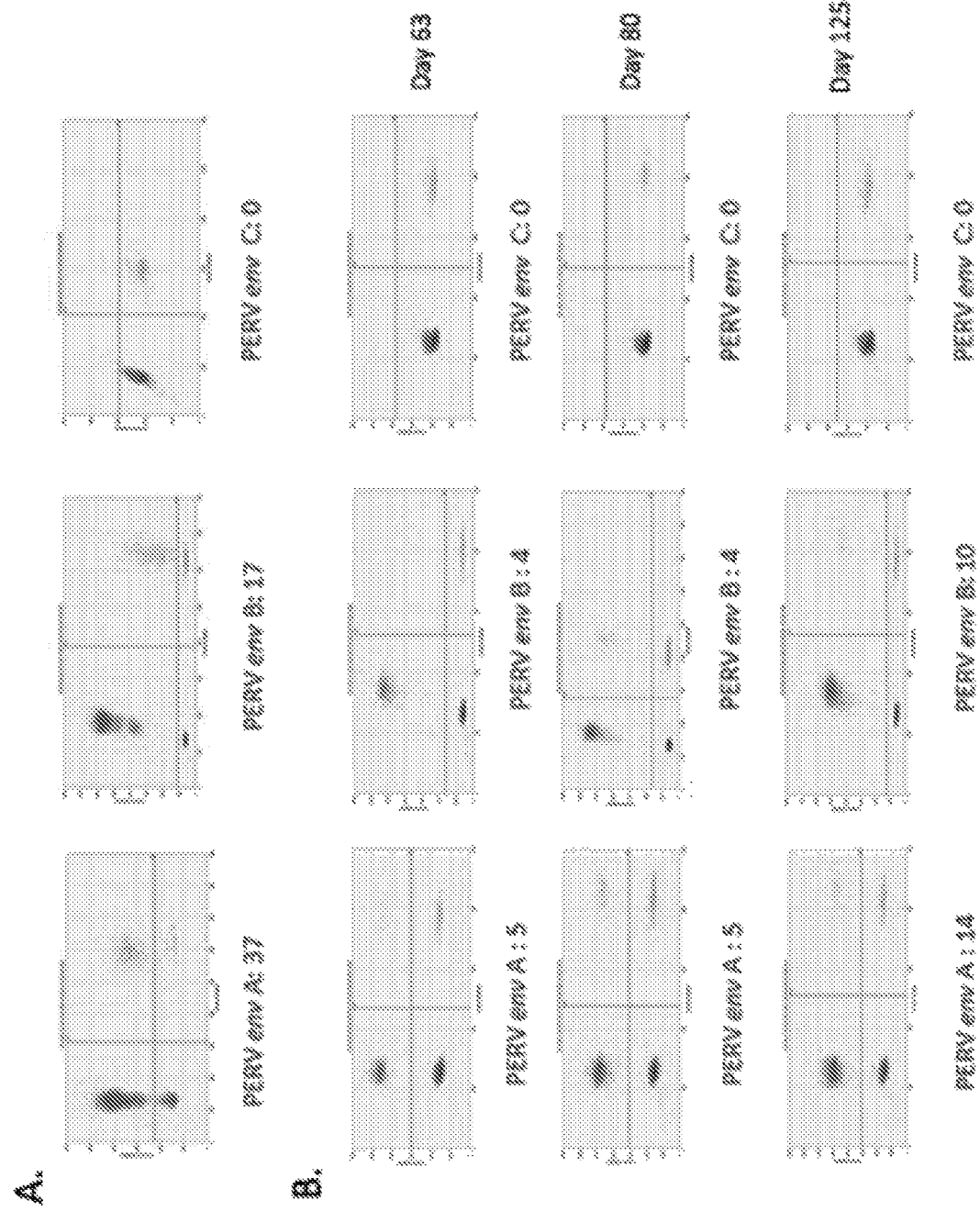
FIG. 11 shows PERVs copy number in pig PK15 and in human HEK293T(iHEK293T-GFP) co-cultured with PK15. A) Copy number of PERV env A, B, C in PK15 cell line. PERV-A and PERV-B, but not PERV-C, were detected in PK15 cells. PERV-A copy number is around two times of PERV-B. In each 2D amplification plot, black dots (bottom left quadrant) represents droplets with no amplification, green (bottom right quadrant) represents droplets containing GAPDH (reference gene), blue (top left quadrant) represents droplets containing PERV env from subtypes A, B, or C, and orange (top right quadrant) represents droplets containing GAPDH and PERV env. The copy number of PERV subtypes A, B, and C, as measured relative to GAPDH, is shown under each plot. B) PK15 transmits PERVs to HEK293T-GFP human cells, and PERV copy number in HEK293T-GFP increases over time. HEK293T-GFP cells were co-cultured with equivalent numbers of PK15 cells. The human cell population was isolated by sequential rounds of sorting based on GFP expression. Purified human cells was collected at three time points and genomic DNA was harvested and amplified via ddPCR to detect and quantify PERV elements in the human cells. PERVs transmission from pig PK15 to human HEK293T cells was detected by ddPCR of PERV env gene. PERV-A and PERV-B, but not PERV-C, were detected in the HEK293T cells which have history of contact with PK15, and the PERV copy number increased in the HEK293T cells over time.
Figure 12:
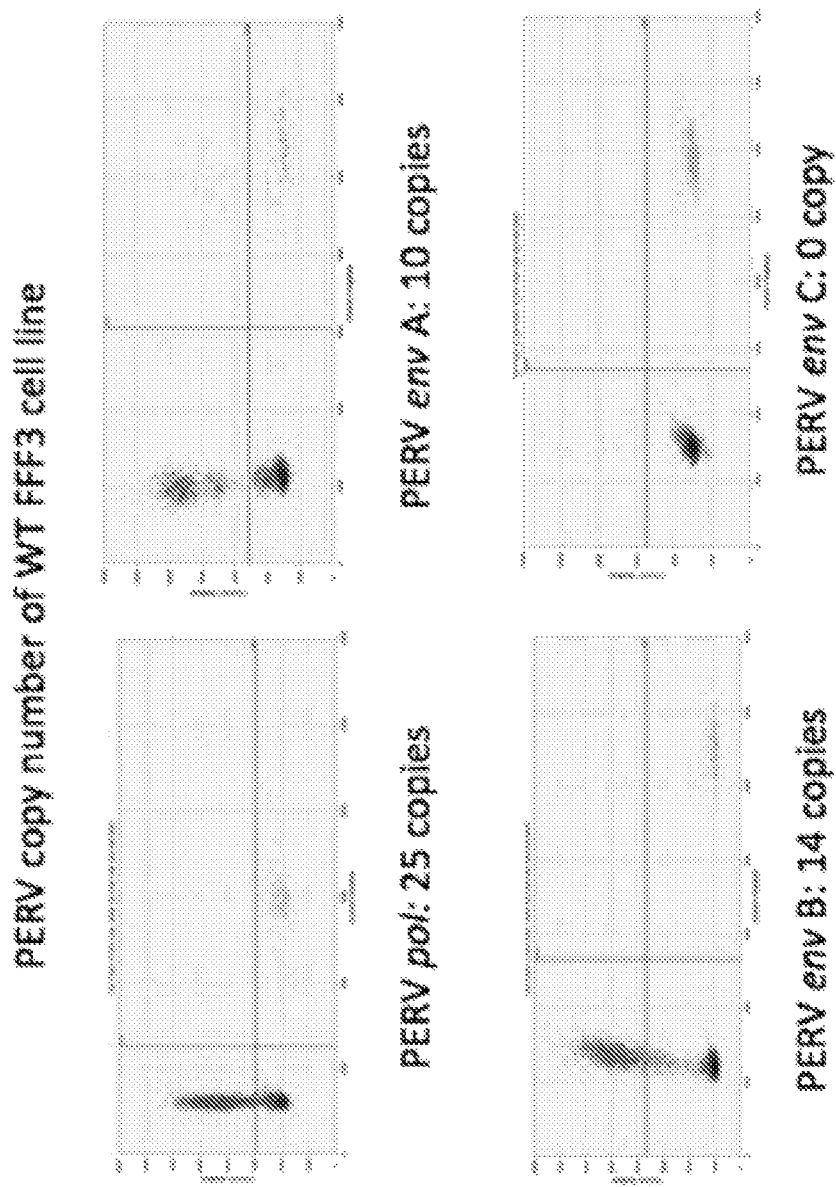
FIG. 12 depicts the validation of PERV subtype copy numbers in FFF3. PERV copy number of WT porcine primary fetal fibroblast cell line (FFF3) was detected by ddPCR of both pol and env genes. The PERV copy number (25) determined by pol gene is similar to that (24) detected by env gene.
Figure 13:
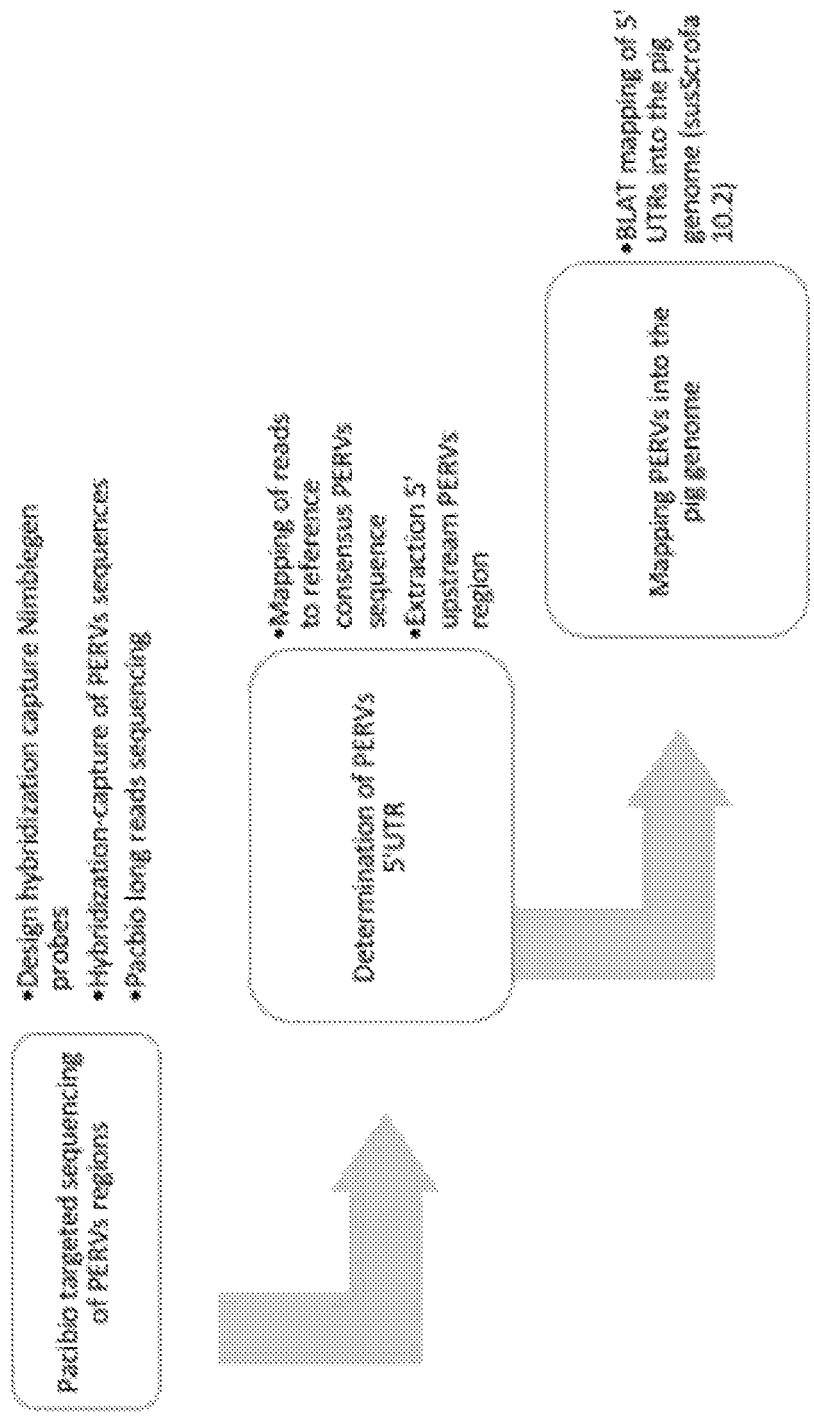
FIG. 13 depicts a schematic describing the process of detecting PERVs location in the pig genome. To map the locations of the PERVs, PacBio long-reads genome sequencing (N50=2,439 bp, described below) was performed after PERVs-specific hybridization capture, and mapped 21 copies of PERVs in non-repetitive regions of the genome.
Figure 14:
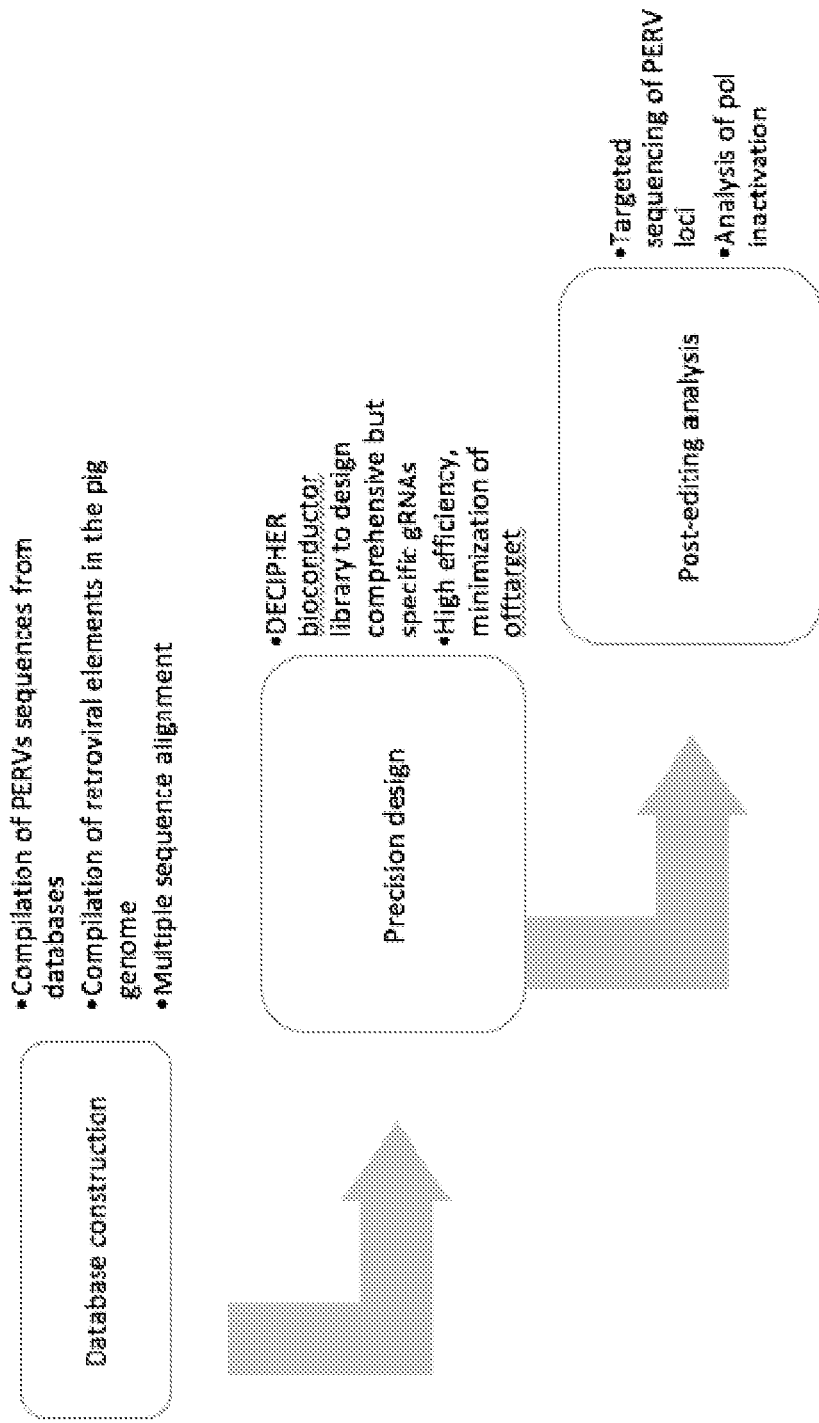
FIG. 14 depicts a schematic describing the design process of the pol targeting gRNAs.
Figures 15A, 15B:
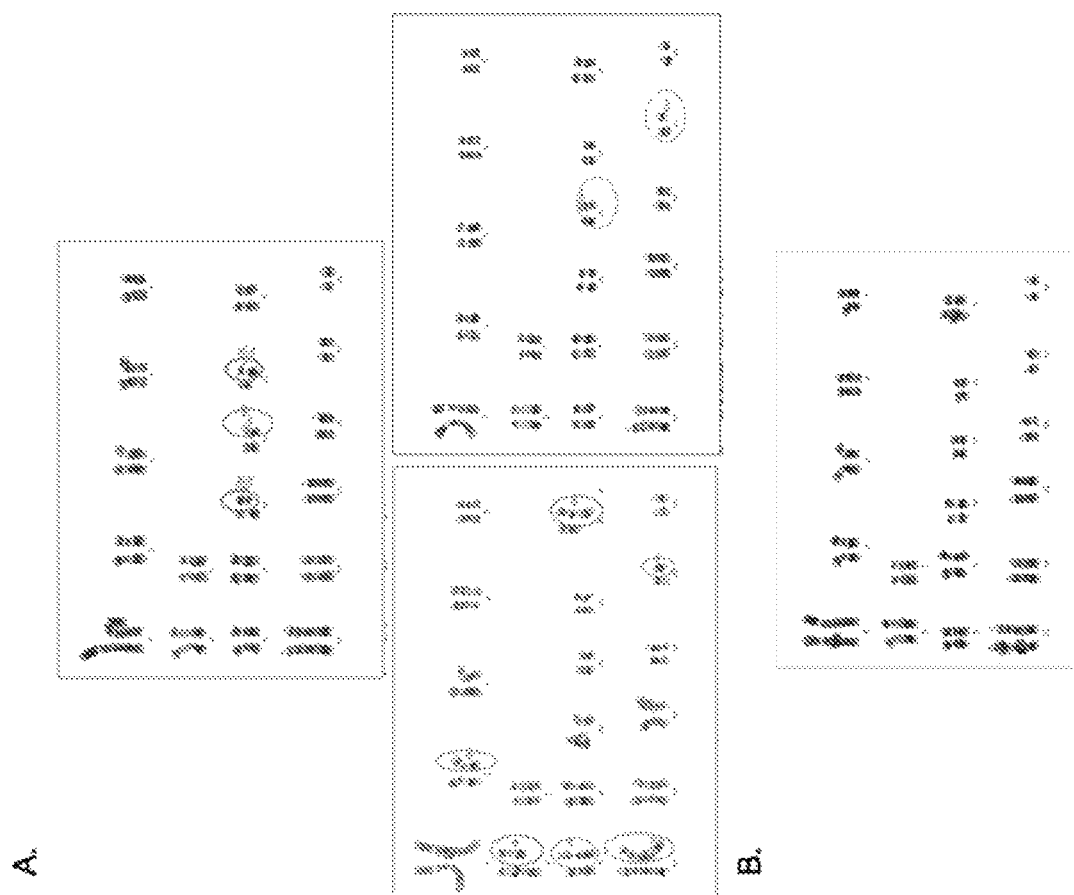
FIG. 15A shows a representative karyotype of the PERV-free clones used for pig cloning. Different clones were analyzed using karyotyping, 5 showed abnormal karyotype and 3 normal. Example of 3 abnormal karyotype. Of note, all chromosomes translocated (indicated by color pairs) or with insertion or deletions contain PERVs except in one case (chromosome 10 of the pair translocated t(10,12), upper panel).
FIG. 15B shows a representative normal karyotype. This PERVs-free clone shows a completely normal karyotype.
Figures 16A, 16B:
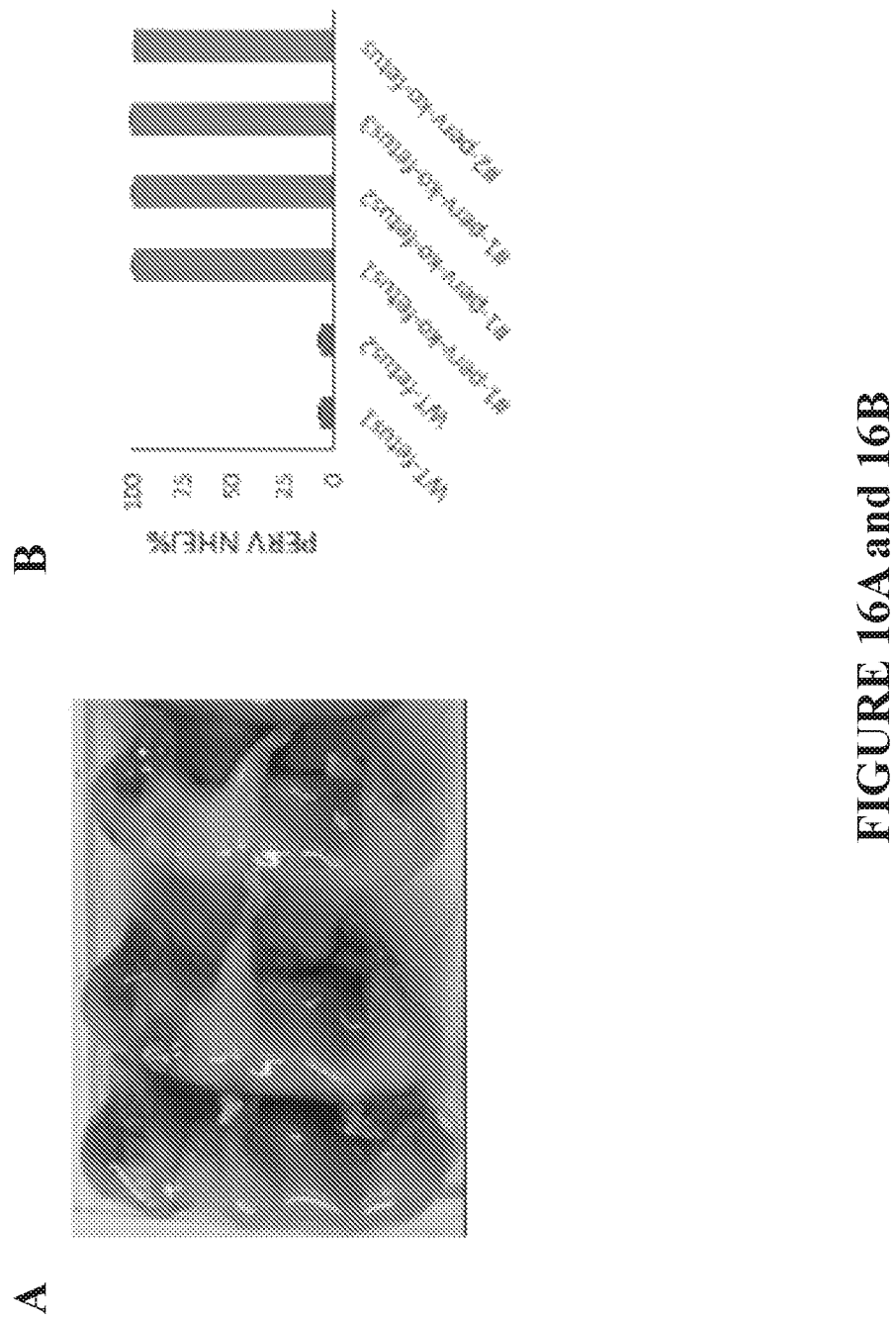
FIG. 16A shows a representative image of PERV-KO fetuses. 6 live fetuses (2 WT and 4 PERV-free fetuses) in total were achieved from 3 surrogate sows. This picture showed the three live PERV-free fetuses achieved from a surrogate sow at day 50 of pregnancy.
FIG. 16B demonstrates PERVs inactivation efficiency in genomic DNA of fetuses. Fetus genomic DNA was used to measure PERV inactivation efficiency. Similar to the originated PERV-free cell line, the PERV-KO fetuses too showed ~100% PERV inactivation efficiency, which suggests that no reinfection from surrogate sow occurred during pregnancy.
Figures 17A, 17B, 17C:
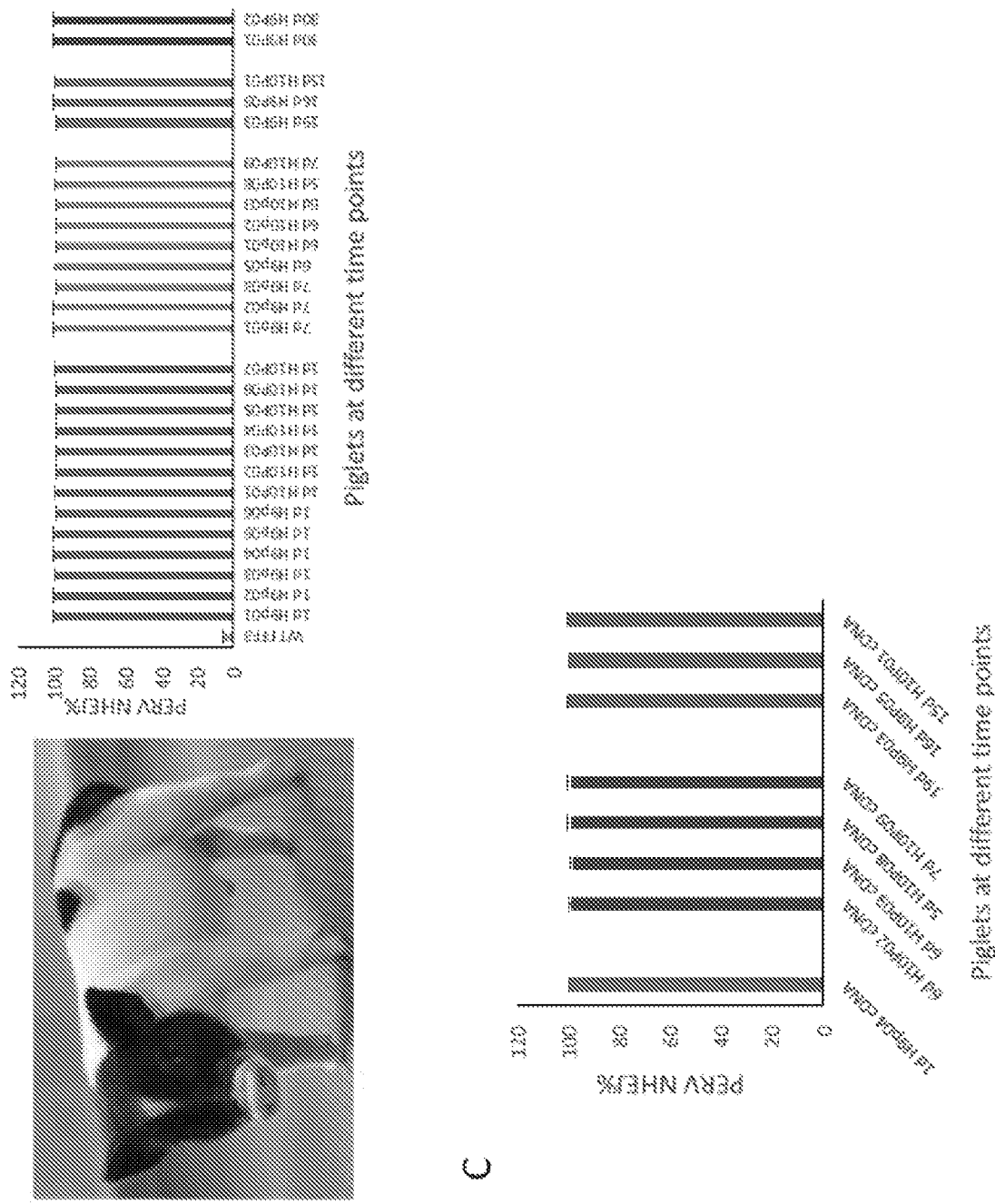
FIG. 17A shows a presentative image of PERV-free pig. This picture showed the first born pig (Laika) at day 2 after birth.
FIG. 17B demonstrates PERV inactivation in genomic DNA of Pigs. PERV-KO pigs were genotyped at different ages by deep sequencing of the PERV pol loci. All examined pigs showed ~100% PERV inactivation efficiency, which demonstrates that there is no detectable PERV reinfection from surrogate sows to cloned pigs.
FIG. 17C demonstrates PERV inactivation at mRNA level. Total mRNA generated cDNA was used to detect the PERV inactivation efficiency of the PERV-KO pig transcripts. All pigs exhibited ~100% PERV eradication efficiency at mRNA level.
Figure 18:
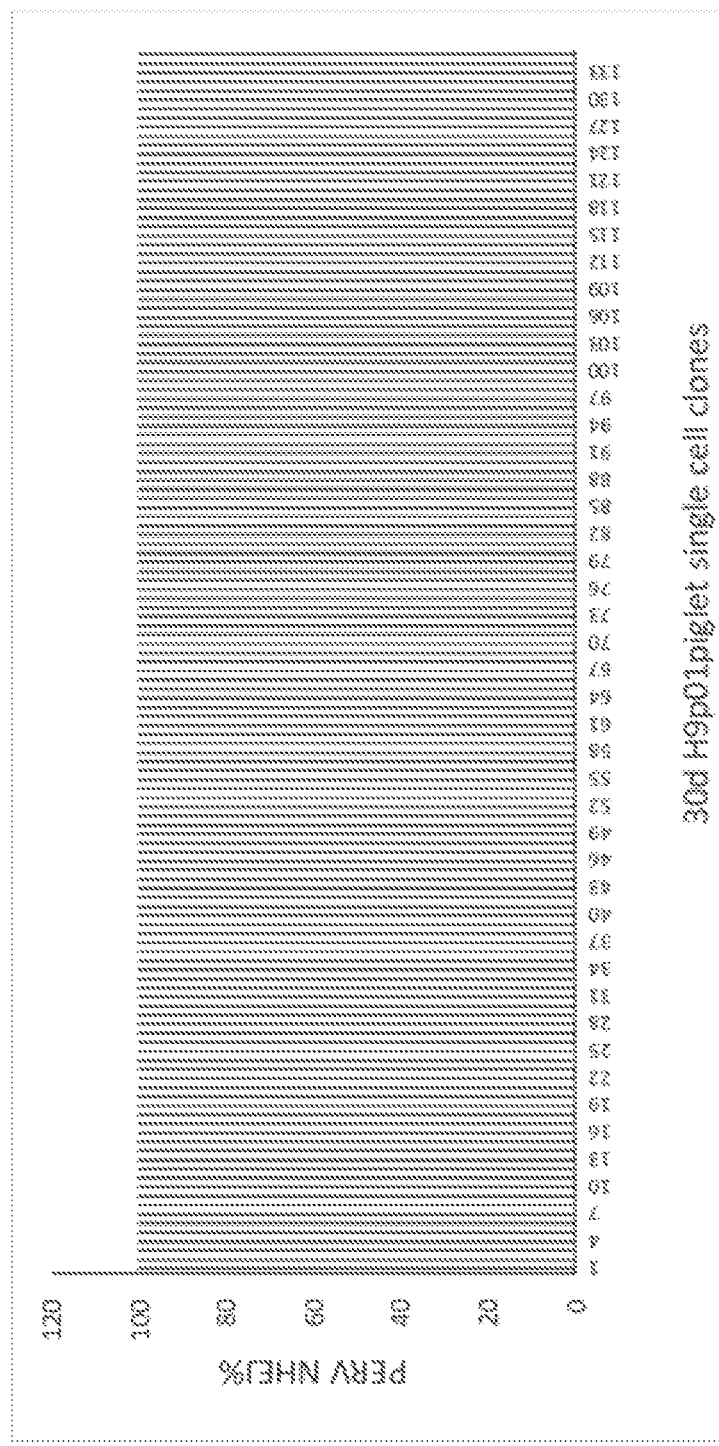
FIG. 18 demonstrates PERV inactivation efficiency of single cells derived from a 30d PERV-free pig. Cells derived from 30d H9p01 PERV-free pig were sorted into single cells and PERV pol gene fragment were genotyped via deep sequencing using genomic DNA of the single cells as template. All single cells showed 100% PERV inactivation.
Figure 19:
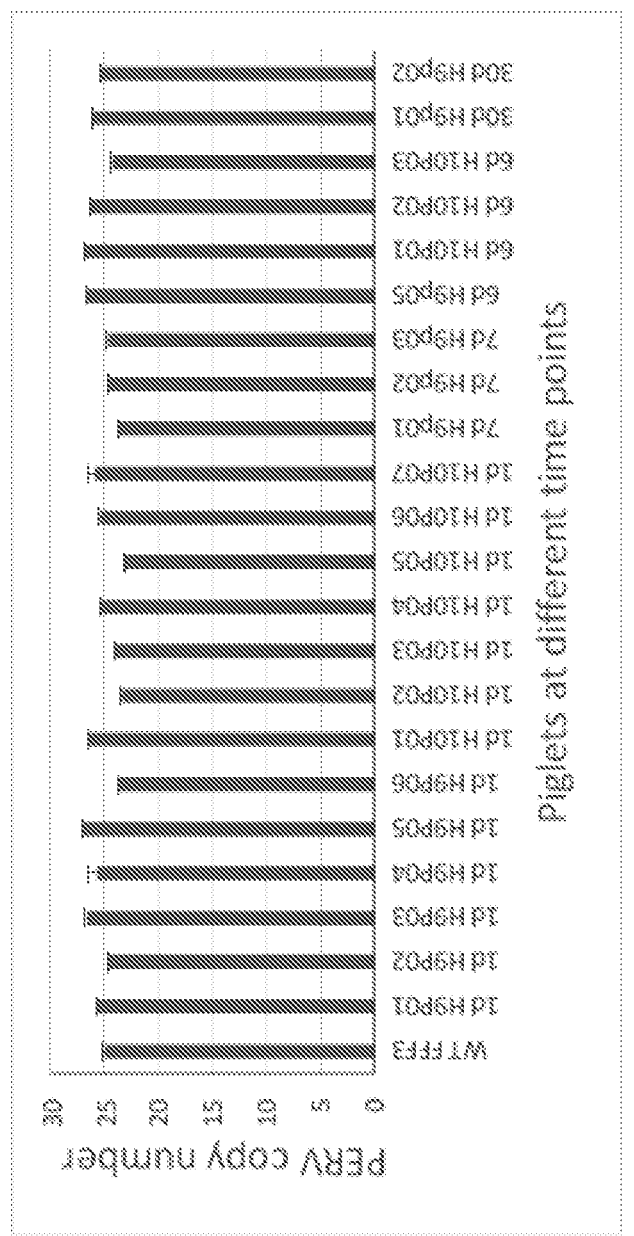
FIG. 19 shows PERV copy number of PERV-free pigs and WT FFF3 fibroblast cells. Genomic DNAs of PERV-free pigs and WT FFF3 fibroblast cells were used to measure PERV copy number by ddPCR. All PERV-free pigs showed similar PERV copy number as the WT FFF3 fibroblast cells.
Figure 20:
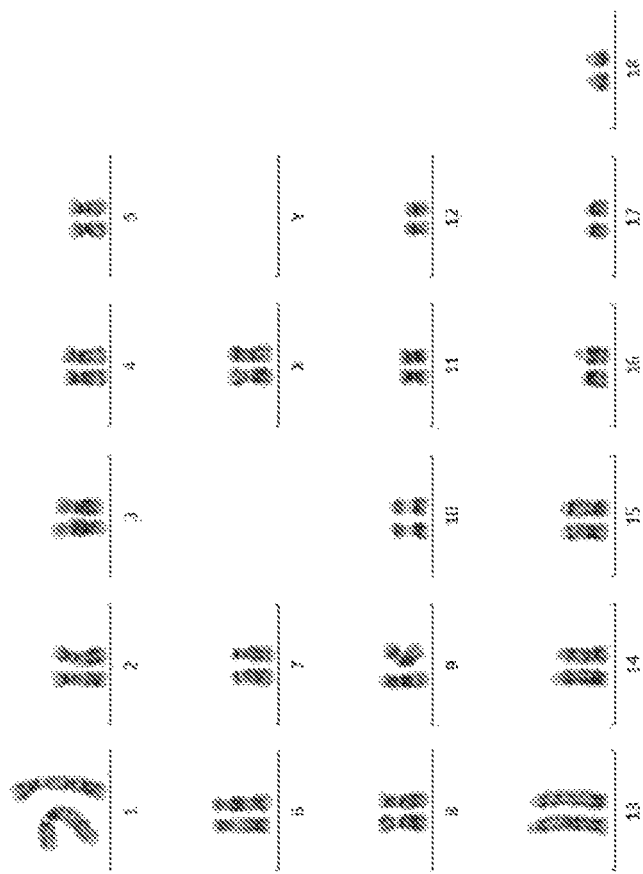
FIG. 20 shows a karyotype representative of that all PERV-free pigs. All PERV-free pigs exhibited normal karyotype.
Figure 21:
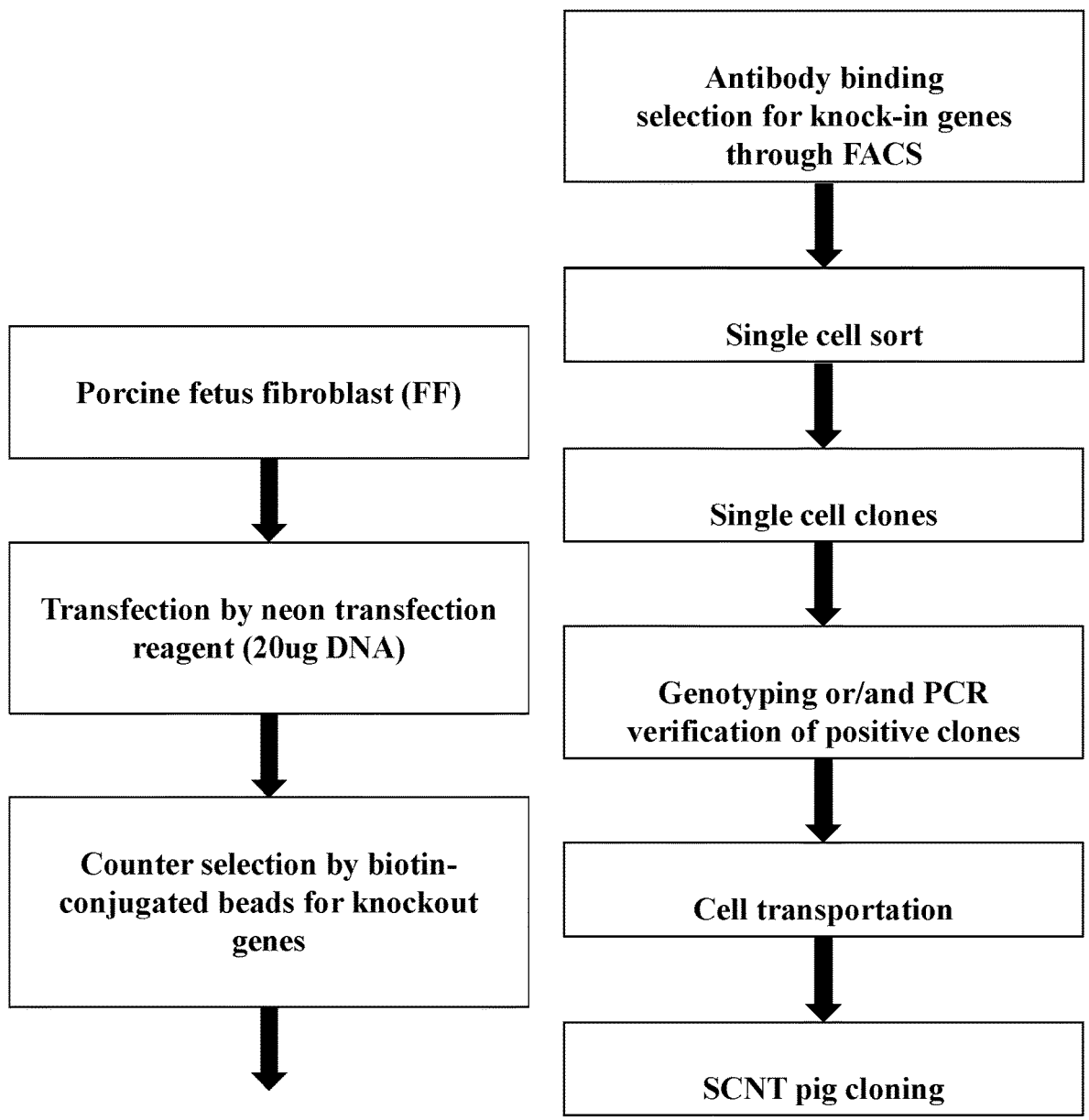
FIG. 21 shows a schematic of a cell line construction strategy according to an embodiment as described herein.
Figure 22:
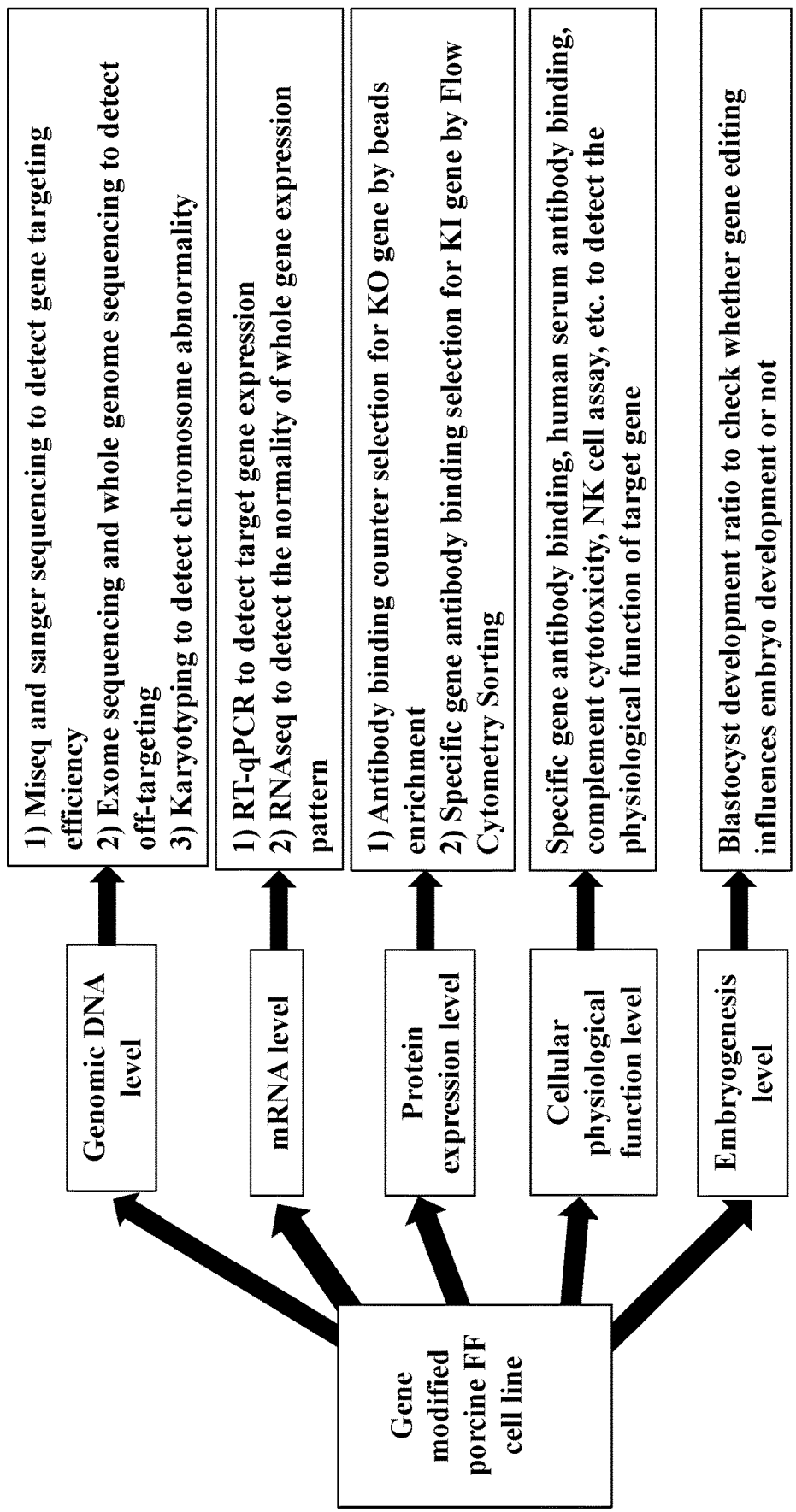
FIG. 22 shows a schematic of cell quality control strategies according to an embodiment as described herein.
Figure 23:
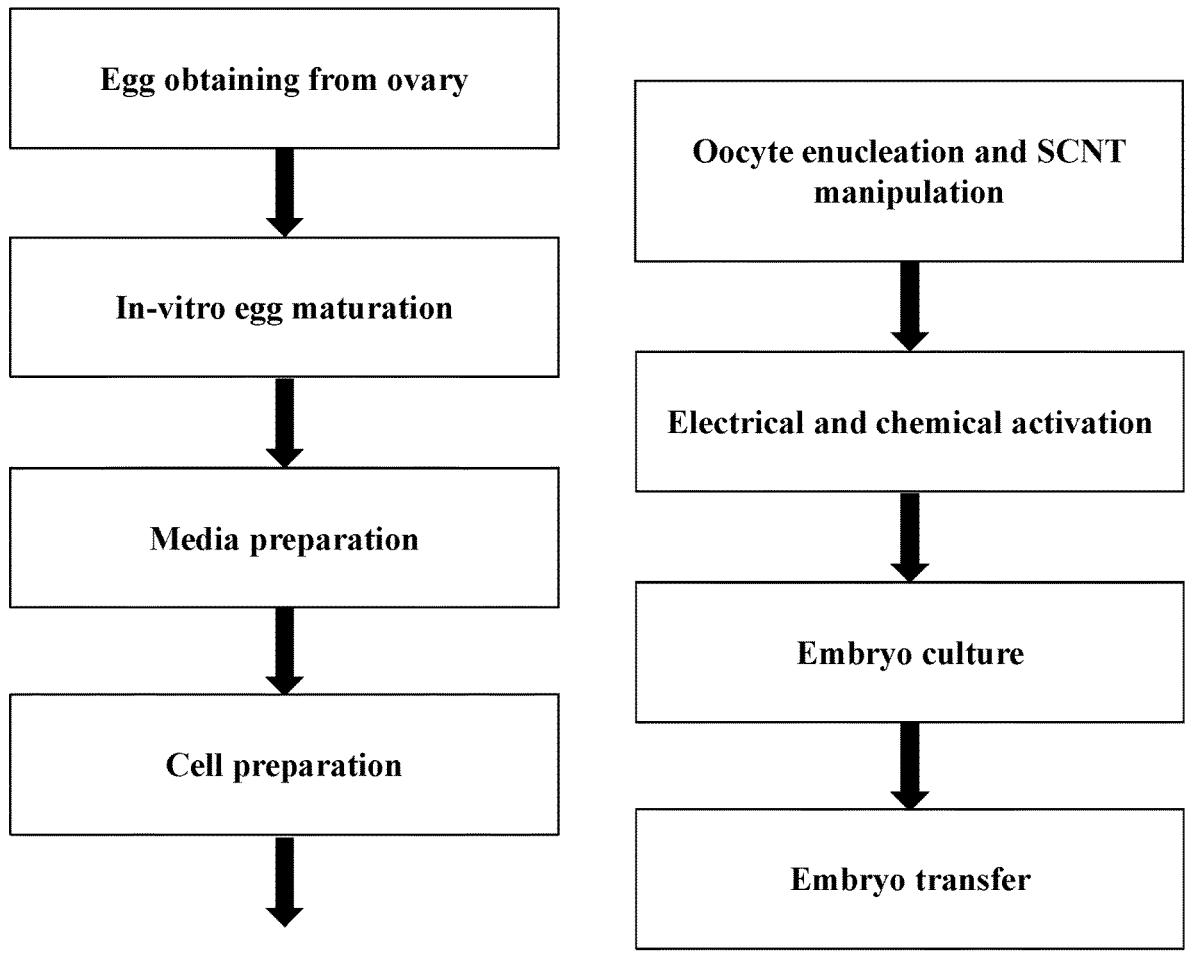
FIG. 23 shows a schematic of a SCNT cloning procedure according to an embodiment as described herein.

PERV-free embryos generated by SCNT from FFF3 with 100% eradication of PERV activity were implanted into surrogate mothers (250 embryos transfer/sow). Fetal genomic DNA was used to measure PERV inactivation efficiency. Similar to the originated PERV-free cell line, the PERV-KO fetuses too showed ~100% PERV inactivation efficiency, which suggests that no reinfection from surrogate sow occurred during pregnancy. (FIGS. 16A and 16B). Surprisingly, even with multiple genetic edits, three months, three weeks and three days later piglets were born completely PERV-free (FIGS. 9 and 10). 16 PERV-free piglets have been produced, 3 of them were born through C-section, 13 of them were born through natural delivery, and 2 out of the 13 died from the dystocia of natural delivery. DNA was isolated from all piglets and mRNA from different tissues of dead piglets and checked the PERV reinfection for both C-section and natural delivered piglets by deep sequencing, and the results showed that all the piglets showed 100% PERV eradication both in genomic DNA and mRNA level. In addition, piglets maintained in facilities having WT have shown no reinfection (FIG. 17). All PERV-free pigs showed similar PERV copy number with WT FFF3 cells (FIG. 19) and a normal karyotype (FIG. 20).

Taken together, this data unequivocally establishes that porcine cells transmit PERVs to primary human cells in vitro. A striking observation from the study was that PERV-infected human cells will pass the PERVs robustly to fresh human cells which have no history of contact with pig cells. Therefore, it is contemplated that it may be necessary to eliminate the risk of PERV transmission before human trials of xenotransplantation. These studies demonstrate the complete eradication of PERV activity in cloneable primary porcine fibroblasts. Furthermore, production of PERV-inactivated porcine embryos, fetuses and piglets using the modified fibroblast cells and the absence of reinfection by the surrogate sows has also been demonstrated. The PERV-free pig is the first mammal lacking active endogenous retroviruses and could lend insight into the biological function of these elements as relevant to the host. Most importantly, the PERV-free pig could serve as a safe source of organs and tissues for pig-to-human xenotransplantation. Since the severe lack of organs for transplantation is a serious challenge for medical treatment of organ failure, this would be a very important and long-awaited biomedical advance.

Methods

CRISPR-cas9 gRNAs Design

The R library DECIPHER was used to design specific gRNAs having the amino acid sequence of SEQ ID NOs: 1-3.

Cell Culture

Porcine PK15 and human HEK293T cells were maintained in Dulbecco's modified Eagle's medium (DMEM, Invitrogen) high glucose with sodium pyruvate supplemented with 10% fetal bovine serum (Invitrogen), and 1% penicillin/streptomycin (Pen/Strep, Invitrogen). All cells were maintained in a humidified incubator at 37° C. and 5% $Co_2$.

Porcine fetus fibroblast cells FFF3 were maintained in Dulbecco's modified Eagle's medium (DMEM, Invitrogen) high glucose with sodium pyruvate supplemented with 15% fetal bovine serum (Invitrogen), 1% penicillin/streptomycin (Pen/Strep, Invitrogen) and 1% HEPES (Thermo Fisher Scientific). All cells were maintained in a humidified tri-gas incubator at 38° C. and 5% $CO_2$, 90% $N_2$, and 5% $O_2$.

PiggyBac-Cas9/2gRNAs Construction and Cell Line Establishment

Similar to the procedure previously described by Yang et al, 2015, Science, 80:350, a DNA fragment encoding U6-gRNA1-U6-gRNA2 (Genewiz) was synthesized and incorporated into a previously constructed PiggyBac-cas9 plasmid. To establish the FFF3 cell lines with PiggyBac-Cas9/2gRNAs integration, $5 \times 10^5$ FFF3 cells were transfected with 16 µg PiggyBac-Cas9/2gRNAs plasmid and 4 µg Super PiggyBac Transposase plasmid (System Biosciences) using the Neon transfection system according to the instructions in the commercial kits (Thermo Fisher Scientific). To select the cells carrying the integrated construct, 2 µg/mL puromycin was applied to the transfected cells. Based on the negative control, in which puromycin was applied to wild type FFF3 cells, it was determined that the puromycin selection was completed in 4 days. The FFF3-PiggyBac cell line was maintained with 2 µg/mL puromycin hereafter and a 2 µg/ml doxycycline was applied to induce Cas9 expression of the doxycycline-inducible FFF3-PiggyBac cell line.

To avoid the Cas9-consistent expression in the FFF3 cell line, PiggyBac-Cas9/2gRNAs excision from the FFF3 genome was conducted by transfecting $5 \times 10^5$ cells with 3 µg PiggyBac Excision-Only Transposase vector using Lipofectamine 2000 reagent. The PiggyBac-Cas9/2gRNAs-excised FFF3 cells were then single-cell sorted into 96-well plates for clone growth and genotyping.

Genotyping of Single-Cell Clones

First, puromycin selection followed by PiggyBac excision was conducted on the FFF3, PiggyBac-Cas9/2gRNA cell line. Then the cells were single-cell sorted into both 96-well PCR plates for direct genotyping and 96-well cell culture plates for colony growth.

To genotype single FF cells without clonal expansion, the PERV loci from sorted single cells were directly amplified according to a previously reported single-cell genotyping protocol. Briefly, the single cells were sorted into 96-well PCR plates with each well carrying a 5 µl lysis mixture, which contained 0.51 µl 10×KAPA express extract buffer (KAPA Biosystems), 0.1 µl of 1 U/µl KAPA Express Extract Enzyme and 4.6 µl water. The lysis reaction was incubated at 75° C. for 15 min and the reaction was subsequently inactivated at 95° C. for 5 min. All reactions were then added to 20 µl PCR reactions containing 1×KAPA 2G fast (KAPA Biosystems), 0.2 µM PERV Illumina primers (Methods Table 2). Reactions were incubated at 95° C. for 3 min followed by 25 cycles of 95° C., 20 s; 59° C., 20 s and 72° C., 10 s. To add the Illumina sequence adaptors, 3 µl of reaction products were then added to 20 µl of PCR mix containing 1×KAPA 2G fast(KAPA Biosystems) and 0.3 µM primers carrying Illumina sequence adaptors. Reactions were incubated at 95° C. for 3 min followed by 10 cycles of 95° C., 20 s; 59° C., 20 s and 72° C., 10 s. PCR products were checked on EX 2% gels (Invitrogen), followed by the recovery of 300-400 bp products from the gel. These products were then mixed at roughly the same amount, purified (QIAquick Gel Extraction Kit), and sequenced with MiSeq Personal Sequencer (Illumina). Deep sequencing data was analyzed, and the PERV editing efficiency using CRISPR-GA was determined (Denner et al., 2016, Viruses, 8:215).

Primers Used in the PERV pol Genotyping

```
Illumina_PERV_pol forward:
                                    (SEQ ID NO: 4)
5'-ACACTCTTTCCCTACACGACGCTCTTCCGATCTCGACTGCCCCAAGG
GTTCAA-3'

Illumina_PERV_pol reverse:
                                    (SEQ ID NO: 5)
5'-GTGACTGGAGTTCAGACGTGTGCTCTTCCGATCTTCTCTCCTGCAAA
TCTGGGCC-3'
```

PERV Infectivity Test of PK15-WT to GFP-HEK293T and GFP-HEK293T to WT HEK293T

I) PERV Infectivity Test of PK15 WT to GFP-HEK29T

The procedure is similar to that previously described by Yang et al., 2015, Science, 80:350. Briefly, $1 \times 10^5$ cells of Lenti-GFP-HEK293T cells and $1 \times 10_5$ PK15 WT cells were co-cultured together in a 10 cm dish and grown for one week. Sequential cell sorting was conducted through flow cytometry to obtain high purity GFP positive GFP-HEK293T cells. The GFP-HEK293T cells were sorted as bulk and cultured for 125 days. Genomic DNAs were isolated from the cells at different time points (d76, d80, and d125) to detect whether the PERV copy number increased with time going via ddPCR. Single cell sorting from the bulk cells was conducted at different time points. After the single cell grew up into clones, the PERV infection of some clones was examined by PCR first and then quantified the PERV copy number of the PERV-infected clones via ddPCR.

2) PERV Infectivity Test of GFP-HEK293T to WT HEK293T

To test whether PERV can be transmitted from human to human cells, $1 \times 10^5$ cells of PERV-infected HEK293T-GFP (i-HEK293T-GFP) clone were co-cultured with $1 \times 10^5$ cells of WT HEK293T for 2 weeks, then the GFP negative single cells were sorted via flow cytometry. After the single cell grew up into clones, the PERV infection by PCR was examined to detect the infection ratios of different i-HEK293T-GFP clones. Particularly, the PERV copy number of GFP negative clones which were co-cultured with i-HEK293T-GFP clone 10 were quantified via qPCR using the ddPCR-detected copy number of i-HEK293T-GFP clone 10 as the standard marker.

Reverse Transcriptase (RT) Assay

The RT assay is same as the protocol previously described by Yang et al., 2015, Science, 80:350. Briefly, to test the RT activity of the FFF3 wild type cells and 100% modified FFF3 clones, $5 \times 10^5$ cells were plated in 10 cm Petri dishes, and the supernatan was collected after cells reached 80% confluency. The media were first centrifuged at 400 g for 4 min to get rid of cells and debris, then filtered with a 0.45 µM Millex-HV Syringe Filter (EMD Millipore Corporation). The filtered supernatant was concentrated at 4000 g for 10 min using Amicon Ultra-15 Centrifugal Filter Unit (EMD Millipore Corporation). The concentrated supernatant was then ultra-centrifuged at 50,000 rpm for 60 min. The supernatant was carefully removed, and the virus pellet was fully resuspended and lysed with 20 μl of 10% NP40 at 37 for 60 min. The RT reaction was conducted using the Omniscript RT Kit (Qiagen). The total volume of the reaction was 20 μl, which contained 1×RT buffer, 0.5 mM dNTPs, 0.5 μM Influenza reverse primer (5' CTGCATGACCAGGGTTTATG 3') (SEQ ID NO: 6), 100 units of RnaseOUT (Life Technology, Invitrogen), 100 units of SuperRnase Inhibitor (Life Technologies), 5 μl of sample lysis and 40 ng of IDT-synthesized Influenza RNA template which was Rnase resistant in both 5' and 3' end. The RNA template sequence was 5' rA*rA*rC*rA*rU*rGrGrArArCrCrUrUrUrGrGrCrCrCrUr GrUrUrCrArUrrUrUrArGrArArArUr CrArArGrUrCrArArGrArUrArCrGrCrArGrArArGrArGrUrArGrArCrArUrArArArCrCrCrUrGrG rUrCrArUrGrCrArGrArCrCrU*rC*rA*rG*rU*rG 3' (*phosphodiester bond) (SEQ II) NO: 7). After the RT reaction was completed, the RT product was examined by PCR using Influenza forward (5' ACCTITGGCCCTGTTCAITT 3') (SEQ ID NO: 8) and Influenza reverse primers (sequence shown as above). The expected size of the amplicon was 72 bp.

quantify the copy number of PERVs according to the manufacturer's instructions (BioRad). Briefly, genomic DNA was extracted (DNeasy Blood & Tissue Kit, Qiagen) from cultured cells, and 50 ng genomic DNA was digested with Msel (10 U) at 37° C. for 3 hrs, followed by inactivation at 65° C. for 10 min. Then the ddPCR reaction was prepared. The reaction mixture contains 1× ddPCR Master mix, 1 μl of 18 μM target primers & 5 μM target probe (VIC), 1 μl of 18 μM reference primers & 5 μM reference probe (FAM), 5 ng digested DNA, and water to total volume of 20 μL. The sequences of the primers and the probe information can be found in Extended Data Table 1.

After droplet generation with QX100 Droplet Generator, the droplets were carefully transferred into a 96-well PCR plate and proceeded to the thermal cycling, using a Biorad PCR machine as follows: 95° C. 10 min for enzyme activation, then 40 cycles of 94° C. 30 sec for denaturation and 60° C. 1 min for annealing/extension (ramp rate 2° C./sec), then 98° C. 10 min for enzyme deactivation.

After the thermal cycling, the 96-well plate was placed in Biorad Droplet Reader and QunataSoft Software was used to set up the experimental design and read the experiment. Once the program was finished, the results were analyzed through gating according to the manufacturer's instructions (BioRad).

Methods Table 1-Primers used in ddPCR assay

| Name | Sequence | SEQ ID NO |
|---|---|---|
| pervA env ddpcr fw | 5'-TTCGCCTCAGAATAGAAACTCAG-3' | SEQ ID NO: 9 |
| pervA env ddpcr rv | 5'-GTTAGGAGATGGCCTCTGTTCTT-3' | SEQ ID NO: 10 |
| pervA env ddpcr probe | 5'/56-FAM/CCAAACCCTTATTTGGTCCTATAGCAAC/3BHQ_1/-3' | SEQ ID NO: 11 |
| pervB env ddpcr fw | 5'-GGGCAAGTACAAAGTGATGAAAC-3' | SEQ ID NO: 12 |
| pervB env ddpcr rv | 5'-ATTCCCCAGCTCATACCATTTAT-3' | SEQ ID NO: 13 |
| pervB env ddpcr probe | 5'-/56-FAM/ATAAGAGCTGCTCCCCATCAGACTTAGAT/3BHQ_1/-3' | SEQ ID NO: 14 |
| pervC env ddpcr fw | 5'-TAAATGGTATGTCTTGGGGAATG-3' | SEQ ID NO: 15 |
| pervC env ddpcr rv | 5'-AGACCGTATTTGGTCCTATAGCC-3' | SEQ ID NO: 16 |
| pervC env ddpcr probe | 5'-/56-FAM/CCTGGTTGTTTACCCGAGCCTCCA/3BHQ_1/-3' | SEQ ID NO: 17 |
| PrimerPol1-FW | 5'-CGACTGCCCCAAGGGTTCAA-3' | SEQ ID NO: 18 |
| PrimerPol2-FW | 5'-CCGACTGCCCCAAGAGTTCAA-3' | SEQ ID NO: 19 |
| PrimerPol-RV | 5'-TCTCTCCTGCAAATCTGGGCC-3' | SEQ ID NO: 231 |
| ProbePol | 5'-/56FAM/CACGTACTGGAGGAGGGTCACCTG-3' | SEQ ID NO: 20 |
| Primerpig_GAPDH_F | 5'-ccgcgatctaatgttctctttc-3' | SEQ ID NO: 21 |
| Primerpig_GAPDH_R | 5'-ttcactccgaccttcaccat-3' | SEQ ID NO: 22 |
| Probepig_GAPDH | 5'-/5HEX/cagccgcgtccctgagacac-3' | SEQ ID NO: 23 |

PERV Copy Number Quantification

As previously described by Yang et al., 2015, Science, 80:350, Droplet Digital PCR™ (ddPCR™) was used to Targeting Efficiency Calculation As previously described in Yang et al. (6), a custom pipeline was built to estimate the efficiency of PERV inactivation. Briefly, the pol gene was amplified and sequenced via Illumina Next Generation Sequencing using PE250 or PE300. First, the two overlapping reads using PEAR (15) were combined and mapped to the reference region using BLAT. After mapping, the reads were grouped into sets containing specific combinations of haplotypes, and indel types. Read sets with representation lower than 0.5% of the total number of mapped reads were discarded. Finally, the mapping output was parsed to call the different insertions and deletions, as described in Güell et al (16).

PERV-Human Junction Capture

The PERV insertion sites in the highly infected i-HEK293-GFP clones were determined by the standard inverse PCR protocol. The genomic DNA of these clones were fragmented by Sau3AI digestion and self-ligated under low DNA concentration using T4 DNA ligase (NEB). Then the fragments containing the PERV-human junctions were amplified by PCR using primers on the PERV LTRs shown below. The PCR products were subclones using the PCR Blunt TOPO kit (Thermo Fisher) and Sanger sequenced. Sequences immediately next to the PERV LTRs were aligned to the human genome using USCS Genome Browser. Part of the hits in human genes were validated using junction PCR and Sanger sequencing.

```
SEQ ID NO: 24-PERV_LTR_F:
ATGCCCCGAATTCCAGA

SEQ ID NO: 25-PERV_LTR_R:
GGTTAGGTTGCATTTTCATCCTT
```

Handmade Cloning to Produce SCNT Porcine Embryos

All chemicals were purchased from Sigma-Aldrich except where otherwise indicated. The handmade cloning (HMC) was based on the procedure described by Du et al., Theriogenology, 68:1104-10. Briefly, porcine ovaries were obtained from slaughter house and cumulus cell-oocyte complexes (COC) were collected from big follicles. In-vitro maturation of porcine oocyte was then performed in four-well dishes (Nunc, Thermo Fisher Scientific) containing 400 uL of bicarbonate-buffered M199 medium (Gibco, Thermo Fisher Scientific) supplemented with 10% pig follicular fluid, 10% fetal bovine serum (FBS) (Gibco, Thermo Fisher Scientific), 10 IU/mL pregnant mare serum gonadotropin (PMSG) and 5 IU/mL human chorionic gonadotropin (hCG) under mineral oil and incubated for 42-43 hours at 38.5° C., 5% $CO_2$, 5% $O_2$ and 90% $N_2$, in humidified air. After maturation, the cumulus cells of the COC were removed by repeated pipetting in HEPES-buffered M199 containing 1 mg/ml hyaluronidase, followed by oocyte wash in T2 (EPES-buffered M199 with 2% FBS) droplets. From this point, all manipulations were performed on a heated stage adjusted to 39° C. The solution droplets (20 ul/droplet) were made on a 60-mm Petri dish lid (Corning, Thermo Fisher Scientific) and covered with mineral oil. The transfer of oocytes was conducted by using a finely drawn and fire-polished glass pipette. The oocytes were placed into a pronase droplet (3.3 mg/mL) and digested for ~1 min until the oocytes changed shape, then followed by series wash in T2 and T20 (HEPES-buffered M199 with 20% FBS) droplets and the zona pellucida of oocytes were removed during the wash. The zona free oocytes were then lined up in the T20 droplets containing 2.5 ug/iml Cytochalasin B (CB). Oocyte enucleation was directed by the polar body position and performed manually under a stereomicroscope with Ultra Sharp Splitting Blades (Shearer Precision Products LLC, Pullman, WA) to remove ⅓ of the oocyte cytoplasm, and then the enucleated oocytes were placed in T2 droplets for next step of fusion. In order to perform the oocyte-somatic cell fusion, the 100% PERV-KO FFF3 fibroblast cells were detached by using 0.25% Trypsin and neutralized with T10 (HEPES-buffered M199 with 10% FBS) and filtered to get separated single cells. Meanwhile, solution droplets for fusion were prepared on a 35-mm Petri dish lid (Corning, Thermo Fisher Scientific) and the enucleated oocytes called cytoplasts and 1-5 µl somatic cells were placed in different T10 droplets. The cytoplasts were individually transferred to 0.4 mg/mL of phytohaemagglutinin (PHA-P) for 2-3 s and then quickly dropped onto a single cell that was settled to the bottom of the T10 droplet. Following attachment, the cytoplast-cell pair was picked up and balanced in a porcine fusion medium (pFM) droplet which contains 0.3 M mannitol and 5 µm Poly (vinyl alcohol) (PVA), then transferred to a fusion chamber covered with 500 µL pFM solution. The fusion chamber contained parallel platinum wires with a diameter of 0.5 mm and a separation of 0.8 mm.

Using an alternating current (AC) of 2 V (CELLFUSION: BLS CF-150/$B_{SP}$, BLS Ltd., Hungary), the pair was attached to the negative pole wire with somatic cell furthest from the wire and then fused with a single direct current (DC) pulse of 100 V for 9 µs. The pair was then carefully removed and incubated in T0 for 1 hr to allow complete fusion of somatic cell into the cytoplast. And the same procedure was repeated for more fusions of cytoplast and somatic cell.

The above fused pair was then fused with another unfused cytoplast. Similarly, the unfused cytoplast was transferred to the fusion chamber covered with 500 µL of bovine fusion medium (bFM) which contains 0.3 M mannitol, 5 µm PVA, 1 mM $MgSO_4$ and 0.5 mM $CaCl_2$. The same AC of 2V was used to attach the unfused cytoplast to the negative pole wire, then the fused pair was placed at the other side of the cytoplast with the pair furthest from the negative wire. A single pulse of 43V DC for 80 µs was applied to fuse the cytoplast-pair triplet. The triplet i.e. constructed embryo was then placed in T10 droplet for ~10 min to allow the complete fusion of cytoplasts. Chemical activation was conducted after the second fusion. The constructed embryos were incubated for 4 hr in 400 µL PZM3 solution (Guell et al., 2014, Bioinformatics, 30:2968-2970) supplemented with 5 µg/ml CB and 10 µg/ml cycloheximide (CX) and covered with mineral oil, then the embryos were washed in PZM3 and transferred to a well of the well (WOW) system which contains small U bottom holes made with aggregation needle DN-09/B (BLS Ltd., Hungary) on the bottom of a 4-well dish. The constructed embryos in WOW system were then incubated in a humidified trigas incubator with 5% $CO_2$, 5% $O_2$, and 90% $N_2$ at 38.5° C. for 7 days to allow the blastocyst forms and the blastocyst per reconstructed embryo rates were evaluated.

Immunostaining

Day 7 porcine blastocysts were fixed and stained using the Pluripotent Stem Cell 4¬ Marker Immunocytochemistry Kit (Molecular Probes A24881), according to the manufacturer's instructions. However, the antibodies provided by the kit were substituted with primary goat anti-pig anti-SOX2 (sc-17320) and rabbit anti-goat IgG secondary antibodies conjugated with Alexa Fluor 647 (Invitrogen A-21446). NucBlue@ Live ReadyProbes® Reagent (Molecular Probes R37605) and Phalloidin (A22282) were applied five minutes before imaging. The final concentration of antibodies used in embryo staining is 1:100 for anti-SOX2, 1:200 for rabbit anti-goat IgG, 1:40 for Phalloidin and 1:100 for NucBlue.

Confocal Microscopy

Blastocysts were transferred to wells of a micro-Insert 4 Well in I-Dish 35 mm (Ibidi 80406) and imaged using a Leica TCS SP5 Confocal Laser Scanning Microscope with a 10× water objective. Images were cropped, segmented, and contrast-enhanced using a combination of Imaris and Fiji software.

Example 5. Single Cell Clones with Desired Genotype for SCNT

After CRISPR/cas9 gene editing, the cell population was single-cell sorted into 96-well plate and grown for ~14 days in DMEM supplied with 4.5 g/L D-glucose, 110 mg/L sodium pyruvate, GlutaMax as well as 5 ng/ml basic fibroblast growth factor (bFGF) (13256029, Thermo Fisher Scientific) and 10 ng/ml cyclic pifithrin-α hydrobromide (cPFT-α) (P4236, Sigma), a P53 inhibitor. Genomic DNA was then isolated from the single cell clones and conducted genotyping. Next, the desired clones were expanded and cultured in the above described culture condition. This strategy generates clones with the desired genotype, but the cell viability may be suboptimal due to cell doubling too many times. However, the addition of bFGF and cPFT-α in the culture medium will greatly improve the cell viability.

Example 6. Bulk Cell Modification for SCNT

Figure 24:
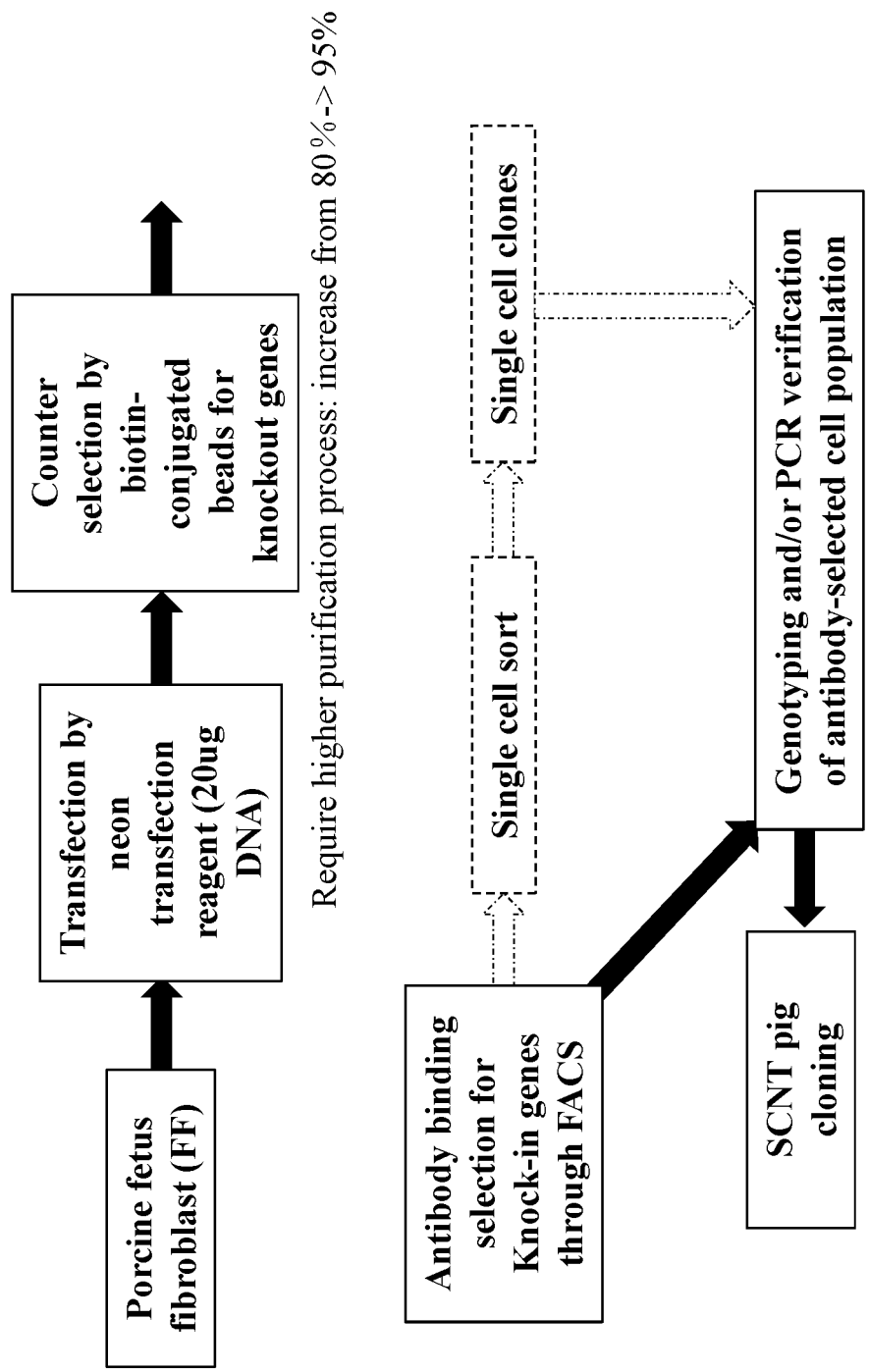
FIG. 24 shows a schematic of a method for improving cell viability conditions according to an embodiment as described herein. Briefly, the single cell cloning process is skipped to shorten in vitro culture time window. The selected cell population is used instead of single cell clones for SCNT to reduce cell growth time and the sow itself selects the embryos with best gene modification for fetus development.

Following gene editing, the modified cells were enriched by antibody binding or beads selection and the enriched cell population was directly used for SCNT without going through single cell sort procedure. FIG. 24. This strategy reduces the cell culture time and circumvents cells from getting too old and generally less viable.

Example 7: In Vivo Modification

Figure 25:
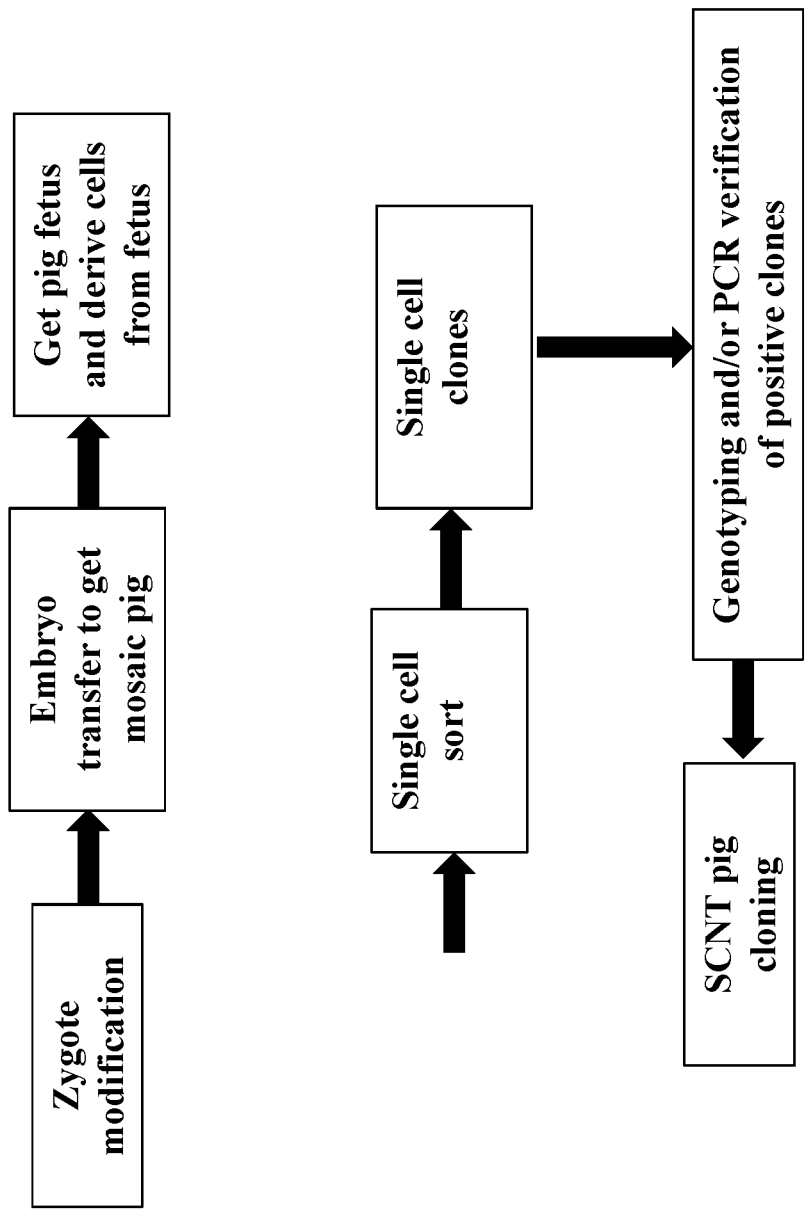
FIG. 25 shows a schematic of a method for improving cell viability conditions according to an embodiment as described herein. Briefly, modifications are conducted on a zygote by microinjection instead of cells to reduce stress on cells.
Figure 26:
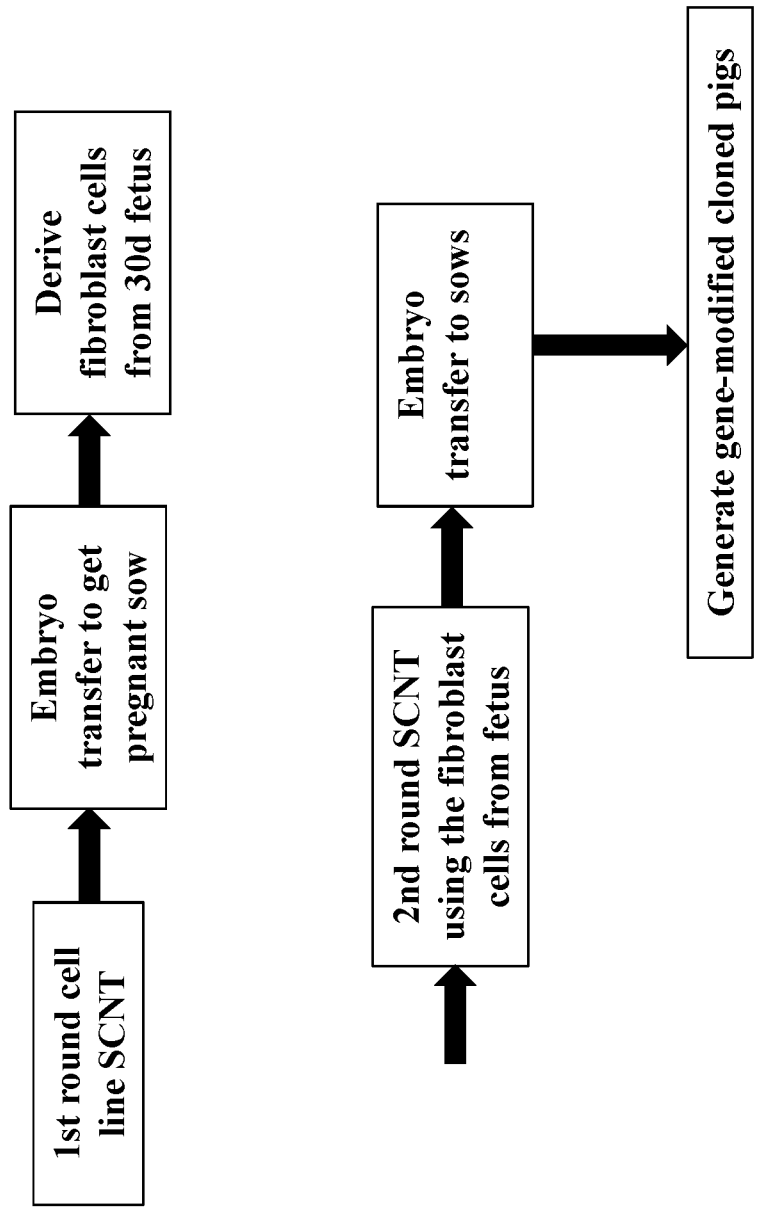
FIG. 26 shows a schematic of a method for improving cell viability conditions according to an embodiment as described herein. Briefly, fibroblast cells are isolated from 30 day fetuses and used for performing recloning by SCNT.
Figure 30:
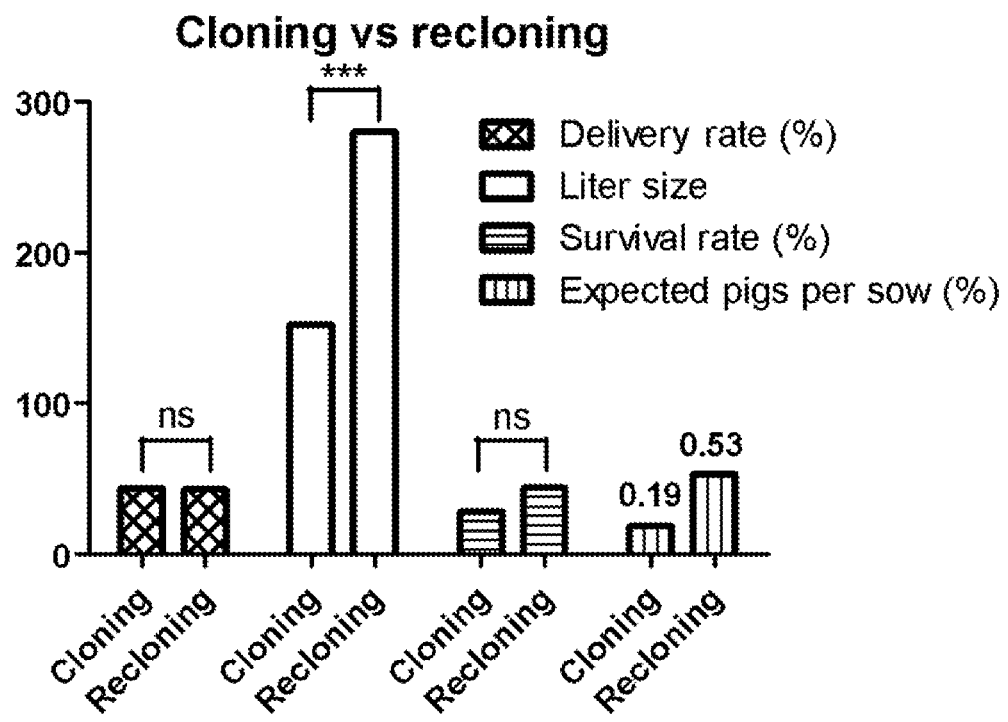
FIG. 30 demonstrates the impact of the inclusion of a recloning step during pig production on delivery rate, liter size, survival rate, and expected pigs per sow.
Figures 31A, 31B:
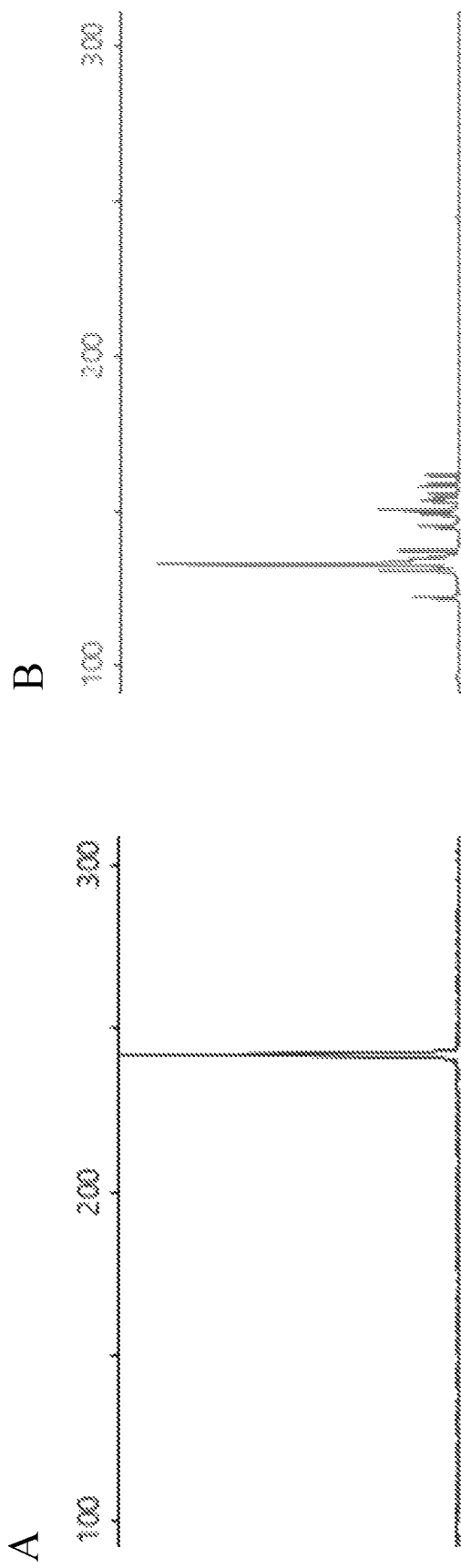
FIG. 31A shows chromatography data from PERV fragment analysis in WT pigs.
FIG. 31B shows chromatography data from PERV fragment analysis in PERV KO Yorkshire. Data shows 100% PERV KO with only large deletions, with the majority being greater than 100 base pairs (bp).

For in vitro gene editing, cellular damage is often difficult to avoid during the cell culture and transfection procedures, particularly with multiplexed editing. Therefore, an in vivo microinjection method was developed for the delivery of CRISPR/cas9 to pig zygote in order to achieve a mosaic fetus. FIG. 25. Thirty-day old fetuses were harvested and cells were extracted. Next, single cells were sorted and genotyped as single cell clones. The desired clones were expanded and used for SCNT. This strategy avoided the in vitro transfection procedure and the cells retained sufficient viability. As shown in FIG. 30, recloning significantly increased liter size and also showed an increase in survival rate, albeit a nonsignificant increase.

Example 8: Oocyte Collection and In-Vitro Maturation (IVM)

Ovaries from sexually mature gilts or sows were used for isolating cumulus-oocyte complexes (COC). Oocyte collection and IVM culture were performed as described in R. Tomii et al., J. Reprod. Dev. 55, 121-7 (2009). The oocytes surrounded with multiple layers (at least three layers) of cumulus cells were picked for maturation in-vitro in IVM medium at 38.5° C. in 5% $CO_2$, 5% 02 and 90% $N_2$ atmosphere with saturated humidity for approximately 42-44 h Example 9: Somatic Cell Nuclear Transfer (SCNT)

SCNT was performed as previously described by H. Wei et al., PLoS One. 8, e57728 (2013). The cultured COCs were freed of cumulus cells by treating with 0.1% (w/v) hyaluronidase. The first polar body contained in the oocytes and the adjacent cytoplasm was enucleated via gentle aspiration using a beveled pipette in TLH-PVA. Donor cells from a GTKOhCD55/hCD59-positive fibroblast cell line were inserted into the perivitelline space of an enucleated oocyte. The reconstructed embryos were fused with a single direct current pulse of 200 V/mm for 20 μs using the Electro Cell Fusion Generator (LF201, NEPA GENE Co., Ltd., Japan) in fusion medium (0.25 M D-sorbic alcohol, 0.05 mM $Mg(C_2H_3O_2)_2$, 20 mg/mL BSA and 0.5 mM HEPES [acid-free]). Then, the embryos were cultured for 0.5-1 h in PZM-3 and were activated with a single pulse of 150 V/mm for 100 ms in activation medium containing 0.25 M D-sorbic alcohol, 0.01 mM $Ca(C_2HO_2)_2$, 0.05 mM $Mg(C_2H_3O_2)_2$ and 0.1 mg/mL BSA. The embryos were equilibrated in PZM-3 supplemented with Spg/mL cytochalasin B for 2 h at 38.5° C. in a humidified atmosphere with 5% $CO_2$, 5% $O_2$ and 90% $N_2$ (APM-30D, ASTEC, Japan) and then cultured in PZM-3 medium with the same culture conditions described above until embryo transfer.

Example 10: Embryo Transfer

Figure 29:
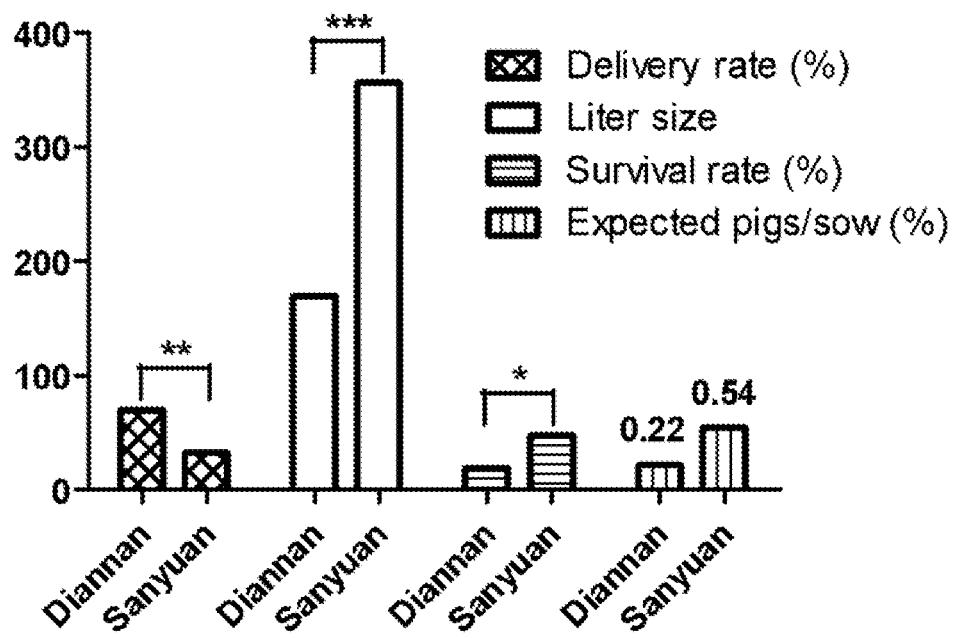
FIG. 29 demonstrates the impact of surrogate mother selection on delivery rate, liter size, survival rate, and expected pigs per sow.

For embryo transfer, sows were selected with at least one birth history and good litter size as surrogate mothers. The SCNT embryos were surgically transferred into the oviducts of the recipients. Pregnancy was confirmed approximately 23 days after surgical transfer using an ultrasound scanner (HS-101 V, Honda Electronics Co., Ltd., Yamazuka, Japan). In was determined that the selection of the surrogate can be important for pig cloning outcomes. For example, the larger the surrogate mother (e.g., Sanyuan) as compared to smaller surrogate (e.g., Diannan) the better the outcome measures in each of delivery rate, liter size, survival rate, and expected pigs per sow. FIG. 29.

Example 11: Fetus and Pig Analysis

To test whether there was any reinfection of PERVs from surrogate sows to fetuses and pigs cloned from PERV-free cells, WT and PERV knockout fetuses were collected from surrogate sows by cesarean section (c-section). Genomic DNAs and total RNAs were isolated from different tissues of cloned pigs at different time points. PERV genotypes were then checked of both genomic DNA and RNA via deep sequencing. PERV-knockout fetuses and pigs exhibited ~100% PERV inactivation efficiency both in the genome and in the transcripts of tissues. PERV copy number was confirmed to be similar to the cell line from which they were cloned. No PERV reinfection was observed in either fetuses or pigs generated by these methods.

Example 12: Increased KO Efficiency with Increasing Number of Guide RNAs Used

Figure 27:
FIG. 27 demonstrates that PERV knockout (KO) efficiency increases with the number of gRNAs used in the transfection. Fetal fibroblasts were obtained from Yucatan with 50-60 PERV copies. Chromatography data are shown from fragment analysis.

To study the impact of different number of guide RNAs on the efficiency of PERV knockout (KO), experiments were performed using 2, 3 and 4 guide RNA combinations. Briefly, PERV KO was performed in fetal fibroblast cells of the Yucatan minipig that generate contains about 50-60 PERV copies. The PERV KO efficiency was measured using fragment analysis in bulk and results determined chromatographically. It was observed that KO efficiency increased with the greater number of gRNAs. FIG. 27. Use of 2 guide RNAs resulted in 12.52% of the cells in the population having a deletion in the PERV pol sequence, while use of 3 guide RNAs resulted in 22.19% of the cells in the population having a deletion in the PERV pol sequence. When 4 guide RNAs were used the KO efficiency increased to 52.47%. Importantly, when at least 4 guide RNAs were used deletions of greater than 100 bp were observed in a significant number of cells. FIG. 27, lower right panel. It is contemplated that unlike small indels, the large deletion generated by using greater than two guide RNAs will completely remove the catalytic domain of the PERV pol, thus it cannot be reversed by spontaneous mutations.

Figure 28:
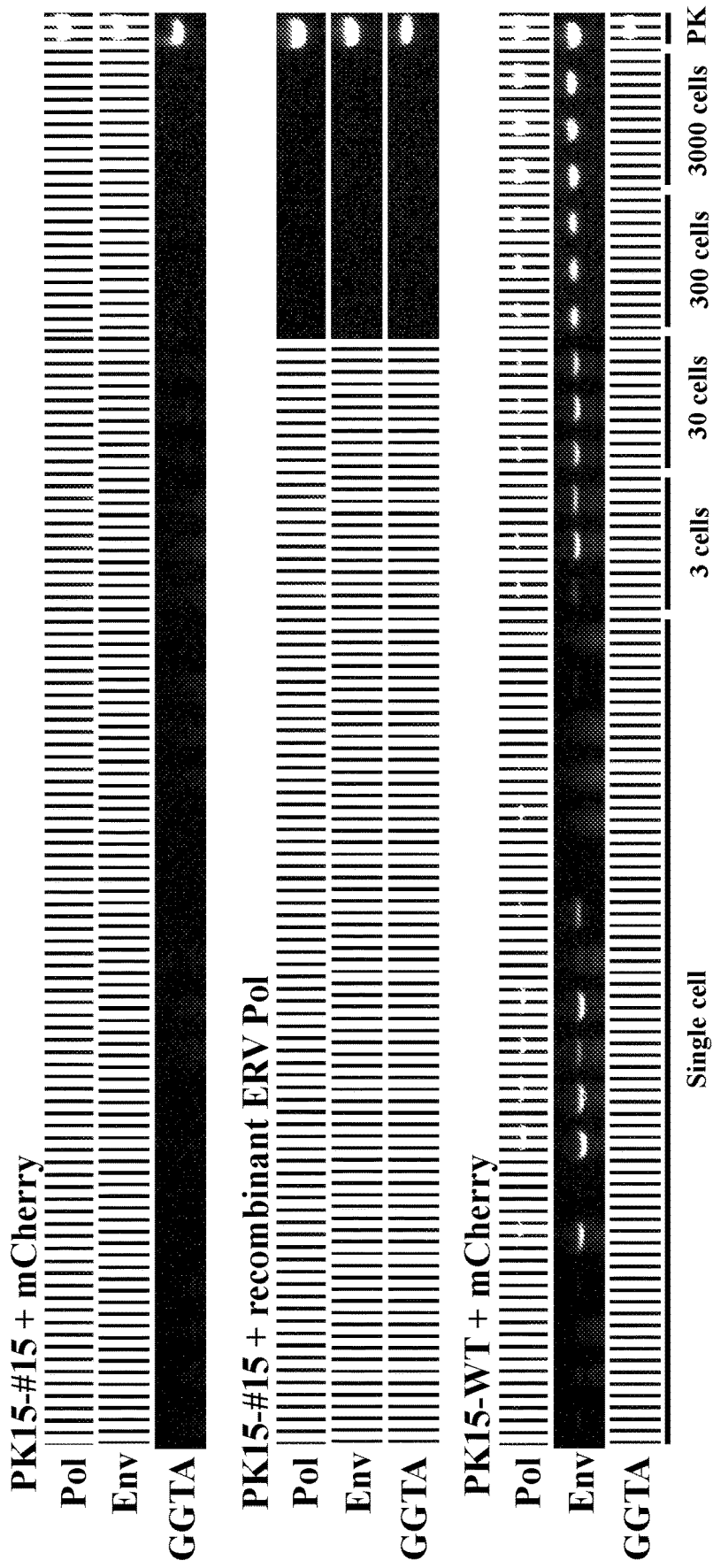
FIG. 28 depicts PCR data showing inactivated PERV pol cannot be complemented by the activity of human ERV pol.

In addition to avoiding spontaneous mutations, it was demonstrated that inactivation of PERV pol cannot be complemented by the activity of human ERV pol. FIG. 28. Briefly, PK15 WT cells ("PK15-WT+mCherry"), PERV KO cells ("PK15-#15"), and PERV KO cells expressing recombinant human ERV pol ("PK15-#15+recombinant ERV Pol) were cocultured with human 293-GFP cells. After two weeks, the 293-GFP cells were FACS isolated in the designated number and PERV infection, measured by pol and env levels, was determined using PCR. GGTA was used as negative control to show that pol/env expression resulted from PERV infection instead of the 293-GFP cells contaminated with PK15. As shown in FIG. 28, PK15-WT cells expressed both pol and env, while neither the PERV KO or the PERV KO expressing the recombinant human ERV pol showed expression of pol or env. This data demonstrates that PERVs in the PERV-inactivated pig organs will not be reactivated when exposed to human ERV.

Para A. A swine grown from an embryo, wherein the embryo comprises porcine cells having at least 75% inactive porcine endogenous retroviral (PERV) elements.

Para B. The swine of Para. A, wherein the porcine cells are a porcine female fetal fibroblast (PFFF3) cell.

Para. C. The swine of Para. A or Para. B, wherein about 100% of the PERV elements in the cells are inactive.

Para. D. The swine of any one of Paras. A-C, wherein the PERV elements comprise one or more mutations or epigenetic changes that result in decreased or eliminated activity of PERV elements.

Para. E. The swine of any one of Paras. A-D, wherein the PERV elements of the porcine cell have been inactivated by a method comprising, administering to the cell a genome modifying agent specific to a gene involved in PERV replication and/or assembly, wherein the agent disrupts transcription and/or translation of the gene.

Para. F. The swine of Para. E, wherein the agent is a nuclease or nickase or a nucleic acid encoding the nuclease or nickase.

Para. G. The swine of Para. F, wherein the nuclease or nickase is selected from the group consisting of a Zinc Finger nuclease or nickase, a TAL effector nuclease or nickase, and a CRISPR associated nuclease or nickase.

Para. H. The swine of Para. G, wherein the nuclease or nickase is a CRISPR-associated nuclease or nickase.

Para. I. The swine of Para. H., wherein the CRISPR-associated nuclease or nickase is a CRISPR-Cas9 nuclease or nickase, CRISPR-Cpf1 nuclease or nickase, or biologically active fragment or derivative thereof.

Para. J. The swine of any one of Paras. E-I, wherein the agent further comprises: a) a CRISPR guide RNA or tracrRNA or b) a nucleic acid encoding the CRISPR guide RNA.

Para. K. The swine of Para. J, wherein the CRISPR guide RNA comprises the nucleotide sequence of any one of SEQ ID NOs: 1-3 or 26-181, any strain specific genetic variant thereof, or any combination thereof.

Para. L. The swine of Para. J, wherein the CRISPR guide RNA comprises the nucleotide sequence of any one of SEQ ID NOs: 1-3 or 26-116, any strain specific genetic variant thereof, or any combination thereof.

Para. M. The swine of Para. J, wherein the CRISPR guide RNA comprises the nucleotide sequence of any one of SEQ ID NOs: 35, 36, 48, 99, 101, 102, 106, 108, 111, 113, or any combination thereof.

Para. N. The swine of any one of Paras. E-J, wherein the agent is a nucleic acid encoding the CRISPR-Cas9 nuclease or nickase, wherein the cell is engineered to stably express the agent, wherein the agent further comprises at least one guide RNA, and wherein at least one guide RNA sequence comprises the nucleotide sequence of any one of SEQ ID NOs: 1-3 or 26-116.

Para. O. The swine of Para. N wherein the agent comprises at least three guide RNAs, wherein the three guide RNA sequences comprise the nucleotide sequence of SEQ ID NOs: 1-3.

Para. P. The swine of any one of Paras. A-O, wherein the swine maintains a same or substantially same level of PERV inactivation for at least a month, at least 6 months, at least 1 year, at least 5 years, at least 10 years post-gestation.

Para. Q. An organ or tissue obtained from the swine of any one of Paras. A-P.

Para. R. A method of transplanting the organ or tissue of Para. Q to a subject, comprising the step of transplanting the organ into the subject.

Para. S. The method of Para. R, wherein the subject is a human.

Para. T. The method of Para. R, wherein the subject is a non-human primate.

Para. U. A method of generating a porcine endogenous retrovirus (PERV)-inactivated pig comprising: obtaining a nuclear donor cell having a nucleus, wherein at least 75% of the PERV elements in the nuclear donor cell are inactive; transferring the nucleus of the nuclear donor cell into a recipient enucleated oocyte to generate nucleus-transferred oocyte; subjecting the nucleus-transferred oocyte to activation; culturing the nucleus-transferred oocyte to generate a blastocyst or embryo; transferring the blastocyst or embryo to a surrogate; and generating a living PERV-inactivated pig from the blastocyst or embryo.

Para. V. A method of generating a porcine endogenous retrovirus (PERV)-inactivated pig comprising: using a nucleus from a nuclear donor cell to generate a blastocyst or embryo, wherein at least 75% of the PERV elements in the nuclear donor cell are inactive; and transferring the blastocyst or embryo to a surrogate to generate a PERV-inactivated pig.

Para. W. The method of Para. U or Para. V wherein the nuclear donor cell is a fetal cell.

Para. X. The method of Para. U or Para. V wherein the nuclear donor cell is isolated from a chimeric PERV-inactivated fetus.

Para. Y. The method of Para. X wherein the chimeric PERV-inactivated fetus is at about 10 days, about 20 days, about 30 days, or about 3 months gestation.

Para. Z. The method of Para. X wherein the chimeric PERV-inactivated fetus is generated using a genome modifying agent.

Para AA. The method of Para. Z wherein the chimeric PERV-inactivated fetus is generated by zygote injection.

Para AB. The method of Para. Z wherein the genome modifying agent is selected from the group consisting of Zinc Finger nuclease or nickase, TAL effector nuclease or nickase, deaminase, and CRISPR associate nuclease or nickase.

Para. AC. The method of Para. U or Para. V wherein the nuclear donor cell is expanded in vitro.

Para. AD. The method of Para. AC wherein the nuclear donor cell undergoes less than 30, less than 20, less than 10, less than 5, or less than 2 population doublings in vitro.

Para. AE. The method of Para. U or Para. V wherein the nuclear donor cell is a somatic cell.

Para. AF. The method of Para. U or Para. V wherein the nuclear donor cell is selected from the group consisting of a fetal muscle cell, a fibroblast, endothelium cell, liver cell.

Para. AG. The method of Para. U or Para. V wherein the nuclear donor cell is isolated from a pig.

Para. AH. The method of Para. AG wherein the pig is less than 10 weeks, less than 8 weeks, less than 6 weeks, less than 5 weeks, less than 4 weeks, less than 3 weeks, less than 2 weeks, or less than 1 week in age.

Para. AI. The method of Para. U or Para. V wherein at least about 80%, at least about 90%, at least about 95%, at least about 99% of the PERV elements in the nuclear donor cell are inactive.

Para. AJ. The method of Para. U or Para. V wherein 100% of the PERV elements in the nuclear donor cell are inactive.

Para. AK. The method of Para. U or Para. V wherein the PERV-inactivated pig maintains a same or similar level of PERV inactivation for at least a month, at least 6 months, at least 1 year, at least 5 years, at least 10 years post-gestation.

Para. AL. The method of Para. U or Para. V wherein the PERV-inactivated pig is a PERV-free pig.

Para. AM. The method of Para. U or Para. V wherein the PERV-inactivated pig has at least 75%, at least 80%, at least 85%, at least 90%, at least 95%, or at least 99% inactive PERV elements.

Para. AN. The method of Para. U or Para. V further comprising a deacetylase inhibitor.

Para. AO. The method of Para. U or Para. V further comprising transferring at least one wild type blastocyst or embryo to the surrogate.

Para. AP. An isolated porcine cell generated by the methods of any one of Paras. U to AO.

Para. AQ. An organ or tissue obtained from a cell generated by the methods of any one of Paras. U to AO.

Para. AR. A method of improving the birth rate of PERV-inactivated pigs comprising: using nuclei from nuclear donor cells to generate blastocysts or embryos, wherein at least 75% of the PERV elements in the nuclear donor cells are inactive; and transferring the blastocysts or embryos to at least one surrogate to generate at least one PERV-inactivated pig, wherein the miscarriage rate is reduced as compared to the miscarriage rate of fetuses generated from a cell wherein more than 25% of the PERV elements in the cell are active.

Para. AS. A method of generating a genetically modified animal comprising: using a nucleus from a nuclear donor cell to generate a blastocyst or embryo, wherein a plurality of nucleic acid sequences in the nuclear donor cell are modified; and transferring the blastocyst or embryo to a surrogate to generate the genetically modified animal.

Para. AT. The method of Paras. AR or AS wherein the nuclear donor cell is a fetal cell.

Para. AU. The method of Paras. AR or AS wherein the nuclear donor cell is isolated from a chimeric fetus.

Para. AV. The method of Paras. AR or AS wherein the chimeric fetus is at about 10 days, about 20 days, about 30 days, or about 3 months gestation.

Para. AW. The method of Para. AV wherein the chimeric fetus is generated using a genome modifying agent.

Para. AX. The method of Para. AU wherein the chimeric fetus is generated by zygote injection.

Para. AY. The method of Para. AW wherein the genome modifying agent is selected from the group consisting of Zinc Finger nuclease or nickase, TAL effector nuclease or nickase, deaminase, and CRISPR associate nuclease or nickase.

Para. AZ. The method of Paras. AR or AS wherein the nuclear donor cell is expanded in vitro.

Para BA. The method of Para. AZ wherein the nuclear donor cell undergoes less than 30, less than 20, less than 10, less than 5, or less than 2 population doublings in vitro.

Para BB. The method of Paras. AR or AS wherein the nuclear donor cell is a somatic cell.

Para. BC. The method of Paras. AR or AS wherein the nuclear donor cell is selected from the group consisting of a fetal muscle cell, a fibroblast, endothelium cell, liver cell.

Para. BD. The method of Paras. AR or AS wherein the nuclear donor cell is isolated from an animal that is less than 10 weeks, less than 8 weeks, less than 6 weeks, less than 5 weeks, less than 4 weeks, less than 3 weeks, less than 2 weeks, or less than 1 week in age.

Para. BE. The method of Paras. AR or AS wherein the plurality of nucleic acid sequences are modified by inactivation, insertion of exogenous nucleic acids, subtraction of endogenous nucleic acids, or any combination thereof.

Para. BF. The method of Paras. AR or AS wherein at least about 2, at least about 5, at least about 10, at least about 20, at least about 30, at least about 40, at least about 50, at least about 60, at least about 70, at least about 80, at least about 90, at least about 100, or more nucleic acid sequences are modified.

Para. BG. A method of preventing or reducing risk of pregnancy loss or miscarriage following somatic cell nuclear transfer (SCNT) of a genetically modified blastocyst or embryo comprising: using a nucleus from a genetically modified nuclear donor cell to generate a blastocyst or embryo; and transferring the blastocyst or embryo to a surrogate to generate at least one a viable offspring wherein the rate of pregnancy loss or miscarriage is reduced as compared to the rate of pregnancy loss or miscarriage of a control.

Para. BH. The method of Para. BG wherein the genetically modified nuclear donor cell has a plurality of genetic modifications.

Para. BI. The method of Para. BH wherein the plurality of genetic modifications comprise at least about 2, at least about 3, at least about 4, at least about 5, at least about 10, at least about 15, at least about 20, at least about 30, at least about 40, at least about 50, at least about 60, at least about 70, at least about 80, at least about 90, or at least about 100 genetic modifications.

Para. BJ. The method of Para. BG wherein the plurality of genetic modifications are to a single, repetitive gene sequence.

Para. BK. The method of Para. BG wherein at least a portion of the genetic modifications are to different genes.

Para. BL. The method of Para. BG wherein the genetically modified nuclear donor cell has been modified using a genome modifying agent selected from the group consisting of Zinc Finger nuclease or nickase, TAL effector nuclease or nickase, deaminase, and CRISPR associate nuclease or nickase.

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

I claim:

1. A method of generating a genetically modified pig comprising inactivated porcine endogenous retrovirus (PERV) genes; the method comprising:
   i. introducing a 1$^{st}$ and 2$^{nd}$ guide RNA (gRNA) that target a nucleic acid sequence selected from the group consisting of SEQ ID NOS: 1, 3, 26-107, 110-124, 126-148, and 150-181 and a CRISPR endonuclease into isolated somatic pig cells;
   ii. transferring the nucleus of a cell obtained in step i) into an enucleated pig oocyte;
   iii. culturing the oocyte obtained in step ii) such that a blastocyst is obtained;
   iv. transferring the blastocyst into a surrogate pig; and
   v. obtaining a genetically modified pig from the blastocyst transferred in step iv) in which at least 75% of PERV pol genes are inactivated in each cell of the pig as compared to the isolated somatic pig cells prior to introducing the 1$^{st}$ and 2$^{nd}$ gRNA and the CRISPR endonuclease.

2. The method of claim 1, wherein the isolated somatic pig cells are fetal cells.

3. The method of claim 1, wherein the isolated somatic pig cells are isolated from a chimeric PERV-inactivated fetus.

4. The method of claim 3, wherein the chimeric PERV-inactivated fetus is isolated at less than about 9 months gestation.

5. The method of claim 1, wherein the isolated somatic pig cells undergo less than 30 population doublings in vitro.

6. The method of claim 1, wherein the isolated somatic pig cells are isolated from a pig that is less than 10 weeks in age.

7. The method of claim 1, wherein at least 80% of the PERV pol genes in each cell comprise a genetically introduced deletion of at least 100 base pairs.

8. The method of claim 1, wherein the genetically modified pig maintains a same or similar level of PERV inactivation for at least a month post-gestation.

9. The method of claim 1, comprising transferring at least one wild-type blastocyst or embryo to the surrogate pig.

10. The method of claim 1, wherein the isolated somatic pig cells are porcine fetal fibroblasts.

11. The method of claim 1, wherein the isolated somatic pig cells are adult cells.

12. The method of claim 11, wherein the adult cells are adult ear fibroblasts.

13. The method of claim 1, wherein the isolated somatic pig cells are obtained from a Yucatan pig.

14. The method of claim 1, wherein the isolated somatic pig cells are obtained from a Yorkshire pig.

15. The method of claim 1, wherein the PERV pol genes comprise a deletion of greater than about 150 bp.

16. The method of claim 1, wherein the CRISPR endonuclease comprises a Cas9 protein.

17. The method of claim 7, wherein the genetically introduced deletion is generated by introducing to the isolated somatic pig cells a CRISPR based agent comprising at least four CRISPR gRNAs.

18. The method of claim 1, wherein the blastocyst is resistant to PERV reinfection.

19. The method of claim 1, wherein the genome of the isolated somatic pig cells does not encode a Cas9 protein.

20. The method of claim 1, comprising administering a p53 inhibitor to the isolated somatic pig cells.

21. The method of claim 1, comprising administering a growth factor to the isolated somatic pig cells.

22. The method of claim 7, comprising administering a p53 inhibitor and a growth factor to the isolated somatic pig cells before generating the genetically introduced deletion in the isolated somatic pig cells.

23. The method of claim 21, wherein the growth factor is selected from the group consisting of epidermal growth factor (EGF), insulin-like growth factor (IGF), platelet derived growth factor (PDGF), vascular endothelial growth factor (VEGF), keratinocyte growth factor), basic fibroblast growth factor (bFGF), and fibroblast growth factor-2 (FGF-2).

24. The method of claim 20, wherein the p53 inhibitor is selected from the group consisting of pifithrin-alpha, pifithrin-beta, pifithrin-alpha hydrobromide, pifithrin-mu, ellipticine, 9-hydroxyellipticine, nutlin-3, roscovitine, and SJ 172550.

25. The method of claim 1, wherein the 1$^{st}$ and 2nd gRNA target PERV pol genes comprising a nucleic acid sequence selected from the group consisting of SEQ ID NOS: 48, 99, 101, 102, 111, and 138.

26. The method of claim 1, wherein the 1$^{st}$ and 2$^{nd}$ gRNA target PERV pol genes comprising a nucleic acid sequence selected from the group consisting of SEQ ID NOS: 102, 48, and 99.

27. The method of claim 1, wherein the 1$^{st}$ and 2$^{nd}$ gRNA target PERV pol genes comprising a nucleic acid sequence a guide RNA cutting site on the genome of the PERV pol gene selected from the group consisting of SEQ ID NOS: 102, 99, 138, and 101.

28. The method of claim 1, wherein the 1$^{st}$ and 2$^{nd}$ gRNA target PERV pol genes comprising a nucleic acid sequence selected from the group consisting of SEQ ID NOS: 102, 48, 138, and 101.

29. The method of claim 1, wherein about 100% of the PERV pol genes in each cell are inactivated.

30. The method of claim 1, wherein the 1$^{st}$ and 2$^{nd}$ gRNA bind to different target sites.

* * * * *

```
                              SEQUENCE LISTING

<160> NUMBER OF SEQ ID NOS: 231

<210> SEQ ID NO 1
<211> LENGTH: 22
<212> TYPE: DNA
<213> ORGANISM: Sus scrofa

<400> SEQUENCE: 1
ggtaccctcc tccagtacgt gg                                                  22

<210> SEQ ID NO 2
<211> LENGTH: 23
<212> TYPE: DNA
<213> ORGANISM: Sus scrofa

<400> SEQUENCE: 2
ggtcatccac gtactggagg agg                                                 23

<210> SEQ ID NO 3
<211> LENGTH: 23
<212> TYPE: DNA
<213> ORGANISM: Sus scrofa

<400> SEQUENCE: 3
ggtcatccac gtactggatg agg                                                 23

<210> SEQ ID NO 4
<211> LENGTH: 53
<212> TYPE: DNA
<213> ORGANISM: Sus scrofa

<400> SEQUENCE: 4
acactctttc cctacacgac gctcttccga tctcgactgc cccaagggtt caa               53

<210> SEQ ID NO 5
<211> LENGTH: 55
<212> TYPE: DNA
<213> ORGANISM: Sus scrofa

<400> SEQUENCE: 5
gtgactggag ttcagacgtg tgctcttccg atcttctctc ctgcaaatct gggcc             55

<210> SEQ ID NO 6
<211> LENGTH: 20
<212> TYPE: DNA
<213> ORGANISM: Sus scrofa

<400> SEQUENCE: 6
ctgcatgacc agggtttatg                                                     20

<210> SEQ ID NO 7
<211> LENGTH: 90
<212> TYPE: RNA
<213> ORGANISM: Sus scrofa
<220> FEATURE:
<221> NAME/KEY: misc_feature
<222> LOCATION: (1)..(6)
<223> OTHER INFORMATION: phosphodiester bond
<220> FEATURE:
```

```
<221> NAME/KEY: misc_feature
<222> LOCATION: (85)..(90)
<223> OTHER INFORMATION: phosphodiester bond

<400> SEQUENCE: 7
aacauggaac cuuuggcccu guucauuuua gaaaucaagu caagauacgc agaagaguag    60
acauaaaccc uggucaugca gaccucagug                                    90

<210> SEQ ID NO 8
<211> LENGTH: 20
<212> TYPE: DNA
<213> ORGANISM: Sus scrofa

<400> SEQUENCE: 8
acctttggcc ctgttcattt                                               20

<210> SEQ ID NO 9
<211> LENGTH: 23
<212> TYPE: DNA
<213> ORGANISM: Sus scrofa

<400> SEQUENCE: 9
ttcgcctcag aatagaaact cag                                           23

<210> SEQ ID NO 10
<211> LENGTH: 23
<212> TYPE: DNA
<213> ORGANISM: Sus scrofa

<400> SEQUENCE: 10
gttaggagat ggcctctgtt ctt                                           23

<210> SEQ ID NO 11
<211> LENGTH: 28
<212> TYPE: DNA
<213> ORGANISM: Sus scrofa
<220> FEATURE:
<221> NAME/KEY: misc_signal
<222> LOCATION: (1)..(1)
<223> OTHER INFORMATION: 56-FAM
<220> FEATURE:
<221> NAME/KEY: misc_signal
<222> LOCATION: (28)..(28)
<223> OTHER INFORMATION: 3BHQ_1

<400> SEQUENCE: 11
ccaaacccTt atttggtcct atagcaac                                      28

<210> SEQ ID NO 12
<211> LENGTH: 23
<212> TYPE: DNA
<213> ORGANISM: Sus scrofa

<400> SEQUENCE: 12
gggcaagtac aaagtgatga aac                                           23

<210> SEQ ID NO 13
<211> LENGTH: 23
<212> TYPE: DNA
<213> ORGANISM: Sus scrofa

<400> SEQUENCE: 13
attccccagc tcataccatt tat                                           23
```

```
<210> SEQ ID NO 14
<211> LENGTH: 29
<212> TYPE: DNA
<213> ORGANISM: Sus scrofa
<220> FEATURE:
<221> NAME/KEY: misc_signal
<222> LOCATION: (1)..(1)
<223> OTHER INFORMATION: 56-FAM
<220> FEATURE:
<221> NAME/KEY: misc_signal
<222> LOCATION: (29)..(29)
<223> OTHER INFORMATION: 3BHQ_1

<400> SEQUENCE: 14
ataagagctg ctccccatca gacttagat                              29

<210> SEQ ID NO 15
<211> LENGTH: 23
<212> TYPE: DNA
<213> ORGANISM: Sus scrofa

<400> SEQUENCE: 15
taaatggtat gtcttgggga atg                                    23

<210> SEQ ID NO 16
<211> LENGTH: 23
<212> TYPE: DNA
<213> ORGANISM: Sus scrofa

<400> SEQUENCE: 16
agaccgtatt tggtcctata gcc                                    23

<210> SEQ ID NO 17
<211> LENGTH: 24
<212> TYPE: DNA
<213> ORGANISM: Sus scrofa
<220> FEATURE:
<221> NAME/KEY: misc_signal
<222> LOCATION: (1)..(1)
<223> OTHER INFORMATION: 56-FAM
<220> FEATURE:
<221> NAME/KEY: misc_signal
<222> LOCATION: (24)..(24)
<223> OTHER INFORMATION: 3BHQ_1

<400> SEQUENCE: 17
cctggttgtt tacccgagcc tcca                                   24

<210> SEQ ID NO 18
<211> LENGTH: 20
<212> TYPE: DNA
<213> ORGANISM: Sus scrofa

<400> SEQUENCE: 18
cgactgcccc aagggttcaa                                        20

<210> SEQ ID NO 19
<211> LENGTH: 21
<212> TYPE: DNA
<213> ORGANISM: Sus scrofa

<400> SEQUENCE: 19
ccgactgccc caagagttca a                                      21

<210> SEQ ID NO 20
<211> LENGTH: 24
<212> TYPE: DNA
```

```
<213> ORGANISM: Sus scrofa
<220> FEATURE:
<221> NAME/KEY: misc_signal
<222> LOCATION: (1)..(1)
<223> OTHER INFORMATION: 56-FAM

<400> SEQUENCE: 20
cacgtactgg aggagggtca cctg                                          24

<210> SEQ ID NO 21
<211> LENGTH: 22
<212> TYPE: DNA
<213> ORGANISM: Sus scrofa

<400> SEQUENCE: 21
ccgcgatcta atgttctctt tc                                            22

<210> SEQ ID NO 22
<211> LENGTH: 20
<212> TYPE: DNA
<213> ORGANISM: Sus scrofa

<400> SEQUENCE: 22
ttcactccga ccttcaccat                                               20

<210> SEQ ID NO 23
<211> LENGTH: 20
<212> TYPE: DNA
<213> ORGANISM: Sus scrofa
<220> FEATURE:
<221> NAME/KEY: misc_signal
<222> LOCATION: (1)..(1)
<223> OTHER INFORMATION: 5HEX

<400> SEQUENCE: 23
cagccgcgtc cctgagacac                                               20

<210> SEQ ID NO 24
<211> LENGTH: 18
<212> TYPE: DNA
<213> ORGANISM: Sus scrofa

<400> SEQUENCE: 24 atgccccga attccaga                                                  18

<210> SEQ ID NO 25
<211> LENGTH: 23
<212> TYPE: DNA
<213> ORGANISM: Sus scrofa

<400> SEQUENCE: 25
ggttaggttg cattttcatc ctt                                           23

<210> SEQ ID NO 26
<211> LENGTH: 23
<212> TYPE: DNA
<213> ORGANISM: Sus scrofa

<400> SEQUENCE: 26
atactcccct gctaccggtt agg                                           23

<210> SEQ ID NO 27
<211> LENGTH: 23
<212> TYPE: DNA
<213> ORGANISM: Sus scrofa
```

```
<400> SEQUENCE: 27
caatgattat cgaccagtac agg                                          23

<210> SEQ ID NO 28
<211> LENGTH: 23
<212> TYPE: DNA
<213> ORGANISM: Sus scrofa

<400> SEQUENCE: 28
acttgagaga ggtcaataaa agg                                          23

<210> SEQ ID NO 29
<211> LENGTH: 23
<212> TYPE: DNA
<213> ORGANISM: Sus scrofa

<400> SEQUENCE: 29
tgagcgccct cccgcctgaa cgg                                          23

<210> SEQ ID NO 30
<211> LENGTH: 23
<212> TYPE: DNA
<213> ORGANISM: Sus scrofa

<400> SEQUENCE: 30
aaccactttt tgccttcgaa tgg                                          23

<210> SEQ ID NO 31
<211> LENGTH: 23
<212> TYPE: DNA
<213> ORGANISM: Sus scrofa

<400> SEQUENCE: 31
gatccaggta cgggaagaac cgg                                          23

<210> SEQ ID NO 32
<211> LENGTH: 23
<212> TYPE: DNA
<213> ORGANISM: Sus scrofa

<400> SEQUENCE: 32
acctggaccc gactgcccca agg                                          23

<210> SEQ ID NO 33
<211> LENGTH: 23
<212> TYPE: DNA
<213> ORGANISM: Sus scrofa

<400> SEQUENCE: 33
cgaagcccta cacagagacc tgg                                          23

<210> SEQ ID NO 34
<211> LENGTH: 23
<212> TYPE: DNA
<213> ORGANISM: Sus scrofa

<400> SEQUENCE: 34
cttcaggatc caacaccctc agg                                          23

<210> SEQ ID NO 35
<211> LENGTH: 23
<212> TYPE: DNA
```

<213> ORGANISM: Sus scrofa

<400> SEQUENCE: 35
gtacgtggat gacctgcttc tgg                                          23

<210> SEQ ID NO 36
<211> LENGTH: 23
<212> TYPE: DNA
<213> ORGANISM: Sus scrofa

<400> SEQUENCE: 36
accaaacagg actgcttaga agg                                          23

<210> SEQ ID NO 37
<211> LENGTH: 23
<212> TYPE: DNA
<213> ORGANISM: Sus scrofa

<400> SEQUENCE: 37
ctgctggaat tgtctgacct agg                                          23

<210> SEQ ID NO 38
<211> LENGTH: 23
<212> TYPE: DNA
<213> ORGANISM: Sus scrofa

<400> SEQUENCE: 38
ctacagagcc tctgctaaga agg                                          23

<210> SEQ ID NO 39
<211> LENGTH: 23
<212> TYPE: DNA
<213> ORGANISM: Sus scrofa

<400> SEQUENCE: 39
caggagagag gtaacatact tgg                                          23

<210> SEQ ID NO 40
<211> LENGTH: 23
<212> TYPE: DNA
<213> ORGANISM: Sus scrofa

<400> SEQUENCE: 40
ggcttcctaa ccggtagcag ggg                                          23

<210> SEQ ID NO 41
<211> LENGTH: 23
<212> TYPE: DNA
<213> ORGANISM: Sus scrofa

<400> SEQUENCE: 41
ctgtactggt cgataatcat tgg                                          23

<210> SEQ ID NO 42
<211> LENGTH: 23
<212> TYPE: DNA
<213> ORGANISM: Sus scrofa

<400> SEQUENCE: 42
tataagggtt cgggaccgtt ggg                                          23

<210> SEQ ID NO 43
<211> LENGTH: 23

```
<212> TYPE: DNA
<213> ORGANISM: Sus scrofa

<400> SEQUENCE: 43
caggcgggag ggcgctcaag agg                                              23

<210> SEQ ID NO 44
<211> LENGTH: 23
<212> TYPE: DNA
<213> ORGANISM: Sus scrofa

<400> SEQUENCE: 44
gtgtaatctc aggcagaaga agg                                              23

<210> SEQ ID NO 45
<211> LENGTH: 23
<212> TYPE: DNA
<213> ORGANISM: Sus scrofa

<400> SEQUENCE: 45
gcaaaaagtg gttggctagt ggg                                              23

<210> SEQ ID NO 46
<211> LENGTH: 23
<212> TYPE: DNA
<213> ORGANISM: Sus scrofa

<400> SEQUENCE: 46
tgcccggttc ttcccgtacc tgg                                              23

<210> SEQ ID NO 47
<211> LENGTH: 23
<212> TYPE: DNA
<213> ORGANISM: Sus scrofa

<400> SEQUENCE: 47
cccttggggc agtcgggtcc agg                                              23

<210> SEQ ID NO 48
<211> LENGTH: 23
<212> TYPE: DNA
<213> ORGANISM: Sus scrofa

<400> SEQUENCE: 48
ggcttcgtca aagatggtcg ggg                                              23

<210> SEQ ID NO 49
<211> LENGTH: 23
<212> TYPE: DNA
<213> ORGANISM: Sus scrofa

<400> SEQUENCE: 49
gttggatcct gaagttggcc agg                                              23

<210> SEQ ID NO 50
<211> LENGTH: 23
<212> TYPE: DNA
<213> ORGANISM: Sus scrofa

<400> SEQUENCE: 50
actggaggag ggtcacctga ggg                                              23

<210> SEQ ID NO 51
```

```
<211> LENGTH: 23
<212> TYPE: DNA
<213> ORGANISM: Sus scrofa

<400> SEQUENCE: 51
tggtggctcc cgccagaagc agg                                              23

<210> SEQ ID NO 52
<211> LENGTH: 23
<212> TYPE: DNA
<213> ORGANISM: Sus scrofa

<400> SEQUENCE: 52
tagcagaggc tctgtagcct agg                                              23

<210> SEQ ID NO 53
<211> LENGTH: 23
<212> TYPE: DNA
<213> ORGANISM: Sus scrofa

<400> SEQUENCE: 53
tacctctctc ctgcaaatct ggg                                              23

<210> SEQ ID NO 54
<211> LENGTH: 23
<212> TYPE: DNA
<213> ORGANISM: Sus scrofa

<400> SEQUENCE: 54
ctgctaccgg ttaggaagcc tgg                                              23

<210> SEQ ID NO 55
<211> LENGTH: 23
<212> TYPE: DNA
<213> ORGANISM: Sus scrofa

<400> SEQUENCE: 55
aggcttccta accggtagca ggg                                              23

<210> SEQ ID NO 56
<211> LENGTH: 23
<212> TYPE: DNA
<213> ORGANISM: Sus scrofa

<400> SEQUENCE: 56
caggcttcct aaccggtagc agg                                              23

<210> SEQ ID NO 57
<211> LENGTH: 23
<212> TYPE: DNA
<213> ORGANISM: Sus scrofa

<400> SEQUENCE: 57
ttggtcccag gcttcctaac cgg                                              23

<210> SEQ ID NO 58
<211> LENGTH: 23
<212> TYPE: DNA
<213> ORGANISM: Sus scrofa

<400> SEQUENCE: 58
acctctctca gtcctgtac tgg                                               23
```

-continued

```
<210> SEQ ID NO 59
<211> LENGTH: 23
<212> TYPE: DNA
<213> ORGANISM: Sus scrofa

<400> SEQUENCE: 59
tgctaccggt taggaagcct ggg                                             23

<210> SEQ ID NO 60
<211> LENGTH: 23
<212> TYPE: DNA
<213> ORGANISM: Sus scrofa

<400> SEQUENCE: 60
ggtcgataat cattggtccc agg                                             23

<210> SEQ ID NO 61
<211> LENGTH: 23
<212> TYPE: DNA
<213> ORGANISM: Sus scrofa

<400> SEQUENCE: 61
accagtacag gacttgagag agg                                             23

<210> SEQ ID NO 62
<211> LENGTH: 23
<212> TYPE: DNA
<213> ORGANISM: Sus scrofa

<400> SEQUENCE: 62
ggtgcaggac atacacccaa cgg                                             23

<210> SEQ ID NO 63
<211> LENGTH: 23
<212> TYPE: DNA
<213> ORGANISM: Sus scrofa

<400> SEQUENCE: 63
cttgagagag gtcaataaaa ggg                                             23

<210> SEQ ID NO 64
<211> LENGTH: 23
<212> TYPE: DNA
<213> ORGANISM: Sus scrofa

<400> SEQUENCE: 64
agaggtcaat aaaagggtgc agg                                             23

<210> SEQ ID NO 65
<211> LENGTH: 23
<212> TYPE: DNA
<213> ORGANISM: Sus scrofa

<400> SEQUENCE: 65
ttataagggt tcgggaccgt tgg                                             23

<210> SEQ ID NO 66
<211> LENGTH: 23
<212> TYPE: DNA
<213> ORGANISM: Sus scrofa

<400> SEQUENCE: 66
tcaagaggtt ataagggttc ggg                                             23
```

```
<210> SEQ ID NO 67
<211> LENGTH: 23
<212> TYPE: DNA
<213> ORGANISM: Sus scrofa

<400> SEQUENCE: 67
ccagttccgt tcaggcggga ggg                                             23

<210> SEQ ID NO 68
<211> LENGTH: 23
<212> TYPE: DNA
<213> ORGANISM: Sus scrofa

<400> SEQUENCE: 68
ctcaagaggt tataagggtt cgg                                             23

<210> SEQ ID NO 69
<211> LENGTH: 23
<212> TYPE: DNA
<213> ORGANISM: Sus scrofa

<400> SEQUENCE: 69
gggcgctcaa gaggttataa ggg                                             23

<210> SEQ ID NO 70
<211> LENGTH: 23
<212> TYPE: DNA
<213> ORGANISM: Sus scrofa

<400> SEQUENCE: 70
tgtaccagtt ccgttcaggc ggg                                             23

<210> SEQ ID NO 71
<211> LENGTH: 23
<212> TYPE: DNA
<213> ORGANISM: Sus scrofa

<400> SEQUENCE: 71
agggcgctca agaggttata agg                                             23

<210> SEQ ID NO 72
<211> LENGTH: 23
<212> TYPE: DNA
<213> ORGANISM: Sus scrofa

<400> SEQUENCE: 72
acggaactgg tacacagtat tgg                                             23

<210> SEQ ID NO 73
<211> LENGTH: 23
<212> TYPE: DNA
<213> ORGANISM: Sus scrofa

<400> SEQUENCE: 73
accagttccg ttcaggcggg agg                                             23

<210> SEQ ID NO 74
<211> LENGTH: 23
<212> TYPE: DNA
<213> ORGANISM: Sus scrofa

<400> SEQUENCE: 74
gtgtaccagt tccgttcagg cgg                                             23
```

```
<210> SEQ ID NO 75
<211> LENGTH: 23
<212> TYPE: DNA
<213> ORGANISM: Sus scrofa

<400> SEQUENCE: 75
actgtgtacc agttccgttc agg                                              23

<210> SEQ ID NO 76
<211> LENGTH: 23
<212> TYPE: DNA
<213> ORGANISM: Sus scrofa

<400> SEQUENCE: 76
ggctagtggg gtgtaatctc agg                                              23

<210> SEQ ID NO 77
<211> LENGTH: 23
<212> TYPE: DNA
<213> ORGANISM: Sus scrofa

<400> SEQUENCE: 77
ctccattcga aggcaaaaag tgg                                              23

<210> SEQ ID NO 78
<211> LENGTH: 23
<212> TYPE: DNA
<213> ORGANISM: Sus scrofa

<400> SEQUENCE: 78
caaaaagtgg ttggctagtg ggg                                              23

<210> SEQ ID NO 79
<211> LENGTH: 23
<212> TYPE: DNA
<213> ORGANISM: Sus scrofa

<400> SEQUENCE: 79
acctggatct ctccattcga agg                                              23

<210> SEQ ID NO 80
<211> LENGTH: 23
<212> TYPE: DNA
<213> ORGANISM: Sus scrofa

<400> SEQUENCE: 80
tcgggtccag gtgagctgcc cgg                                              23

<210> SEQ ID NO 81
<211> LENGTH: 23
<212> TYPE: DNA
<213> ORGANISM: Sus scrofa

<400> SEQUENCE: 81
ggggagttct tgaacccttg ggg                                              23

<210> SEQ ID NO 82
<211> LENGTH: 23
<212> TYPE: DNA
<213> ORGANISM: Sus scrofa

<400> SEQUENCE: 82
```
gtgtagggct tcgtcaaaga tgg                                              23

<210> SEQ ID NO 83
<211> LENGTH: 23
<212> TYPE: DNA
<213> ORGANISM: Sus scrofa

<400> SEQUENCE: 83
ggcaaaaagt ggttggctag tgg                                              23

<210> SEQ ID NO 84
<211> LENGTH: 23
<212> TYPE: DNA
<213> ORGANISM: Sus scrofa

<400> SEQUENCE: 84
attcgaaggc aaaaagtggt tgg                                              23

<210> SEQ ID NO 85
<211> LENGTH: 23
<212> TYPE: DNA
<213> ORGANISM: Sus scrofa

<400> SEQUENCE: 85
gccttcgaat ggagagatcc agg                                              23

<210> SEQ ID NO 86
<211> LENGTH: 23
<212> TYPE: DNA
<213> ORGANISM: Sus scrofa

<400> SEQUENCE: 86
gaagaaccgg gcagctcacc tgg                                              23

<210> SEQ ID NO 87
<211> LENGTH: 23
<212> TYPE: DNA
<213> ORGANISM: Sus scrofa

<400> SEQUENCE: 87
cgaatggaga gatccaggta cgg                                              23

<210> SEQ ID NO 88
<211> LENGTH: 23
<212> TYPE: DNA
<213> ORGANISM: Sus scrofa

<400> SEQUENCE: 88
gaatggagag atccaggtac ggg                                              23

<210> SEQ ID NO 89
<211> LENGTH: 23
<212> TYPE: DNA
<213> ORGANISM: Sus scrofa

<400> SEQUENCE: 89
atccaggtac gggaagaacc ggg                                              23

<210> SEQ ID NO 90
<211> LENGTH: 23
<212> TYPE: DNA
<213> ORGANISM: Sus scrofa

<400> SEQUENCE: 90 cttgaacccct tggggcagtc ggg                                          23

<210> SEQ ID NO 91
<211> LENGTH: 23
<212> TYPE: DNA
<213> ORGANISM: Sus scrofa

<400> SEQUENCE: 91
tcttgaaccc ttggggcagt cgg                                           23

<210> SEQ ID NO 92
<211> LENGTH: 23
<212> TYPE: DNA
<213> ORGANISM: Sus scrofa

<400> SEQUENCE: 92
cggggagttc ttgaaccctt ggg                                           23

<210> SEQ ID NO 93
<211> LENGTH: 23
<212> TYPE: DNA
<213> ORGANISM: Sus scrofa

<400> SEQUENCE: 93
tcggggagtt cttgaaccct tgg                                           23

<210> SEQ ID NO 94
<211> LENGTH: 23
<212> TYPE: DNA
<213> ORGANISM: Sus scrofa

<400> SEQUENCE: 94
gggcttcgtc aaagatggtc ggg                                           23

<210> SEQ ID NO 95
<211> LENGTH: 23
<212> TYPE: DNA
<213> ORGANISM: Sus scrofa

<400> SEQUENCE: 95
agggcttcgt caaagatggt cgg                                           23

<210> SEQ ID NO 96
<211> LENGTH: 23
<212> TYPE: DNA
<213> ORGANISM: Sus scrofa

<400> SEQUENCE: 96
gttggccagg tctctgtgta ggg                                           23

<210> SEQ ID NO 97
<211> LENGTH: 23
<212> TYPE: DNA
<213> ORGANISM: Sus scrofa

<400> SEQUENCE: 97
ggagggtcac ctgagggtgt tgg                                           23

<210> SEQ ID NO 98
<211> LENGTH: 23
<212> TYPE: DNA
<213> ORGANISM: Sus scrofa

-continued

```
<400> SEQUENCE: 98
gaagcaggtc atccacgtac tgg                                            23

<210> SEQ ID NO 99
<211> LENGTH: 23
<212> TYPE: DNA
<213> ORGANISM: Sus scrofa

<400> SEQUENCE: 99
ttctaagcag tcctgtttgg tgg                                            23

<210> SEQ ID NO 100
<211> LENGTH: 23
<212> TYPE: DNA
<213> ORGANISM: Sus scrofa

<400> SEQUENCE: 100
acagagacct ggccaacttc agg                                            23

<210> SEQ ID NO 101
<211> LENGTH: 23
<212> TYPE: DNA
<213> ORGANISM: Sus scrofa

<400> SEQUENCE: 101
ggtgaccctc ctccagtacg tgg                                            23

<210> SEQ ID NO 102
<211> LENGTH: 23
<212> TYPE: DNA
<213> ORGANISM: Sus scrofa

<400> SEQUENCE: 102
tctggcggga gccaccaaac agg                                            23

<210> SEQ ID NO 103
<211> LENGTH: 23
<212> TYPE: DNA
<213> ORGANISM: Sus scrofa

<400> SEQUENCE: 103
aggtacgaag gcactactgc tgg                                            23

<210> SEQ ID NO 104
<211> LENGTH: 23
<212> TYPE: DNA
<213> ORGANISM: Sus scrofa

<400> SEQUENCE: 104
agttggccag gtctctgtgt agg                                            23

<210> SEQ ID NO 105
<211> LENGTH: 23
<212> TYPE: DNA
<213> ORGANISM: Sus scrofa

<400> SEQUENCE: 105
agggtgttgg atcctgaagt tgg                                            23

<210> SEQ ID NO 106
<211> LENGTH: 23
<212> TYPE: DNA
<213> ORGANISM: Sus scrofa
```

```
<400> SEQUENCE: 106
gtcatccacg tactggagga ggg                                              23

<210> SEQ ID NO 107
<211> LENGTH: 23
<212> TYPE: DNA
<213> ORGANISM: Sus scrofa

<400> SEQUENCE: 107
tactggagga gggtcacctg agg                                              23

<210> SEQ ID NO 108
<211> LENGTH: 23
<212> TYPE: DNA
<213> ORGANISM: Sus scrofa

<400> SEQUENCE: 108
ggtcatccac gtactggagg agg                                              23

<210> SEQ ID NO 109
<211> LENGTH: 23
<212> TYPE: DNA
<213> ORGANISM: Sus scrofa

<400> SEQUENCE: 109
gcaggtcatc cacgtactgg agg                                              23

<210> SEQ ID NO 110
<211> LENGTH: 23
<212> TYPE: DNA
<213> ORGANISM: Sus scrofa

<400> SEQUENCE: 110
cgtggatgac ctgcttctgg cgg                                              23

<210> SEQ ID NO 111
<211> LENGTH: 23
<212> TYPE: DNA
<213> ORGANISM: Sus scrofa

<400> SEQUENCE: 111
gtggatgacc tgcttctggc ggg                                              23

<210> SEQ ID NO 112
<211> LENGTH: 23
<212> TYPE: DNA
<213> ORGANISM: Sus scrofa

<400> SEQUENCE: 112
accttctaag cagtcctgtt tgg                                              23

<210> SEQ ID NO 113
<211> LENGTH: 23
<212> TYPE: DNA
<213> ORGANISM: Sus scrofa

<400> SEQUENCE: 113
ggactgctta gaaggtacga agg                                              23

<210> SEQ ID NO 114
<211> LENGTH: 23
<212> TYPE: DNA
```

<213> ORGANISM: Sus scrofa

<400> SEQUENCE: 114
aatctgggcc ttcttagcag agg                                            23

<210> SEQ ID NO 115
<211> LENGTH: 23
<212> TYPE: DNA
<213> ORGANISM: Sus scrofa

<400> SEQUENCE: 115
ctaagaaggc ccagatttgc agg                                            23

<210> SEQ ID NO 116
<211> LENGTH: 23
<212> TYPE: DNA
<213> ORGANISM: Sus scrofa

<400> SEQUENCE: 116
catacttggg gtacagtttg cgg                                            23

<210> SEQ ID NO 117
<211> LENGTH: 23
<212> TYPE: DNA
<213> ORGANISM: Sus scrofa

<400> SEQUENCE: 117
ggcccagatt tgcaggagag agg                                            23

<210> SEQ ID NO 118
<211> LENGTH: 23
<212> TYPE: DNA
<213> ORGANISM: Sus scrofa

<400> SEQUENCE: 118
ttacctctct cctgcaaatc tgg                                            23

<210> SEQ ID NO 119
<211> LENGTH: 23
<212> TYPE: DNA
<213> ORGANISM: Sus scrofa

<400> SEQUENCE: 119
aggagagagg taacatactt ggg                                            23

<210> SEQ ID NO 120
<211> LENGTH: 23
<212> TYPE: DNA
<213> ORGANISM: Sus scrofa

<400> SEQUENCE: 120
ggagagaggt aacatacttg ggg                                            23

<210> SEQ ID NO 121
<211> LENGTH: 23
<212> TYPE: DNA
<213> ORGANISM: Sus scrofa

<400> SEQUENCE: 121
atacttgggg tacagtttgc ggg                                            23

<210> SEQ ID NO 122
<211> LENGTH: 23

```
<212> TYPE: DNA
<213> ORGANISM: Sus scrofa

<400> SEQUENCE: 122
ctttgccaaa cccatccctg cgg                                         23

<210> SEQ ID NO 123
<211> LENGTH: 23
<212> TYPE: DNA
<213> ORGANISM: Sus scrofa

<400> SEQUENCE: 123
gccttcagtt gaataacctg tgg                                         23

<210> SEQ ID NO 124
<211> LENGTH: 23
<212> TYPE: DNA
<213> ORGANISM: Sus scrofa

<400> SEQUENCE: 124
ggtagcaggg gagtattcca agg                                         23

<210> SEQ ID NO 125
<211> LENGTH: 23
<212> TYPE: DNA
<213> ORGANISM: Sus scrofa

<400> SEQUENCE: 125
gttcaaagat taatccaaca ggg                                         23

<210> SEQ ID NO 126
<211> LENGTH: 23
<212> TYPE: DNA
<213> ORGANISM: Sus scrofa

<400> SEQUENCE: 126
caagcctggg cagaaaccgc agg                                         23

<210> SEQ ID NO 127
<211> LENGTH: 23
<212> TYPE: DNA
<213> ORGANISM: Sus scrofa

<400> SEQUENCE: 127
tagcagggga gtattccaag ggg                                         23

<210> SEQ ID NO 128
<211> LENGTH: 23
<212> TYPE: DNA
<213> ORGANISM: Sus scrofa

<400> SEQUENCE: 128
gatattcatc atctaattgg agg                                         23

<210> SEQ ID NO 129
<211> LENGTH: 23
<212> TYPE: DNA
<213> ORGANISM: Sus scrofa

<400> SEQUENCE: 129
aagcctgggc agaaaccgca ggg                                         23

<210> SEQ ID NO 130
```

```
<211> LENGTH: 23
<212> TYPE: DNA
<213> ORGANISM: Sus scrofa

<400> SEQUENCE: 130
ctttgacgaa gccctacaca ggg                                              23

<210> SEQ ID NO 131
<211> LENGTH: 23
<212> TYPE: DNA
<213> ORGANISM: Sus scrofa

<400> SEQUENCE: 131
tacttggggt acagtttgcg ggg                                              23

<210> SEQ ID NO 132
<211> LENGTH: 23
<212> TYPE: DNA
<213> ORGANISM: Sus scrofa

<400> SEQUENCE: 132
acagtacccc ttgagtagag agg                                              23

<210> SEQ ID NO 133
<211> LENGTH: 23
<212> TYPE: DNA
<213> ORGANISM: Sus scrofa

<400> SEQUENCE: 133
gtagcagggg agtattccaa ggg                                              23

<210> SEQ ID NO 134
<211> LENGTH: 23
<212> TYPE: DNA
<213> ORGANISM: Sus scrofa

<400> SEQUENCE: 134
ttggggtaca gtttgcgggg cgg                                              23

<210> SEQ ID NO 135
<211> LENGTH: 23
<212> TYPE: DNA
<213> ORGANISM: Sus scrofa

<400> SEQUENCE: 135
cttcagttga ataacctgtg ggg                                              23

<210> SEQ ID NO 136
<211> LENGTH: 23
<212> TYPE: DNA
<213> ORGANISM: Sus scrofa

<400> SEQUENCE: 136
ttgagtagag aggctcgaga agg                                              23

<210> SEQ ID NO 137
<211> LENGTH: 23
<212> TYPE: DNA
<213> ORGANISM: Sus scrofa

<400> SEQUENCE: 137
gcggtttctg cccaggcttg ggg                                              23
```

```
<210> SEQ ID NO 138
<211> LENGTH: 23
<212> TYPE: DNA
<213> ORGANISM: Sus scrofa

<400> SEQUENCE: 138
gttggccagg tccctgtgta ggg                                            23

<210> SEQ ID NO 139
<211> LENGTH: 23
<212> TYPE: DNA
<213> ORGANISM: Sus scrofa

<400> SEQUENCE: 139 aagggattg gacaggaact agg                                             23

<210> SEQ ID NO 140
<211> LENGTH: 23
<212> TYPE: DNA
<213> ORGANISM: Sus scrofa

<400> SEQUENCE: 140
tcaagatata cagtcctggt tgg                                            23

<210> SEQ ID NO 141
<211> LENGTH: 23
<212> TYPE: DNA
<213> ORGANISM: Sus scrofa

<400> SEQUENCE: 141
ttcagttgaa taacctgtgg ggg                                            23

<210> SEQ ID NO 142
<211> LENGTH: 23
<212> TYPE: DNA
<213> ORGANISM: Sus scrofa

<400> SEQUENCE: 142
ctgggcagaa accgcaggga tgg                                            23

<210> SEQ ID NO 143
<211> LENGTH: 23
<212> TYPE: DNA
<213> ORGANISM: Sus scrofa

<400> SEQUENCE: 143
ttggggaaac tgctccaacc agg                                            23

<210> SEQ ID NO 144
<211> LENGTH: 23
<212> TYPE: DNA
<213> ORGANISM: Sus scrofa

<400> SEQUENCE: 144
ttggagggtc aacacagtga tgg                                            23

<210> SEQ ID NO 145
<211> LENGTH: 23
<212> TYPE: DNA
<213> ORGANISM: Sus scrofa

<400> SEQUENCE: 145
gtattccaag gggattggac agg                                            23
```

```
<210> SEQ ID NO 146
<211> LENGTH: 23
<212> TYPE: DNA
<213> ORGANISM: Sus scrofa

<400> SEQUENCE: 146
ctcgagcctc tctactcaag ggg                                              23

<210> SEQ ID NO 147
<211> LENGTH: 23
<212> TYPE: DNA
<213> ORGANISM: Sus scrofa

<400> SEQUENCE: 147
tctcgagcct ctctactcaa ggg                                              23

<210> SEQ ID NO 148
<211> LENGTH: 23
<212> TYPE: DNA
<213> ORGANISM: Sus scrofa

<400> SEQUENCE: 148
gagaggctcg agaaggaatt tgg                                              23

<210> SEQ ID NO 149
<211> LENGTH: 23
<212> TYPE: DNA
<213> ORGANISM: Sus scrofa

<400> SEQUENCE: 149
tgttcaaaga ttaatccaac agg                                              23

<210> SEQ ID NO 150
<211> LENGTH: 23
<212> TYPE: DNA
<213> ORGANISM: Sus scrofa

<400> SEQUENCE: 150
tcttgatcag gctttacttg ggg                                              23

<210> SEQ ID NO 151
<211> LENGTH: 23
<212> TYPE: DNA
<213> ORGANISM: Sus scrofa

<400> SEQUENCE: 151
tggattaatc tttgaacatg cgg                                              23

<210> SEQ ID NO 152
<211> LENGTH: 23
<212> TYPE: DNA
<213> ORGANISM: Sus scrofa

<400> SEQUENCE: 152
ggagcagttt ccccaagcct ggg                                              23

<210> SEQ ID NO 153
<211> LENGTH: 23
<212> TYPE: DNA
<213> ORGANISM: Sus scrofa

<400> SEQUENCE: 153
ttctcgagcc tctctactca agg                                              23
```

<210> SEQ ID NO 154
<211> LENGTH: 23
<212> TYPE: DNA
<213> ORGANISM: Sus scrofa

<400> SEQUENCE: 154
tagttcctgt ccaatcccct tgg                                              23

<210> SEQ ID NO 155
<211> LENGTH: 23
<212> TYPE: DNA
<213> ORGANISM: Sus scrofa

<400> SEQUENCE: 155
cgaagcccta cacagggacc tgg                                              23

<210> SEQ ID NO 156
<211> LENGTH: 23
<212> TYPE: DNA
<213> ORGANISM: Sus scrofa

<400> SEQUENCE: 156
atattcatca tctaattgga ggg                                              23

<210> SEQ ID NO 157
<211> LENGTH: 23
<212> TYPE: DNA
<213> ORGANISM: Sus scrofa

<400> SEQUENCE: 157
caggaactag gatgccctgt tgg                                              23

<210> SEQ ID NO 158
<211> LENGTH: 23
<212> TYPE: DNA
<213> ORGANISM: Sus scrofa

<400> SEQUENCE: 158
ggcaaagcaa gttcccccac agg                                              23

<210> SEQ ID NO 159
<211> LENGTH: 23
<212> TYPE: DNA
<213> ORGANISM: Sus scrofa

<400> SEQUENCE: 159
tggagcagtt tccccaagcc tgg                                              23

<210> SEQ ID NO 160
<211> LENGTH: 23
<212> TYPE: DNA
<213> ORGANISM: Sus scrofa

<400> SEQUENCE: 160
agaaaccgca gggatgggtt tgg                                              23

<210> SEQ ID NO 161
<211> LENGTH: 23
<212> TYPE: DNA
<213> ORGANISM: Sus scrofa

<400> SEQUENCE: 161
cccacaggtt attcaactga agg    23

<210> SEQ ID NO 162
<211> LENGTH: 23
<212> TYPE: DNA
<213> ORGANISM: Sus scrofa

<400> SEQUENCE: 162
gctcaaattt cttttgaaca agg    23

<210> SEQ ID NO 163
<211> LENGTH: 23
<212> TYPE: DNA
<213> ORGANISM: Sus scrofa

<400> SEQUENCE: 163
tgggcagaaa ccgcagggat ggg    23

<210> SEQ ID NO 164
<211> LENGTH: 23
<212> TYPE: DNA
<213> ORGANISM: Sus scrofa

<400> SEQUENCE: 164
tctttgacga agccctacac agg    23

<210> SEQ ID NO 165
<211> LENGTH: 23
<212> TYPE: DNA
<213> ORGANISM: Sus scrofa

<400> SEQUENCE: 165
acagggacct ggccaacttc agg    23

<210> SEQ ID NO 166
<211> LENGTH: 23
<212> TYPE: DNA
<213> ORGANISM: Sus scrofa

<400> SEQUENCE: 166
ggggagtatt ccaaggggat tgg    23

<210> SEQ ID NO 167
<211> LENGTH: 23
<212> TYPE: DNA
<213> ORGANISM: Sus scrofa

<400> SEQUENCE: 167
tggagggtca acacagtgat ggg    23

<210> SEQ ID NO 168
<211> LENGTH: 23
<212> TYPE: DNA
<213> ORGANISM: Sus scrofa

<400> SEQUENCE: 168
gtcgatattc atcatctaat tgg    23

<210> SEQ ID NO 169
<211> LENGTH: 23
<212> TYPE: DNA
<213> ORGANISM: Sus scrofa

<400> SEQUENCE: 169
catccctgcg gtttctgccc agg                                      23

<210> SEQ ID NO 170
<211> LENGTH: 23
<212> TYPE: DNA
<213> ORGANISM: Sus scrofa

<400> SEQUENCE: 170
atcttgatca ggctttactt ggg                                      23

<210> SEQ ID NO 171
<211> LENGTH: 23
<212> TYPE: DNA
<213> ORGANISM: Sus scrofa

<400> SEQUENCE: 171
ctgatcaaga tatacagtcc tgg                                      23

<210> SEQ ID NO 172
<211> LENGTH: 23
<212> TYPE: DNA
<213> ORGANISM: Sus scrofa

<400> SEQUENCE: 172
tatcttgatc aggctttact tgg                                      23

<210> SEQ ID NO 173
<211> LENGTH: 23
<212> TYPE: DNA
<213> ORGANISM: Sus scrofa

<400> SEQUENCE: 173
ttgttattca cagacacttc tgg                                      23

<210> SEQ ID NO 174
<211> LENGTH: 23
<212> TYPE: DNA
<213> ORGANISM: Sus scrofa

<400> SEQUENCE: 174
gactgatact ggtgtagcac tgg                                      23

<210> SEQ ID NO 175
<211> LENGTH: 23
<212> TYPE: DNA
<213> ORGANISM: Sus scrofa

<400> SEQUENCE: 175
agttggccag gtccctgtgt agg                                      23

<210> SEQ ID NO 176
<211> LENGTH: 23
<212> TYPE: DNA
<213> ORGANISM: Sus scrofa

<400> SEQUENCE: 176
tgcggtttct gcccaggctt ggg                                      23

<210> SEQ ID NO 177
<211> LENGTH: 23
<212> TYPE: DNA
<213> ORGANISM: Sus scrofa

<400> SEQUENCE: 177
ttggaatact cccctgctac cgg                                    23

<210> SEQ ID NO 178
<211> LENGTH: 23
<212> TYPE: DNA
<213> ORGANISM: Sus scrofa

<400> SEQUENCE: 178
caggactgta tatcttgatc agg                                    23

<210> SEQ ID NO 179
<211> LENGTH: 23
<212> TYPE: DNA
<213> ORGANISM: Sus scrofa

<400> SEQUENCE: 179
tggggtacag tttgcggggc ggg                                    23

<210> SEQ ID NO 180
<211> LENGTH: 23
<212> TYPE: DNA
<213> ORGANISM: Sus scrofa

<400> SEQUENCE: 180
gggtactgtc tgactgatac tgg                                    23

<210> SEQ ID NO 181
<211> LENGTH: 23
<212> TYPE: DNA
<213> ORGANISM: Sus scrofa

<400> SEQUENCE: 181
ctgcggtttc tgcccaggct tgg                                    23

<210> SEQ ID NO 182
<211> LENGTH: 42
<212> TYPE: DNA
<213> ORGANISM: Artificial Sequence
<220> FEATURE:
<223> OTHER INFORMATION: Synthetic

<400> SEQUENCE: 182
gaccattacc aagcagggtc tgacaggtac tgaaaggatg aa               42

<210> SEQ ID NO 183
<211> LENGTH: 42
<212> TYPE: DNA
<213> ORGANISM: Artificial Sequence
<220> FEATURE:
<223> OTHER INFORMATION: Synthetic

<400> SEQUENCE: 183
attaaacaac tcagccgggt gcggtgcctc tgaaaggatg aa               42

<210> SEQ ID NO 184
<211> LENGTH: 42
<212> TYPE: DNA
<213> ORGANISM: Artificial Sequence
<220> FEATURE:
<223> OTHER INFORMATION: Synthetic

<400> SEQUENCE: 184
aactgtatag tcttggataa acagttcagg tgaaaggatg aa               42

<210> SEQ ID NO 185
<211> LENGTH: 42
<212> TYPE: DNA
<213> ORGANISM: Artificial Sequence
<220> FEATURE:
<223> OTHER INFORMATION: Synthetic

<400> SEQUENCE: 185
cgtgggaaac aggggctccg cgactgcgct tgaaaggatg aa        42

<210> SEQ ID NO 186
<211> LENGTH: 42
<212> TYPE: DNA
<213> ORGANISM: Artificial Sequence
<220> FEATURE:
<223> OTHER INFORMATION: Synthetic

<400> SEQUENCE: 186
gcaaatgtct ttattgtttg ttgctggttt tgaaaggatg aa        42

<210> SEQ ID NO 187
<211> LENGTH: 42
<212> TYPE: DNA
<213> ORGANISM: Artificial Sequence
<220> FEATURE:
<223> OTHER INFORMATION: Synthetic

<400> SEQUENCE: 187
ggagtgcagt gatctgatct ccgctcatgg tgaaaggatg aa        42

<210> SEQ ID NO 188
<211> LENGTH: 42
<212> TYPE: DNA
<213> ORGANISM: Artificial Sequence
<220> FEATURE:
<223> OTHER INFORMATION: Synthetic

<400> SEQUENCE: 188
ccgttcctcc caaggcgggc cttgaaagga tgaaaggatg aa        42

<210> SEQ ID NO 189
<211> LENGTH: 22
<212> TYPE: DNA
<213> ORGANISM: Sus scrofa

<400> SEQUENCE: 189
actctatcct ataaggttga ca        22

<210> SEQ ID NO 190
<211> LENGTH: 20
<212> TYPE: DNA
<213> ORGANISM: Sus scrofa

<400> SEQUENCE: 190
taggttgcat tttcatcctt        20

<210> SEQ ID NO 191
<211> LENGTH: 19
<212> TYPE: DNA
<213> ORGANISM: Sus scrofa

<400> SEQUENCE: 191
ggagcaaaag agcagtatg        19

```
<210> SEQ ID NO 192
<211> LENGTH: 20
<212> TYPE: DNA
<213> ORGANISM: Sus scrofa

<400> SEQUENCE: 192
taggttgcat tttcatcctt                                               20

<210> SEQ ID NO 193
<211> LENGTH: 20
<212> TYPE: DNA
<213> ORGANISM: Sus scrofa

<400> SEQUENCE: 193
tatatggacg cattcagttg                                               20

<210> SEQ ID NO 194
<211> LENGTH: 20
<212> TYPE: DNA
<213> ORGANISM: Sus scrofa

<400> SEQUENCE: 194
taggttgcat tttcatcctt                                               20

<210> SEQ ID NO 195
<211> LENGTH: 19
<212> TYPE: DNA
<213> ORGANISM: Sus scrofa

<400> SEQUENCE: 195
ttttcggagg attttcagg                                                19

<210> SEQ ID NO 196
<211> LENGTH: 20
<212> TYPE: DNA
<213> ORGANISM: Sus scrofa

<400> SEQUENCE: 196
taggttgcat tttcatcctt                                               20

<210> SEQ ID NO 197
<211> LENGTH: 20
<212> TYPE: DNA
<213> ORGANISM: Sus scrofa

<400> SEQUENCE: 197
tactgcattt gataccacat                                               20

<210> SEQ ID NO 198
<211> LENGTH: 20
<212> TYPE: DNA
<213> ORGANISM: Sus scrofa

<400> SEQUENCE: 198
taggttgcat tttcatcctt                                               20

<210> SEQ ID NO 199
<211> LENGTH: 22
<212> TYPE: DNA
<213> ORGANISM: Sus scrofa

<400> SEQUENCE: 199
gacttccgtc atttatgtaa ac                                            22
```

```
<210> SEQ ID NO 200
<211> LENGTH: 20
<212> TYPE: DNA
<213> ORGANISM: Sus scrofa

<400> SEQUENCE: 200
taggttgcat tttcatcctt                                                   20

<210> SEQ ID NO 201
<211> LENGTH: 18
<212> TYPE: DNA
<213> ORGANISM: Sus scrofa

<400> SEQUENCE: 201
ctctggtcgt ttcagtgg                                                     18

<210> SEQ ID NO 202
<211> LENGTH: 20
<212> TYPE: DNA
<213> ORGANISM: Sus scrofa

<400> SEQUENCE: 202
taggttgcat tttcatcctt                                                   20

<210> SEQ ID NO 203
<211> LENGTH: 18
<212> TYPE: DNA
<213> ORGANISM: Sus scrofa

<400> SEQUENCE: 203
cagatgagtg gagcaagg                                                     18

<210> SEQ ID NO 204
<211> LENGTH: 20
<212> TYPE: DNA
<213> ORGANISM: Sus scrofa

<400> SEQUENCE: 204
taggttgcat tttcatcctt                                                   20

<210> SEQ ID NO 205
<211> LENGTH: 19
<212> TYPE: DNA
<213> ORGANISM: Sus scrofa

<400> SEQUENCE: 205
gttactgggt cagggataa                                                    19

<210> SEQ ID NO 206
<211> LENGTH: 20
<212> TYPE: DNA
<213> ORGANISM: Sus scrofa

<400> SEQUENCE: 206
taggttgcat tttcatcctt                                                   20

<210> SEQ ID NO 207
<211> LENGTH: 22
<212> TYPE: DNA
<213> ORGANISM: Sus scrofa

<400> SEQUENCE: 207
```
ccctccatat acattttctc ta    22

<210> SEQ ID NO 208
<211> LENGTH: 20
<212> TYPE: DNA
<213> ORGANISM: Sus scrofa

<400> SEQUENCE: 208
taggttgcat tttcatcctt    20

<210> SEQ ID NO 209
<211> LENGTH: 18
<212> TYPE: DNA
<213> ORGANISM: Sus scrofa

<400> SEQUENCE: 209
gagtcccatt caccaagt    18

<210> SEQ ID NO 210
<211> LENGTH: 20
<212> TYPE: DNA
<213> ORGANISM: Sus scrofa

<400> SEQUENCE: 210
taggttgcat tttcatcctt    20

<210> SEQ ID NO 211
<211> LENGTH: 18
<212> TYPE: DNA
<213> ORGANISM: Sus scrofa

<400> SEQUENCE: 211
acgcacaaga caaagaca    18

<210> SEQ ID NO 212
<211> LENGTH: 19
<212> TYPE: DNA
<213> ORGANISM: Sus scrofa

<400> SEQUENCE: 212
ctcccaccca gtttcatag    19

<210> SEQ ID NO 213
<211> LENGTH: 17
<212> TYPE: DNA
<213> ORGANISM: Sus scrofa

<400> SEQUENCE: 213
cccgcaaatc tcacgag    17

<210> SEQ ID NO 214
<211> LENGTH: 17
<212> TYPE: DNA
<213> ORGANISM: Sus scrofa

<400> SEQUENCE: 214
cccgcaaatc tcacgag    17

<210> SEQ ID NO 215
<211> LENGTH: 18
<212> TYPE: DNA
<213> ORGANISM: Sus scrofa

<400> SEQUENCE: 215

-continued

```
gtttgacagt ggtgttgt                                          18

<210> SEQ ID NO 216
<211> LENGTH: 20
<212> TYPE: DNA
<213> ORGANISM: Sus scrofa

<400> SEQUENCE: 216
taggttgcat tttcatcctt                                        20

<210> SEQ ID NO 217
<211> LENGTH: 20
<212> TYPE: DNA
<213> ORGANISM: Sus scrofa

<400> SEQUENCE: 217
tgttgagaca atagggtgat                                        20

<210> SEQ ID NO 218
<211> LENGTH: 20
<212> TYPE: DNA
<213> ORGANISM: Sus scrofa

<400> SEQUENCE: 218
taggttgcat tttcatcctt                                        20

<210> SEQ ID NO 219
<211> LENGTH: 20
<212> TYPE: DNA
<213> ORGANISM: Sus scrofa

<400> SEQUENCE: 219
tcatgaacaa gtgctgtatt                                        20

<210> SEQ ID NO 220
<211> LENGTH: 20
<212> TYPE: DNA
<213> ORGANISM: Sus scrofa

<400> SEQUENCE: 220
taggttgcat tttcatcctt                                        20

<210> SEQ ID NO 221
<211> LENGTH: 21
<212> TYPE: DNA
<213> ORGANISM: Sus scrofa

<400> SEQUENCE: 221
ggaatagatt gtcttgggaa t                                      21

<210> SEQ ID NO 222
<211> LENGTH: 20
<212> TYPE: DNA
<213> ORGANISM: Sus scrofa

<400> SEQUENCE: 222
taggttgcat tttcatcctt                                        20

<210> SEQ ID NO 223
<211> LENGTH: 17
<212> TYPE: DNA
<213> ORGANISM: Sus scrofa
```

<400> SEQUENCE: 223
ggctctctgg ggcatct                                                  17

<210> SEQ ID NO 224
<211> LENGTH: 17
<212> TYPE: DNA
<213> ORGANISM: Sus scrofa

<400> SEQUENCE: 224 cagggggcctg gggaatg                                                 17

<210> SEQ ID NO 225
<211> LENGTH: 19
<212> TYPE: DNA
<213> ORGANISM: Sus scrofa

<400> SEQUENCE: 225
tgtttgagag gcagaagat                                                19

<210> SEQ ID NO 226
<211> LENGTH: 20
<212> TYPE: DNA
<213> ORGANISM: Sus scrofa

<400> SEQUENCE: 226
taggttgcat tttcatcctt                                               20

<210> SEQ ID NO 227
<211> LENGTH: 19
<212> TYPE: DNA
<213> ORGANISM: Sus scrofa

<400> SEQUENCE: 227
aggtacttgg tggtgaatg                                                19

<210> SEQ ID NO 228
<211> LENGTH: 20
<212> TYPE: DNA
<213> ORGANISM: Sus scrofa

<400> SEQUENCE: 228
taggttgcat tttcatcctt                                               20

<210> SEQ ID NO 229
<211> LENGTH: 22
<212> TYPE: DNA
<213> ORGANISM: Sus scrofa

<400> SEQUENCE: 229
tgagtatcag tatcatttgt ga                                            22

<210> SEQ ID NO 230
<211> LENGTH: 20
<212> TYPE: DNA
<213> ORGANISM: Sus scrofa

<400> SEQUENCE: 230
taggttgcat tttcatcctt                                               20

<210> SEQ ID NO 231
<211> LENGTH: 21
<212> TYPE: DNA
<213> ORGANISM: Sus scrofa

```
<400> SEQUENCE: 231
tctctcctgc aaatctgggc c                                            21
```